(12) United States Patent
Du et al.

(10) Patent No.: US 9,597,358 B2
(45) Date of Patent: Mar. 21, 2017

(54) BIOENGINEERED HUMAN CORNEAL STROMAL TISSUE

(75) Inventors: Yiqin Du, Pittsburgh, PA (US); James L. Funderburgh, Pittsburgh, PA (US); William R. Wagner, Wexford, PA (US); Jian Wu, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 520 days.

(21) Appl. No.: 13/581,707

(22) PCT Filed: Mar. 4, 2011

(86) PCT No.: PCT/US2011/027195
§ 371 (c)(1),
(2), (4) Date: Nov. 9, 2012

(87) PCT Pub. No.: WO2011/109712
PCT Pub. Date: Sep. 9, 2011

(65) Prior Publication Data
US 2013/0209571 A1 Aug. 15, 2013

Related U.S. Application Data

(60) Provisional application No. 61/310,559, filed on Mar. 4, 2010.

(51) Int. Cl.
*A61K 35/30* (2015.01)
*C12N 5/00* (2006.01)
*C12N 5/0775* (2010.01)

(52) U.S. Cl.
CPC ............ *A61K 35/30* (2013.01); *C12N 5/0068* (2013.01); *C12N 5/0667* (2013.01); *C12N 5/0668* (2013.01); *C12N 2533/30* (2013.01)

(58) Field of Classification Search
None
See application file for complete search history.

(56) References Cited

U.S. PATENT DOCUMENTS

| | | |
|---|---|---|
| 5,262,055 A | 11/1993 | Bae et al. |
| 6,777,231 B1 | 8/2004 | Katz et al. |
| 7,470,537 B2 | 12/2008 | Hedrick et al. |
| 2005/0019488 A1 | 1/2005 | Braithwaite et al. |
| 2008/0096975 A1 | 4/2008 | Guan et al. |

FOREIGN PATENT DOCUMENTS

EP 1902739 A1 3/2008

OTHER PUBLICATIONS

Badylak, The extracellular matrix as a biological scaffold material, Biomaterials, 28 (2007) 3587-3593.*

(Continued)

*Primary Examiner* — Karen Cochrane Carlson
*Assistant Examiner* — Jennifer M. H. Tichy
(74) *Attorney, Agent, or Firm* — The Webb Law Firm

(57) ABSTRACT

Provided herein is a method of making an aligned ECM scaffold useful in refractive correction of the eye and repair of the cornea. Methods of use of the scaffold as well as a scaffold construct are provided.

15 Claims, 25 Drawing Sheets

(56) References Cited

OTHER PUBLICATIONS

Shimizu et al., Fabrication of Pulsatile Cardiac Tissue Grafts Using a Novel 3-Dimensional Cell Sheet Manipulation Technique and Temperature-Responsive Cell Culture Surfaces, Circulation Research, Feb. 22, 2002, pp. 1-9.*
Stella et al., Tissue-to-cellular level deformation coupling in cell micro-integrated elastomeric scaffolds, Biomaterials, vol. 29, Issue 22, Aug. 2008, pp. 3228-3236.*
Hashimoto et al., Preparation and characterization of decellularized cornea using high-hydrostatic pressurization for corneal tissue engineering, Biomaterials vol. 31, Issue 14, May 2010, pp. 3941-3948.*
Aiken-O'Neill and Mannis, Summary of Corneal Transplant Activity, Cornea, 2002, 1-3, vol. 21, No. 1, Lippincott Williams & Wilkins, Inc., Philadelphia.
Akama et al., Macular Corneal Dystrophy Type I and Type II are Caused by Distinct Mutations in a New Sulphotransferase Gene, Nature Genetics, Oct. 2000, 237-241, vol. 26.
Aksu et al., Role of Gender and Anatomical Region on Induction of Osteogenic Differentiation of Human Adipose-derived Stem Cells, Annals of Plastic Surgery, Mar. 2008, 306-22, vol. 60, No. 3, Lippincott Williams & Wilkins.
Altman et al., IFATS Collection: Human Adipose-derived Stem Cells Seeded on a Silk Fibroin-Chitosan Scaffold Enhance Wound Repair in a Murine Soft Tissue Injury Model, Stem Cells, 2009, 250-258, vol. 27.
Arnalich-Montiel et al., Adipose-derived Stem Cells are a Source for Cell Therapy of the Corneal Stroma, Stem Cells, 2008, 570-579, vol. 26.
Bashur et al., Effect of Fiber Diameter and Alignment of Electrospun Polyurethane Meshes on Mesenchymal Progenitor Cells, Tissue Engineering: Part A, 2009, 2435-2445, vol. 15, No. 9.
Benjamin et al., Structure-function Relationships in Tendons: a Review, J. Anat., 2008, 211-228, vol. 212.
Beales et al., Proteoglycan Synthesis by Bovine Keratocytes and Corneal Fibroblasts: Maintenance of the Keratocyte Phenotype in Culture, Investigative Opthalmology & Visual Science, Jul. 1999, 1658-1663, vol. 40, No. 8.
Birk et al., Collagen Fibrillogenesis In Vitro: Interaction of Types I and V Collagen Regulates Fibril Diameter, Journal of Cell Science, 1990, 649-657, vol. 95, The Company of Biologists Limited, Great Britain.
Birk et al., Organization of Collagen Types I and V in the Embryonic Chicken Cornea, Investigative Opthalmology & Visual Science, 1986, 1470-1477, vol. 27.
Birk, Type V Collagen: Heterotypic Type I/V Collagen Interactions in the Regulation of Fibril Assembly, Micron, 2001, 223-237, vol. 32.
Bitar et al., Effect of Multiple Unconfined Compression on Cellular Dense Collagen Scaffolds for Bone Tissue Engineering, J Mater Sci.: Mater Med, 2007, 237-244, vol. 18.
Brown et al., Ultrarapid Engineering of Biomimetic Materials and Tissues: Fabrication of Nano- and Microstructures by Plastic Compression, Advanced Functional Materials, 2005, 1762-1770, vol. 15.
Cahalan et al., Two-Photon Tissue Imaging: Seeing the Immune System in a Fresh Light, Nat. Rev. Immunol., Nov. 2002, 872-880, vol. 2.
Carlson et al., Keratocan, a Cornea-Specific Keratan Sulfate Proteoglycan, is Regulated by Lumican, The Journal of Biological Chemistry, Jul. 8, 2005, 25541-25547, vol. 280, No. 27.
Chakravarti et al., Collagen Fibril Assembly During Postnatal Development and Dysfunctional Regulation in the Lumican-Deficient Murine Cornea, Developmental Dynamics, 2006, 2493-2506, vol. 235.
Chakravarti et al., Lumican Regulates Collagen Fibril Assembly: Skin Fragility and Corneal Opacitiy in the Absence of Lumican, The Journal of Cell Biology, Jun. 1, 1998, 1277-1286, vol. 141, No. 5.
Challen and Little, A Side Order of Stem Cells: the SP Phenotype, Stem Cells, 2006, 3-12, vol. 24.
Courtney et al., Design and Analysis of Tissue Engineering Scaffolds that Mimic Soft Tissue Mechanical Anisotrophy, Biomaterials, 2006, 3631-3638, vol. 27.
Du et al., Adipose-derived Stem Cells Differentiate to Keratocytes in Vitro, Molecular Vision, Dec. 10, 2010, 2680-2689, vol. 16.
Du et al., Multipotent Stem Cells in Human Corneal Stroma, Stem Cells, Oct. 2005, 1266-1275, vol. 23, No. 9.
Du et al., Secretion and Organization of a Cornea-Like Tissue In Vitro by Stem Cells from Human Corneal Stroma, Investigative Opthalmology & Visual Science, Nov. 2007, vol. 48, No. 11.
Du et al., Stem Cell Therapy Restores Transparency to Defective Murine Corneas, Stem Cells, 2009, 1635-1642, vol. 27, No. 27.
Espana et al., Human Keratocytes Cultured on Amniotic Membrane Stroma Preserve Morphology and Express Keratocan, Investigative Ophthalmology & Visual Science, Dec. 2003, 5136-5141, vol. 44, No. 12.
Fini, Keratocyte and Fibroblast Phenotypes in the Repairing Cornea, Progress in Retinal and Eye Research, 1999, 529-551, vol. 18, No. 4, Elsevier Science Ltd., Great Britain.
Funderburgh et al., Distribution of Proteoglycans Antigenically Related to Corneal Keratan Sulfate Proteoglycan, The Journal of Biological Chemistry, Aug. 25, 1987, 11634-11640, vol. 262, No. 24, USA.
Funderburgh et al., Keratocyte Phenotype is Enhanced in the Absence of Attachment to the Substratum, Molecular Vision, Feb. 9, 2008, 308-317, vol. 14.
Funderburgh et al., Keratocyte Phenotype Mediates Proteoglycan Structure: A Role for Fibroblasts in Corneal Fibrosis, J. Biol.Chem., Nov. 14, 2003, 45629-45637, vol. 278, No. 46.
Funderburgh, Keratan Sulfate: Structure, Biosynthesis, and Function, Glycobiology, 2000, 951-958, vol. 10, No. 10.
Funderburgh et al., Keratan Sulfate Proteoglycan During Embryonic Development of the Chicken Cornea, Developmental Biology, 1986, 267-277, vol. 116.
Funderburgh et al., PAX6 Expression Identifies Progenitor Cells for Corneal Keratocytes, FASEB J., Aug. 2005, 1371-1373, vol. 19, No. 10.
Funderburgh et al., Proteoglycan Expression During Transforming Growth Factor Beta-Induced Keratocyte-Myofibroblast Transdifferentiation, J, Biol. Chem. Nov. 23, 2001, 44173-44178, vol. 276, No. 47.
Funderburgh et al., Synthesis of Corneal Keratan Sulfate Proteoglycans by Bovine Keratocytes in Vitro., The Journal of Biological Chemistry, Dec. 6, 1996, 31431-31436, vol. 271, No. 49.
Gerecht et al., The Effect of Actin Disrupting Agents on Contact Guidance of Human Embryonic Stem Cells, Biomaterials, 2007, 4068-4077, vol. 28.
Girton et al., Confined Compression of a Tissue-Equivalent: Collagen Fibril and Cell Alignment in Response to Anisotropic Strain, J. Biomech, Eng., Oct. 2002, 568-575, vol. 124.
Goodell et al., Isolation and Functional Properties of Murine Hematopoietic Stem Cells that are Replicating In Vivo, J. Exp. Med., Apr. 1996, 1797-1806, vol. 183.
Guan et al., Preparation and Characterization of Highly Porous, Biodegradable Polyurethane Scaffolds for Soft Tissue Applications, Biomaterials, 2005, 3961-3971, vol. 26.
Guan et al., Synthesis, Characterization, and Cytocompatibility of Elastomeric, Biodegradable Poly(ester-urethane) ureas Based on Poly(caprolactone) and Putrescine, J. Biomed. Mater. Res., 2002, 493-503, vol. 61.
Guido and Tranquillo, A Methodology for the Systematic and Quantitative Study of Cell Contact Guidance in Oriented Collagen Gels, Journal of Cell Science, 1993, 317-331, vol. 105.
Guillemette et al., Surface Topography Induces 3D Self-orientation of Cells and Extracellular Matrix Resulting in Improved Tissue Function, Integrative Biology, 2009, 196-204, vol. 1.
Guo et al., Morphologic Characterization of Organized Extracellular Matrix Deposition by Ascorbic Acid-Stimulated Human Corneal Fibroblasts, Investigative Opthalmology & Visual Science, Sep. 2007, 4050-4060, vol. 48, No. 9, Association for Research in Vision and Opthalmolgy.
Hadjipanayi et al., Interface Integration of Layered Collagen Scaffolds with Defined Matrix Stiffness: Implications for Sheet-Based

(56) References Cited

OTHER PUBLICATIONS

Tissue Engineering, Journal of Tissue Engineering and Regenerative Medicine, Mar. 9, 2009, 230-241, vol. 3, John Wiley & Sons, Ltd.

Hassell et al., Macular Corneal Dystrophy: Failure to Synthesize a Mature Keratin Sulfate Proteoglycan, Proc. Natl. Acad. Sci., Jun. 1980, 3705-3709, vol. 77, No. 6, USA.

Jester et al., Induction of α-Smooth Muscle Actin Expression and Myofibroblast Trnasfromation in Cultured Corneal Keratocytes, Cornea, 1996, 505-516, vol. 15, No. 5.

Jester et al., The Cellular Basis of Corneal Transparency: Evidence for 'Corneal Crystallins,' Journal of Cell Science, 1999, 613-622, vol. 112, The Company of Biologists Limited, Great Britain.

Jiang et al., Pluripotency of Mesenchymal Stem Cells Derived from Adult Marrow, Nature, Jul. 4, 2002, 41-49, vol. 418.

Kao and Liu, Roles of Lumican and Keratocan on Corneal Transparency, Glycoconjugate Journal, 2003, 275-285, vol. 19.

Kim et al., Antiwrinkle Effect of Adipose-derived Stem Cell: Activation of Dermal Fibroblast by Secretory Factors, Journal of Dermatological Science, 2009, 96-102, vol. 53, Elsevier Ireland Ltd.

Kim et al., Evidence Supporting Antioxidant Action of Adipose-derived Stem Cells: Protection of Human Dermal Fibroblasts from Oxidative Stress, Journal of Dermatological Science, 2008, 133-142, vol. 49.

Kim et al., Wound Healing Effect of Adipose-derived Stem Cells: A Critical Role of Secretory Factors on Human Dermal Fibroblasts, Journal of Dermatological Science, 2007, 15-24, vol. 48.

Langer and Vacanti, Tissue Engineering, Science, May 14, 1993, 920-926, vol. 260, No. 5110.

Li et al., Electrospinning Nanofibers as Uniaxially Aligned Arrays and Layer-by-Layer Stacked Films, Advanced Materials, Feb. 17, 2004, 361-366, vol. 16, No. 4.

Long et al., Fibroblast Growth Factor-2 Promotes Keratan Sulfate Proteoglycan Expression by Keratocytes In Vitro, The Journal of Biological Chemistry, May 5, 2000, 13918-13923, vol. 275, No. 18.

McIntosh et al., The Immunogenicity of Human Adipose-derived Cells: Temporal Changes In Vitro, Stem Cells, 2006, 1246-1253, vol. 24.

McLaughlin et al., Bioengineered Corneas for Transplantation and In Vitro Toxicology, Frontiers in Bioscience, Jan. 1, 2009, 3326-3337, vol. 14.

Meek and Boote, The Organization of Collagen in the Corneal Stroma, Experimental Eye Research, 2004, 503-512, vol. 78.

Meek and Leonard, Ultrastructure of the Corneal Stroma: A Comparative Study, Biophys. J., Jan. 1993, 273-280, vol. 64.

Musselmann et al., Isolation of a Putative Keratocyte Activating Factor from the Corneal Stroma, Experimental Eye Research, Apr. 7, 2003, 273-279, vol. 77.

Naylor, Polarized Light Studies of Corneal Structure, Brit. J. Ophthal., 1953, 77-84, vol. 37.

Ottani et al., Collagen Structure and Functional Implications, Micron, 2001, 251-260, vol. 32.

Pellegata et al., Mutations in KERA, Encoding Keratocan, Cause Cornea Plana, Nature Genetics, May 2000, 91-95, vol. 25.

Ruberti and Zieske, Prelude to Corneal Tissue Engineering—Gaining Control of Collagen Orgnaization, Progress in Retinal and Eye Research, 2008, 549-577, vol. 27.

Stankus et al., Fabrication of Biodegradable Elastomeric Scaffolds with Sub-Micron Morphologies, J. Biomed. Mater. Res. Part A., Sep. 15, 2004, 603-614, vol. 70, No. 4.

Stankus et al., Fabrication of Cell Microintegrated Blood Vessel Constructs through Electrohydrodynamic Atomization, Biomaterials, 2007, 2738-2746, vol. 28.

Tandon et al., Role of Transforming Growth Factor Beta in Corneal Function, Biology and Pathology, Curr. Mol. Med., Aug. 1, 2010, 565-578, vol. 10, No. 6.

Temenoff and Mikos, Review: Tissue Engineering for Regeneration of Articular Cartilage, Biomaterials, 2000, 431-440, vol. 21.

Tholpady et al., Adipose Tissue: Stem Cells and Beyond, Clinics in Plastic Surgery, 55-62, 2006, vol. 33.

Thompson et al., Long-term Graft Survival after Penetrating Keratoplasty, Ophthalmology, Jul. 2003, 1396-1402, vol. 110, No. 7.

Torbet et al., Orthogonal Scaffold of Magnetically Aligned Collagen Lamellae for Corneal Stroma Reconstruction, Biomaterials, 2007, 4268-4276, vol. 28.

Vanderby, Collagen in Connective Tissue: from Tendon to Bone, J. Biomechan., 2003, 1523-1527, vol. 36, No. 10.

Weiner and Traub, Bone Structure: from ångstroms to Microns, The FASEB Journal, 1992, 879-885, vol. 6.

Whicter et al., Corneal Blindness: a Global Perspective, Bulletin of the World Health Organization, 2001, 214-221, vol. 79, No. 3.

Williams et al., Interpreting Second-Harmonic Generation Images of Collagen I Fibrils, Biophysical Journal, Feb. 2005, 1377-1386, vol. 88.

Wise et al., Chondrogenic Differentiaion of Human Mesenchymal Stem Cells on Oriented Nanofibrous Scaffolds: Engineering the Superficial Zone of Articular Cartilage, Tissue Engineering: Part A, 2009, 913-921, vol. 15, No. 4.

Wolman and Kasten, Polarized Light Microscopy in the Study of the Molecular Structure of Collagen and Reticulin, Histochemistry, 1986, 41-49, vol. 85.

Xie et al., Mechano-Active Scaffold Design Based on Microporous Poly(L-lactide-co-ε-caprolactone) for Articular Cartilage Tissue Engineering: Dependence of Porosity on Compression Force-Applied Mechanical Behaviors, Tissue Engineering Part A, 2006, 449-458, vol. 12, No. 3.

Yang et al., Electrospinning of Nano / Micro Scale Poly (L-lactic Acid) Aligned Fibers and their Potential in Neural Tissue Engineering, Biomaterials, 2005, 2603-2610, vol. 26.

Yasui et al., Tomographic Imaging of Collagen Fiber Orientation in Human Tissue Using Depth-Resolved Polarimetry of Second-Harmonic-Generation, Light, Optical and Quantum Electronics, 2005, 1397-1408, vol. 37.

Zhao et al., Directed Migration of Corneal Epithelial Sheets in Physiological Electric Fields, Investigative Opthalmology & Visual Science, Dec. 1996, 2548-2558, vol. 37, No. 13.

Zhou et al., The ABC Transporter Bcrp1/ABCG2 is Expressed in a Wide Variety of Stem Cells and is a Molecular Determinant of the Side-Population Phenotype, Nature Medicine, Sep. 2001, 1028-1034, vol. 7, No. 9.

Zimmermann et al., Type VI Collagen is a Major Component of the Human Cornea, FEBS Letters, Mar. 1986, 55-58, vol. 197, No. 1, 2.

Zipfel et al., Nonlinear Magic: Multiphoton Microscopy in the Biosciences, Nature Biotechnology, Nov. 2003, 1369-1377, vol. 21, No. 11.

Zorlutuna et al., Influence of Keratocytes and Retinal Pigment Epithelial Cells on the Mechanical Properties of Polyester-based Tissue Engineering Micropatterned Films, Biomaterials, 2007, 3489-3496, vol. 28.

Zuk et al., Human Adipose Tissue is a Source of Multipotent Stem Cells, Molecular Biology of the Cell, Dec. 2002, 4279-4295, vol. 13.

Kato et al., "An attempt to construct the stroma of cornea using primary cultured corneal cells," J Nanosci Nanotechnol, 2007, pp. 748-751, vol. 7, No. 3.

Shah et al., "The development of a tissue-engineered cornea: biomaterials and culture methods," Ped. Res. 2008, pp. 535-544, vol. 63, No. 5.

\* cited by examiner

SEQUENCE LISTING

<160> NUMBER OF SEQ ID NOS: 8

<210> SEQ ID NO 1
<211> LENGTH: 20
<212> TYPE: DNA
<213> ORGANISM: Homo sapiens

<400> SEQUENCE: 1
tcctggattc ctttccttca                                              20

<210> SEQ ID NO 2
<211> LENGTH: 20
<212> TYPE: DNA
<213> ORGANISM: Homo sapiens

<400> SEQUENCE: 2
caatcgagga gggcagaata                                              20

<210> SEQ ID NO 3
<211> LENGTH: 20
<212> TYPE: DNA
<213> ORGANISM: Homo sapiens

<400> SEQUENCE: 3
atctgcagca ccttcacctt                                              20

<210> SEQ ID NO 4
<211> LENGTH: 20
<212> TYPE: DNA
<213> ORGANISM: Homo sapiens

<400> SEQUENCE: 4
cattggaatt ggtggtttga                                              20

<210> SEQ ID NO 5
<211> LENGTH: 20
<212> TYPE: DNA
<213> ORGANISM: Homo sapiens

<400> SEQUENCE: 5
cattggcacc tggaactacc                                              20

<210> SEQ ID NO 6
<211> LENGTH: 20
<212> TYPE: DNA
<213> ORGANISM: Homo sapiens

<400> SEQUENCE: 6
ggcttgagga ccactgagtt                                              20

<210> SEQ ID NO 7
<211> LENGTH: 23
<212> TYPE: DNA
<213> ORGANISM: Homo sapiens

<400> SEQUENCE: 7
ccctgtaatt ggaatgagtc cac                                          23

<210> SEQ ID NO 8
<211> LENGTH: 18

```
<212> TYPE: DNA
<213> ORGANISM: Homo sapiens

<400> SEQUENCE: 8
gctggaatta ccgcggct                                              18
```

BIOENGINEERED HUMAN CORNEAL STROMAL TISSUE

CROSS-REFERENCE TO RELATED APPLICATIONS

This application is a National Stage of International Patent Application No. PCT/US2011/027195, filed Mar. 4, 2011, which claims the benefit under 35 U.S.C. §119(e) of U.S. Provisional Application No. 61/310,559, filed Mar. 4, 2010, which is incorporated herein by reference in its entirety.

STATEMENT REGARDING FEDERALLY-SPONSORED RESEARCH AND DEVELOPMENT

This invention was made with government support under Grant No. EY016415 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 6527_122715_ST25.txt. The size of the text file is 1,610 Bytes, and the text file was created on Aug. 28, 2012.

Provided herein are compositions and devices, and in particular, biodegradable scaffolds useful in the preparation of bioengineered corneal tissue. Also provided herein are methods of making and using the scaffolds.

The appropriate functionality of any organ and tissue in human body relies on the complex structural organization of cells and extracellular matrix (ECM). ECM, featuring the special three-dimensional(3D) structures, renders organs and tissues mechanical functions. More importantly, ECM provides the micro-environment to guide the cellular activities, including cell spreading, migration, proliferation and differentiation, mainly due to that cells are sensitive to surface topology, molecular composition, and mechanical properties of the matrix. To mimic native cellular microenvironments is pivotal to control the cell-matrix interaction and recapitulate tissue architecture in tissue engineering. Collagen is the most abundant protein found in animal connective tissue. It is the main structural components comprising ECM to maintain the shape and integrity of tissues, and impart mechanical strength. Although in part tissue-specific, collagens are preferably aligned in constitute human tissues, including compact bone, tendons and ligaments, articular cartilage, among others. In the corneal stroma, hybrid type-I/V collagen fibrils form a spatially organized pseudo hexagonal lattice, in which the uniform diameter and spacing of collagen fibrils are 30.8 nm and 55.3 nm, respectively (Meek, K. M., et al. *Biophys. J.* 1993, 64, 273-280 and Meek, K. M., et al. *Exp. Eye Res.* 2004, 78, 503-512). The alignment of collagen fibers of consecutive lamellae is perpendicular to each other, resulting in a transparent lens capable of resisting external trauma and supporting intraocular pressure. Once the corneal stroma is injured, quiescent keratocytes residing within the stroma are activated to differentiate into myofibroblasts, which secrete altered disorganized collagenous matrix, resulting in stromal scar formation and reduced transparency. Clearly, to constitute the aligned collagen-based ECM with nano-scale spatial organization is critical to succeed in repair and regeneration of the damaged and diseased corneal stroma tissue.

Although it is very challenging to create three-dimensional (3D) orderly collagen-fibril construct, its importance in tissue engineering has attracted more and more attention of biomaterial scientists to develop methods to align collagen in vitro. Contact guidance is the simple and effective approach to provide the physical cue to direct cell orientation and organization of cell-secreted collagens. Recently, Guillemette et al. found micro-patterned surfaces can guide the cells to align along the grooves, leading to cell-secreted collagens to organize along cell orientation (*Integr Biol (Camb)* 2009, 1, 196-204). Interestingly, the subsequent organization of cells and cell-secreted collagens is cell-type specific following the alignment of the first layer of cells and cell-secreted collagen. In contrast to dermal fibroblasts, corneal fibroblast do not lose the alignment from the second layer. However, transmission electron micrographs (TEM) reveal that the collagen fibrils in the construct is diameter-polydispersed, and lack long-range order. Clearly, not only the tissue origin of the cells, but also the cell phenotype plays the crucial role in the nanoscale spatial organization of cell-secreted collagen fibrils.

Keratocytes are the inborn cell population in human corneal stroma, responsible for secreting a spectrum of unique matrix molecules, e.g. keratocan and keratan sulfate, that constitute the transparent stroma tissue, a well-organized collagen-based 3-dimensional nano-construct. When attempts are made to expand keratocyte populations in culture in serum-based medium, the keratocytes inevitably lose their phenotype and differentiate into fibroblasts, leading to the formation of scar tissue. Accordingly, there is a need of a population of progenitor cells which can be expanded in culture, and then differentiated into keratocytes that retain the ability to produce an appropriate extracellular matrix. Thus, there is a need for biodegradable materials that combine the favorable bioactive and biocompatible properties of naturally-occurring scaffold materials with the reproducible and predictable properties of synthetic scaffold materials. There is also a need for biocompatible and biodegradable materials that are useful for promoting wound and tissue healing that possess bioactive components, and that exhibit mechanical properties similar to native tissue.

SUMMARY

Provided herein are template scaffolds that are useful in preparing a suitable bioscaffold for implantation in the human cornea. The scaffold materials produced by the methods described herein and using the materials described herein can be implanted in a patient's cornea either to correct refractive defects, such as presbyopia, hyperopia, myopia and astigmatism, or as a replacement of scarred or otherwise damaged or defective stromal tissue.

In one embodiment, a method is provided for producing a bioscaffold for implantation in the cornea of a patient, for instance as a corneal inlay or onlay. The method comprises culturing functional keratocytes on a scaffold template comprising one or more layers comprising aligned (that is a predominance of fibers in the layer are substantially parallel to each other, such as are formed by electrospinning techniques as described herein) fibers of a biocompatible, biodegradable polymeric composition that is optionally elastomeric, where when more than one layer is present in a plurality of layers, the fibers of two or more layers, such as adjacent layers, are aligned at different angles, and in one embodiment at 20° to 90°, including increments therebetween, and in one embodiment, at 45° or perpendicular (orthogonally) to each other. The functional keratocytes are cultured on the scaffold for a length of time sufficient for the cells to produce an aligned and preferably transparent product ECM scaffold, which substantially replaces the biocompatible, biodegradable polymeric composition. The ECM scaffold is then optionally processed into a defined shape, such as a disc for corneal inlay or onlay, if the original scaffold is not an appropriate size or shape for its intended end-use. In one embodiment, the construct thus produced is implanted into the eye of a patient. In one embodiment, the produced construct is decellularized prior to implantation. When implanted in the eye of a patient, the decellularized scaffold is populated with native cells. The implantation can be an onlay, an inlay or can replace native stromal tissue either in part or wholly.

In one embodiment of the described method, the functional keratocytes are produced by differentiation of progenitor cells, e.g., stem cells (multipotent cells), capable of differentiating into the functional keratocytes by culturing in a keratocyte differentiation medium. The stem cells can be any stem cell able to differentiate into functional keratocytes that produce collagen, keratan sulfate and keratocan. Examples of suitable stem cells are corneal stromal stem cells and adipose-derived stem cells, and in one embodiment, human corneal stromal stem cells and human adipose-derived stem cells. In one preferred embodiment, the stem cells are human corneal stromal stem cells.

In another embodiment, a bioscaffold template is provided comprising one or more layers comprising aligned fibers of a biocompatible, biodegradable polymeric composition that is optionally elastomeric, where when more than one layer is present in a plurality of layers, the fibers of two or more layers, such as adjacent layers, are aligned at different angles, and in one embodiment at 20° to 90°, including increments therebetween, and in one embodiment, at 45° or perpendicular (orthogonally) to each other. Adipose or corneal stem cells are dispersed within the template scaffold. In yet another embodiment, a bioreactor is provided comprising the template scaffold in a culture vessel comprising keratocyte differentiation medium.

Material that is useful in preparing the scaffolds and cell constructs described herein are biodegradable and biocompatible, including polyesters and polyurethanes comprising hydrophilic groups, such as ether and ester groups.

As used herein, the terms "comprising," "comprise" or "comprised," and variations thereof, in reference to elements of an item, composition, apparatus, method, process, system, etc. are meant to be open-ended, indicating that the item, composition, apparatus, method, process, system, etc. includes those elements and that other elements can be included and still fall within the scope/definition of the described item, composition, apparatus, method, process, system, etc.

The scaffold may comprise a therapeutic agent. For example and without limitation, the therapeutic agent may be an antimicrobial agent chosen from one or more of: isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate. Optionally, the therapeutic agent may be a growth factor, for example and without limitation, a growth factor chosen from one or more of: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. The thereapeutic agent may be cellular, for example and without limitation one or more of stem cells, precursor stem cells, smooth muscle cells, skeletal myoblasts, myocardial cells, endothelial cells, and genetically modified cells.

The template scaffold can be prepared by any useful method, such as, without limitation, by casting or electrospinning, including combinations thereof. In a useful electrospinning method, the synthetic polymeric component and a biological polymeric component can be suspended independently or together in a solvent and may therefore be spun together or independently (using, for example two nozzles) to form an scaffold.

Methods of promoting wound healing or tissue generation or regeneration in a patient also are provided. The methods comprise, without limitation, implanting an scaffold as described herein at or near a site for wound healing or tissue generation or regeneration in the patient. Likewise a method of promoting wound healing or tissue generation or regeneration in a patient is provided comprising contacting an scaffold as described herein with cells in vitro (for instance, ex vivo for autologous cells), culturing the cells in vitro so that the cells grow in and/or on the scaffold; and implanting the scaffold at or near a site for wound healing or tissue generation or regeneration in the patient. In either method, the scaffold may comprise a therapeutic agent as described herein.

DETAILED DESCRIPTION

Figure 1:
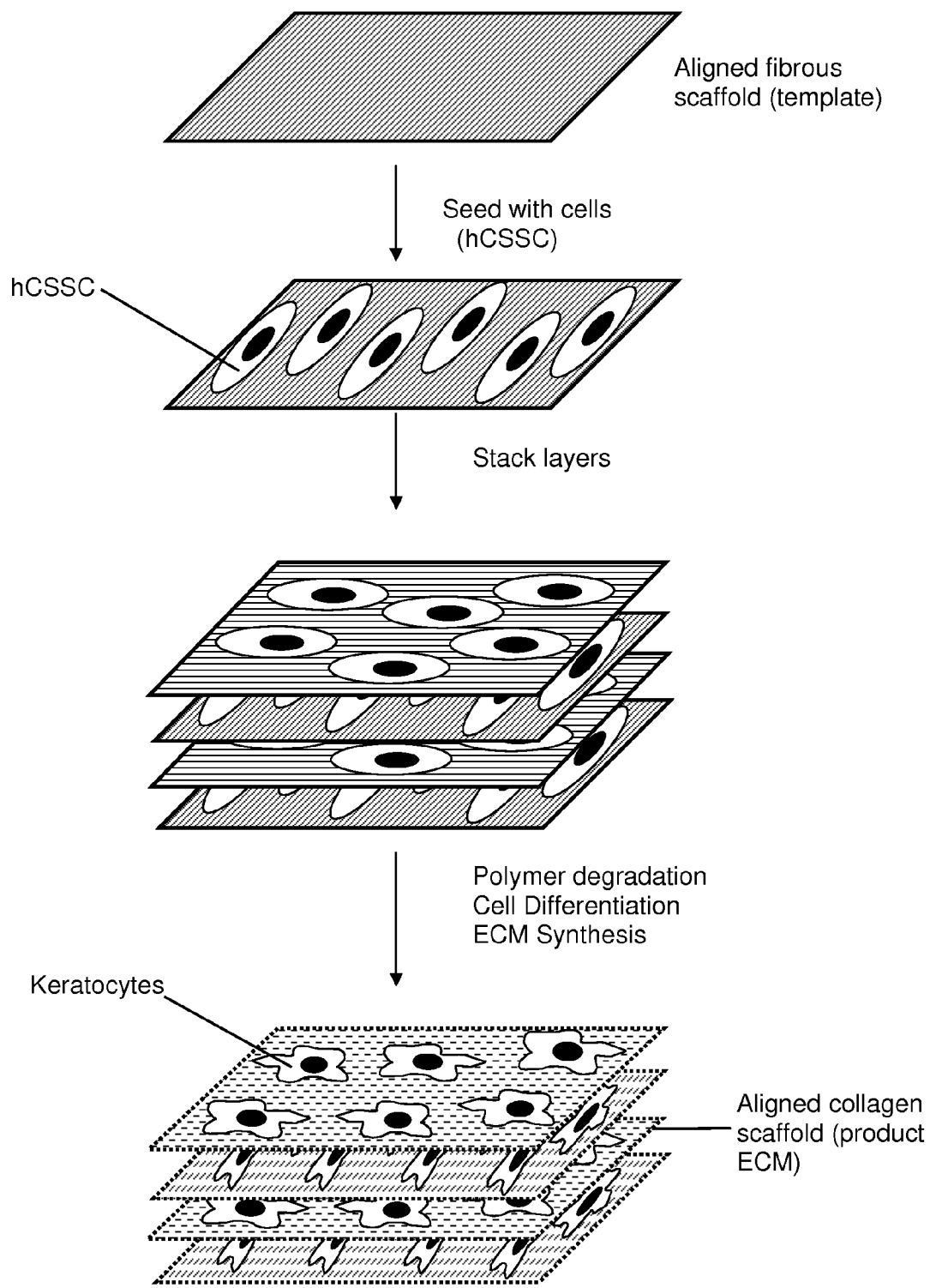
FIG. 1 provides a schematic flow diagram illustrating a method of making an ECM scaffold for cornea implantation.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. "A," "an," and "one" include the plural unless indicated otherwise.

The copolymers, compositions and components thereof are preferably biocompatible. By "biocompatible," it is meant that a polymer composition and its normal in vivo degradation products are cytocompatible and are substantially non-toxic and non-carcinogenic in a patient within useful, practical and/or acceptable tolerances. By "cytocompatible," it is meant that the copolymers or compositions are substantially non-toxic to cells and typically and most desirably can sustain a population of cells and/or the polymer compositions, devices, copolymers, and degradation products thereof are not cytotoxic and/or carcinogenic within useful, practical and/or acceptable tolerances. For example, a copolymer composition when placed in a human cornea stem cell culture does not adversely affect the viability, growth, adhesion, and number of cells. In one non-limiting example, the co-polymers, compositions, and/or devices are "biocompatible" to the extent they are acceptable for use in a human veterinary patient according to applicable regulatory standards in a given legal jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues organs or the organism from the implanted compositions.

As used herein, a "polymer" is a compound formed by the covalent joining of smaller molecules, which are referred to herein as residues, or polymer subunits, when incorporated into a polymer. A "copolymer" is a polymer comprising two or more different residues. Prior to incorporation into a polymer, the residues typically are described as monomers. Non-limiting examples of monomers, in the context of acrylic/polyester copolymers described herein, include: acrylic or acrylamide monomers, such as acrylic acid, isopropylacrylamide, acrylamide, acrylic N-hydroxysuccinimide ester and hydroxyethyl methacrylate, lactide, and trimethylene carbonate. A monomer may be a macromer prepared from even smaller monomers, such as a hydroxyethyl methacrylate-polylactide (HEMAPLA) macromer or hydroxyethyl methacrylate-poly(trimethylene carbonate) (HEMAPTMC) macromer.

The biological scaffolds described herein can be used for a large number of medical applications including, but not limited to refractive surgery to alter the refractivity of the cornea and to repair or replace corneal stroma.

FIG. 1 shows a general outline of a method described herein. In the method, stem cells are seeded onto a scaffold in which polymer fibers are aligned and preferably allowed to adhere to and optionally propagate on the single sheet. The seeded sheets are then stacked at different angles, meaning the orientation of the fibers of adjacent sheets are different (that is, non-parallel) to each-other. Though FIG. 1 shows an orthogonal arrangement, the sheets can be oriented at any angle with respect to each other that is not 0°. As would be recognized by one of ordinary skill a perfectly perpendicular arrangement or arrangement at any specified angle is not necessarily achievable or practicable, nor is perfect alignment of the fibers within a sheet. Therefore, the orthogonal or perpendicular (90°) arrangement, or any angle, includes some acceptable deviation from stated angle and include orientations that are essentially at that angle or substantially at that angle (θ), such as θ±20°, 15°, 10°, 9°, 8°, 7°, 6°, 5°, 4°, 3°, 2° or 1° so long as the scaffold retains its ability to form acceptable product cellular constructs or ECM scaffolds.

At some point, either before the sheets are stacked, or afterwards, the stem cells are differentiated by adding suitable differentiation medium to the culture. As indicated below, for the purpose of producing a product corneal stroma ECM structure, the stem cells are hCSSCs and keratocyte differentiation medium (KDM) is added. Exemplary KDM is described below in the Examples, and is suitable for differentiating hCSSCs to corneal keratocytes, and includes, for example an ascorbate, such as ascorbic acid or ascorbic acid phosphate (e.g. A2P, below) and optionally TGFβ3, insulin and/or basic fibroblast growth factor. Ascorbate is recognized as being able to elicit keratocyte-like matrix production in vitro. It may be desirable also to add TGF-β3, or other growth factors to the medium to culture hCSSCs, ADSCs or other stem cell types.

Once the layers are stacked, the resultant multi-layered scaffold is maintained in culture for a length of time sufficient for the polymeric template scaffold to dissolve or substantially dissolve and for the product ECM scaffold to form.

In an alternate embodiment, the sheets are stacked after the product ECM is produced in a single-layer sheet, either with the cells or after decellularization. Controlled compression can be used to laminate sheets together.

According to one non-limiting embodiment, for each layer of fibers, the fiber diameter ranges from 100 to 200 nm in thickness, with spacing between fibers of less than 1 μm. Each single layers typically range from 5 μm-10 μm in thickness, for example 8 μm on the average. Normal human cornea stroma is about 500 μm in thickness, meaning approximately 50-60 layers would be needed to produce a full-thickness scaffold. Controlled compression can be used to fuse together monolayers oriented, for example, orthogonally on a layer-by-layer basis, or the template scaffold and cells can be alternately electrodeposited and electrosprayed until a desired thickness is achieved. In this case, the polymer composition and cells are not electrospun on a mandrel but can be electrodeposited on a planar surface with alternate grounding electrodes arranged so that alternate layers of fibers are deposited at a desired angle with respect to each other, for instance and without limitation, 90° or 45°.

In one variation of this method, hCSSCs or other stem cells are differentiated prior to seeding into functional keratocytes and the functional keratocytes are seeded onto the template scaffold prior to stacking. The cells are cultured in a KDM.

Once the product ECM scaffold is formed, it may be further processed for implantation. Due to the immune privileged nature of the eye, allogeneic or even xenogeneic cells may be transferred in the product scaffold and can survive within the eye. That said, it may be most desirable to decellularized and sterilize the scaffold prior to implanting the scaffold, as outlined below. The product ECM scaffold is processed into a structure that is suitable for implantation. A large variety of methods may be used to process the shape and thickness of the product ECM scaffold. Circular section may be punched or cut from the material. Multiple layers of varying sized can be stacked and annealed or laminated to provide a thicker construct.

A variety of cells can be used in the methods described herein. In one example, hCSSCs are seeded onto the structure and then are differentiated to produce functional keratocytes. Alternately, the hCSSCs are pre-differentiated in a KDM and then are seeded onto the structure. As indicated below, the readily-available ADSCs are promising candidates for seeding and later differentiation into functional keratocytes. Because the cells are used to form the ECM, but are not necessarily required to be implanted in the eye, xenogeneic corneal stroma stem cells may be used, and may be preferable to hCSSCs, given product ECM scaffolding produced by CSSCs of other species may prove to be equally or more suitable for the purposes described herein than human. Likewise, stem cells from other human organs or tissue, or from other species may prove to be acceptable in the uses described herein, as is the case with ADSCs. hCSSCs may be prepared according to the methods described below. Non-human hCSSCs have been cultured and, for example, can be isolated and propagated according to the same or similar methods. Adipose-derived stem cells ADSCs, can be prepared by any useful method, including that shown below. U.S. Pat. Nos. 6,777,231 and 7,470,537, each of which is incorporated herein by reference in its entirety, describe adipose-derived stem cells and methods of making adipose-derived stem cells.

As used herein, a progenitor cell is a cell type in a cell lineage that can differentiate into another cell type in that lineage. Corneal stromal stem cells isolated substantially according to the methods described herein can be identified by expression of ABCG2 and have the ability to differentiate into functional keratocytes in keratocyte differentiation media as described in the examples below.

As used herein, the term "polymer" refers to both synthetic polymeric components and biological polymeric components. "Biological polymer(s)" are polymers that can be obtained from biological sources, such as, without limitation, mammalian or vertebrate tissue, as in the case of certain extracellular matrix-derived (ECM-derived) compositions. Biological polymers can be modified by additional processing steps. Polymer(s), in general include, for example and without limitation, mono-polymer(s), copolymer(s), polymeric blend(s), block polymer(s), block copolymer(s), cross-linked polymer(s), non-cross-linked polymer(s), linear-, branched-, comb-, star-, and/or dendrite-shaped polymer(s), where polymer(s) can be formed into any useful form, for example and without limitation, a hydrogel, a porous mesh, a fiber, woven mesh, or non-woven mesh, such as, for example and without limitation, as a non-woven mesh formed by electrospinning.

Generally, the polymeric components suitable for preparation of the template scaffold described herein may be any polymer that is biocompatible and is either biodegradable or has a Lower Critical Solution Temperature (LCST) lower than 37° C. so that the polymer is dissolved by cooling the scaffold below cell culture temperatures. By "biodegradable," it is meant that a polymer, once implanted and placed in contact with bodily fluids and/or tissues, will degrade either partially or completely through chemical, biochemical and/or enzymatic processes. Non-limiting examples of such chemical reactions include acid/base reactions, hydrolysis reactions, and enzymatic cleavage. In certain non-limiting embodiments, the biodegradable polymers may comprise homopolymers, copolymers, and/or polymeric blends comprising, without limitation, one or more of the following monomers: glycolide, lactide, caprolactone, dioxanone, and trimethylene carbonate. In other non-limiting embodiments, the polymer(s) comprise labile chemical moieties, non-limiting examples of which include esters, ethers, anhydrides, polyanhydrides, or amides, which can be useful in, for example and without limitation, controlling the degradation rate of the scaffold and/or the release rate of therapeutic agents from the scaffold. Alternatively, the polymer(s) may contain peptides or biomacromolecules as building blocks which are susceptible to chemical reactions once placed in situ. In one non-limiting example, the polymer is a polypeptide comprising the amino acid sequence alanine-alanine-lysine, which confers enzymatic lability to the polymer.

The polymer components may be selected so that they degrade in situ on a timescale that is similar to an expected rate of production of ECM scaffold by the cells seeded onto the template scaffold. Polyesters and polyurethanes that incorporate hydrophilic groups such as ester or ether groups are examples of polymer compositions that would degrade over time. Examples of suitable polyesters include polylactic acid (PLA), polyglycolides (polyglycolic acid, PGA), polycaprolactone (PCL), polydioxanone, polyhydroxyalkanoates (PHA), poly(lactic-co-glycolic acid) (PLGA), etc. Non-limiting examples of useful in situ degradation rates include between one week and one year or increments therebetween for instance, between one week and 10 months, and between one month and six month. In the context of the present disclosure, it is desirable that the synthetic polymer components degrade within one month, or less, so that aligned collagen and other ECM constituents replace the original polymeric components as rapidly as possible.

The polymeric components used to make the scaffold are biocompatible. By "biocompatible," it is meant that a polymer compositions and its normal degradation in vivo products are cytocompatible and are substantially non-toxic and non-carcinogenic in a patient within useful, practical and/or acceptable tolerances. By "cytocompatible," it is meant that the polymer can sustain a population of cells and/or the polymer composition, device, and degradation products, thereof are not cytotoxic and/or carcinogenic within useful, practical and/or acceptable tolerances. For example, the polymer when placed in a human cornea stem cell or functional keratocyte cell culture does not adversely affect the viability, growth, adhesion, and number of cells. In one non-limiting embodiment, the compositions, and/or devices are "biocompatible" to the extent they are acceptable for use in a human veterinary patient according to applicable regulatory standards in a given jurisdiction. In another example the biocompatible polymer, when implanted in a patient, does not cause a substantial adverse reaction or substantial harm to cells and tissues in the body, for instance, the polymer composition or device does not cause necrosis or an infection resulting in harm to tissues from the implanted scaffold. In the context of the present application, the original polymer composition is typically completely or substantially degraded when implanted.

The mechanical properties of a biodegradable scaffold can be optimized to mimic native tissue at the site of implantation. In certain non-limiting embodiments, the mechanical properties of the scaffold are optimized similar to or identical to that of native soft tissue, such as fascia, connective tissue, blood vessel, muscle, tendon, fat, etc. In one non-limiting embodiment, the biodegradable scaffold comprises a thermoplastic polymer. The mechanical properties of the scaffold also may be optimized to be suitable for surgical handling. In one non-limiting embodiment, the scaffold is flexible. In another, the scaffold is foldable and can be delivered to the site by minimally invasive methods.

The physical and/or mechanical properties of the biodegradable scaffold can be optimized by any useful method. Because the polymer compositions are deposited by electrodeposition, more typically by electrospinning, the polymer structure is optimized for that application. Variables that can be optimized include without limitation, the extent of physical cross-linking in a network comprising polymeric components, the ratio of polymeric components within the network, the distribution of molecular weight of the polymeric components, and the method of processing the polymers. Polymers are typically semicrystalline and their physical properties and/or morphology are dependent upon a large number of factors, including monomer composition, polydispersity, average molecular weight, cross-linking, and melting/crystallization conditions. For example, flow and/or shear conditions during cooling or electrodeposition of a polymer melt are known to affect formation of crystalline structures in the composition. In one non-limiting embodiment, the scaffold comprises a polymeric component that provides strength and durability to the scaffold, yet is so that the mechanical properties of the scaffold are similar to the native tissue surrounding the wound or site in need of tissue regeneration.

The polymeric component can be any useful biocompatible, biodegradable and synthetic polymer material. In certain non-limiting embodiments, the synthetic polymeric component comprises a thermoplastic biodegradable elastomer. In another the polymeric component comprises a phase-separated biodegradable elastomer with degradable soft and/or hard segments. In yet another non-limiting embodiment, the synthetic polymeric component comprises any hydrolytically, chemically, biochemically, and/or proteolytically labile group, non-limiting examples of which include an ester moiety, amide moiety, anhydride moiety, specific peptide sequences, and generic peptide sequences.

In certain non-limiting embodiments, the polymeric component is a biodegradable polyurethane polymer. In one example, the synthetic polymeric component is a linear segmented poly(urethane urea) copolymer, where the copolymer comprises alternating blocks of "soft" and "hard" segments. In one non-limiting embodiment, the soft segment is a polyether or polyester (e.g., polycaprolactone), which may have a glass transition temperature (temperature at which a reversible change occurs in an amorphous material, such as glass or an amorphous polymer, or in amorphous portions of a partially crystalline polymer from, or to, a viscous or rubbery condition to a hard or relatively brittle one) below the use temperature. As used herein, the "use temperature" or like phrases refers to the temperature at which the scaffolding is maintained after implantation, namely the body temperature of a patient, such as 37° C. for a human patient or typical cell culture.

In another non-limiting embodiment, the soft segment comprises a multiblock copolymer in which one or more segments are polyester. In one non-limiting embodiment, a pre-polymer is formed by reacting butyl diisocyanate with polycaprolactone diol and then further reacting the pre-polymer with a chain extender, such as butyl diamine and specific peptide sequences (e.g., alanine-alanine-lysine).

The polymeric component can be prepared by any useful method. According to one non-limiting embodiment, the polymeric component comprises a biodegradable polymeric portion, an isocyanate derivative, and a diamine chain extender. In one non-limiting example, formation of the polymeric component comprises at least two steps. In the first step, a pre-polymer is formed, for example in one non-limiting embodiment, the pre-polymer comprises an isocyanate-terminated polymer, which is formed by reacting a biodegradable polymer with an isocyanate derivative. In the second step, the pre-polymer can be further reacted to form chemical bonds between pre-polymer molecules. For example, the isocyanate-terminated pre-polymer is reacted with a diamine chain extender, which reacts with the isocyanate moiety to form chemical bonds between pre-polymer molecules. In another non-limiting example, the isocyanate-terminated pre-polymer is reacted with a diol chain extender, which reacts with the isocyanate moiety. As used herein, an "isocyanate derivative" is any molecule or group that is terminated by the moiety —N=C=O. Isocyanate derivates also include, without limitation, monoisocyanates and polyisocyanates, such as diisocyanates and triisocyanates. In one non-limiting embodiment, the isocyanate derivative is 1,4-diisocyanatobutane.

Preparation of polymeric components may include other steps, including, for example and without limitation, catalytic steps, purification steps, and separation steps. The polymeric component described herein comprises one or more biodegradable, biocompatible polymers. The biodegradable polymers may be, without limitation, homopolymers, copolymers, and/or polymeric blends. The polymer(s) may comprise, without limitation, one or more of the following monomers: glycolide, lactide, caprolactone, dioxanone, and trimethylene carbonate. In one non-limiting embodiment, the polymer comprises a polycaprolactone. In another embodiment, the polymer comprises a polycaprolactone diol. In yet another embodiment, the polymer comprises a triblock copolymer comprising polycaprolactone, poly(ethylene glycol), and polycaprolactone blocks.

As used herein, a "chain extender" is any molecule or group that reacts with an active group, such as, without limitation, an isocyanate derivative, to extend chains of polymers. Non-limiting examples of useful chain extenders are diamines and diols. In one non-limiting embodiment, the chain extender is a diamine that allows for extending the chain of the pre-polymer, such as putrescine (1,4-diaminobutane). In another non-limiting embodiment, the diamine is lysine ethyl ester. In yet another non-limiting embodiment, the diamine is a peptide fragment comprising two or more amino acids, for example and without limitation, the peptide fragment alanine-alanine-lysine, which can be cleaved enzymatically by elastase. In one non-limiting embodiment, the chain extender is a diol that allows for extending the chain of the pre-polymer, such as 1,4-butane diol.

In one non-limiting embodiment, the polymeric component comprises a biodegradable poly(ester urethane) urea elastomer (PEUU). One non-limiting example of a PEUU is an polymer made from polycaprolactone diol (MW 2000) and 1,4-diisocyanatobutane, using a diamine chain extender, such as putrescine. The PEUU copolymer can be prepared by a two-step polymerization process whereby polycaprolactone diol (MW 2000), 1,4-diisocyanatobutane, and diamine are combined in a 2:1:1 molar ratio. In the first step, to form the pre-polymer, a 15 wt % solution of 1,4-diisocyanatobutane in DMSO (dimethyl sulfoxide) is stirred continuously with a 25 wt % solution of polycaprolactone diol in DMSO. Then, stannous octoate is added and the mixture is allowed to react at 75° C. for 3 hours. In the second step, the pre-polymer is reacted with a diamine to extend the chain and to form the polymer. For example and without limitation, the diamine putrescine is added dropwise while stirring and allowed to react at room temperature for 18 hours. In another non-limiting embodiment, the diamine is lysine ethyl ester, which is dissolved in DMSO with triethylamine, added to the pre-polymer solution, and allowed to react at 75° C. for 18 hours. After the two step polymerization process, the polymer solution is precipitated in distilled water. Then, the wet polymer is immersed in isopropanol for three days to remove any unreacted monomers. Finally, the polymer is dried under vacuum at 50° C. for 24 hours.

In another non-limiting embodiment, the polymeric component comprises a poly(ether ester urethane) urea elastomer (PEEUU). In one non-limiting example, the PEEUU is made by reacting polycaprolactone-b-polyethylene glycol-b-polycaprolactone triblock copolymers with 1,4-diisocyanatobutane and putrescine. PEEUU may be obtained, for example and without limitation, by a two-step reaction using a 2:1:1 reactant stoichiometry of 1,4-diisocyanatobutane:triblock copolymer:putrescine. In a further non-limiting example, the triblock polymer is prepared by reacting poly(ethylene glycol) and s-caprolactone with stannous octoate at 120° C. for 24 hours under a nitrogen environment. The triblock copolymer may be washed with ethyl ether and hexane, then dried in a vacuum oven at 50° C. In the first step to form the pre-polymer, a 15 wt % solution of 1,4-diisocyanatobutane in DMSO is stirred continuously with a 25 wt % solution of triblock copolymer in DMSO. Stannous octoate is then added and the mixture is allowed to react at 75° C. for 3 hours. In the second step, putrescine is added drop-wise under stiffing to the pre-polymer solution and allowed to react at room temperature for 18 hours. The PEEUU polymer solution is then precipitated with distilled water. The wet polymer is immersed in isopropanol for 3 days to remove unreacted monomer and dried under vacuum at 50° C. for 24 hours.

In another non-limiting embodiment, the polymer composition has a Lower Critical Solution Temperature (LCST) below 37° C. such that the polymer structure solubilized at temperatures below cell culture temperatures. This facilitates removal of the original copolymer in favor of the aligned collagen scaffold formed by the corneal keratocytes. The LCST may preferably be between 20° C. and 35° C. in order to minimally affect ECM structures formed by the cells in culture, but the In one example, the polymer composition comprises pNIPAAM (poly N-isopropyl acrylamide).

As described in U.S. Pat. No. 5,262,055, incorporated herein by reference in its entirety, thermosensitive polymers may be made up of monomers or mixtures of such monomers polymerizable by free radical or ionic initiation which results in polymers having LCST in aqueous systems between 15° C. and 35° C. Suitable are the N-alkyl or N,N-dialkyl substituted acrylamides or methacrylamides of the formula:

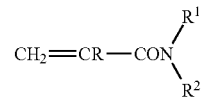

where R is hydrogen or methyl, $R^1$ is a member selected from the group consisting of lower alkyl and lower alkoxyalkyl and $R^2$ is a member selected from the group consisting of hydrogen, lower alkyl and lower alkoxyalkyl with the proviso that $R^1$ and $R^2$ can combine as an alkylene —$(CH_2)_n$— chain to form a N-cyclic structure where n is an integer of 4 to 6. n is preferably 5. By lower alkyl or alkoxy is meant a straight or branched carbon chain containing from one to eight carbon atoms and preferably from one to five carbon atoms. Mixtures of one or more of the above monomers may also be utilized as temperature sensitive components.

Examples of such temperature sensitive monomers are those selected from the group consisting of N-isopropylacrylamide ["NiPAAm"], N,N-diethylacrylamide, N-acryloylpiperidine, N-methylmethacrylamide, N-ethylmethacrylamide, N-n-propylacrylamide and N-(3'-methoxypropyl) acrylamide. The preferred temperature sensitive monomers are the lower alkyl acrylamides which are selected from the group consisting of N-isopropylacrylamide, N,N-diethylacrylamide and N-n-propylacrylamide.

United States Patent Publication No. 20080096975 A1, incorporated herein by reference for its technical disclosure, describes a useful copolymer comprising poly NIPAAM, n-hydroxyl succinimide, acrylic acid and a polyester macromer. According to one embodiment, the copolymer comprises an N-isopropylacrylamide residue (an N-isopropylacrylamide monomer incorporated into a polymer), one or both of an acrylic acid residue and a methacrylic acid residue and an acrylic residue having an amine-reactive group. The copolymer comprises a polyester linkage in its backbone. According to one non-limiting embodiment, the copolymer is prepared from at least five components: N-isopropylacrylamide or an N-alkyl acrylamide in which the alkyl is methyl, ethyl, propyl, isopropyl or cyclopropyl, acrylic acid and/or methacrylic acid, an acrylic monomer optionally having an amine-reactive group (such as acrylic N-hydroxysuccinimide ester) and a polyester macromer. For example and without limitation, the polyester macromer is a polylactide macromer, comprising hydroxyethyl methacrylate residues and varying numbers of lactide units/residues. In another non-limiting example, the polyester macromer is a poly(trimethylene carbonate macromer), comprising hydroxyethyl methacrylate residues and varying numbers of trimethylene carbonate units/residues. Each component contributes to the desired physical properties of the hydrogel to form a distinct structure at a higher temperature and to solubilize at a lower temperature below the LCST of the composition. The amine-reactive component of the copolymer (for instance, acrylic N-hydroxysuccinimide ester) binds to amine-containing compounds including bioactive or biocompatible materials or factors. The composition of each component in the hydrogel determines the lower critical solution temperature (LCST) of the hydrogel. At a temperature less than the LCST, the hydrogel flows easily and can be injected into the desired shape. When the temperature is increased above the LCST, the hydrogel solidifies and retains the shape. Once solidified, the hydrogel is highly flexible and relatively strong at physiological temperature.

According to one embodiment, polyester component within the macromer introduces the degradability and hydrophobicity of the copolymer. For complete removal of the copolymer, the copolymer includes hydrolytically-cleavable bonds that results in soluble, non-toxic by-products, even above the LCST of the non-degraded copolymer. Once the copolymer is degraded, the LCST is above physiological temperature, which results in dissolution of the degraded hydrogel and clearance of the degraded components.

To facilitate the hydrolysis of the copolymer, according to one embodiment, the backbone of the polymer comprises biodegradable ester linkages, for example and without limitation, from 1% to 10% of the linkages of the copolymer backbone. The polymer may comprise a polyester macromer, for example and without limitation, a polyester macromer comprising hydroxyethyl methacrylate and lactide residues. In one embodiment, the ratio of hydroxyethyl methacrylate and lactide residues in the polyester macromer is from 1:2 to 1:8, in another, from 1:1 to 1:10, such as 1:1, 1:2, 1:3, 1:4, 1:5, 1:6, 1:7, 1:8, 1:9, and 1:10. In another non-limiting example, the polyester macromer comprises hydroxyethyl methacrylate and trimethylene carbonate residues. In one embodiment, the ratio of hydroxyethyl methacrylate and trimethylene carbonate residues in the polyester macromer ranges from 1:1 to 1:10, 1:2 to 1:5 or any increment within those ranges, including 1:1, 1:2, 1:3, 1:4, 1:4.2, 1:5, 1:6, 1:7, 1:8, 1:9, and 1:10. Table 1 provides exemplary structures (excerpted from United States Patent Publication No. 20080096975 A1)

TABLE 1

Composition of Poly(NIPAAm-co-NHS-co-AAc-co-HEMAPLA)

| Polymer | Feed ratio | Composition* |
|---|---|---|
| P(NIPAAm-co-AAc-co-NHS-co-HEMAPLA2.1**) | 85/6/5/4 | 85/6.7/3.9/4.4 |
| P(NIPAAm-co-AAc-co-NHS-co-HEMAPLA3.9**) | 85/6/5/4 | 85/6.9/4.0/4.1 |
| P(NIPAAm-co-AAc-co-NHS-co-HEMAPLA7.0**) | 85/6/5/4 | 85/6.9/3.8/4.3 |
| P(NIPAAm-co-AAc-co-NHS-co-HEMAPLA2.1**) | 80/6/5/9 | 80/7.5/4.2/8.3 |
| P(NIPAAm-co-AAc-co-NHS-co-HEMAPLA3.9**) | 80/6/5/9 | 80/7.0/4.4/8.6 |
| P(NIPAAm-co-AAc-co-NHS-co-HEMAPLA2.1**) | 75/6/5/14 | 75/7.3/4.7/13.0 |
| P(NIPAAm-co-AAc-co-NHS-co-HEMAPLA3.9**) | 75/6/5/14 | 75/6.3/4.9/13.8 |
| P(NIPAAm-co-AAc-co-NHS-co-HEMAPLA2.1**) | 80/11/5/4 | 80/11.4/4.2/4.4 |
| P(NIPAAm-co-AAc-co-NHS-co-HEMAPLA3.9**) | 80/11/5/4 | 80/10.6/6.2/3.2 |

*Determined by H1-NMR.
**Lactide units

In general, the aligned, biodegradable scaffold described herein may be made using any useful method, including one to the many common processes known in the polymer and textile arts. Any method of forming aligned polymeric fibers may be used to prepare the structures described herein. Spinnerette and extrusion methods such as wet, dry, melt and gel spinning may be used, depending on the physical properties of the polymer composition. Electrodeposition is one useful method of preparing small fibers useful in producing biological scaffolds. Aligned fibers may be formed by electrospinning, a modification of the electrodeposition method.

In other non-limiting embodiments, electrospinning is used to fabricate the scaffold. The process of electrospinning involves placing a polymer-containing fluid (for example, a polymer solution, a polymer suspension, or a polymer melt) in a reservoir equipped with a small orifice, such as a needle or pipette tip and a metering pump. One electrode of a high voltage source is also placed in electrical contact with the polymer-containing fluid or orifice, while the other electrode is placed in electrical contact with a target (such as a collector screen or rotating mandrel). During electrospinning, the polymer-containing fluid is charged by the application of high voltage to the solution or orifice (for example, about 3-15 kV) and then forced through the small orifice by the metering pump that provides steady flow. While the polymer-containing fluid at the orifice normally would have a hemispherical shape due to surface tension, the application of the high voltage causes the otherwise hemispherically shaped polymer-containing fluid at the orifice to elongate to form a conical shape known as a Taylor cone. With sufficiently high voltage applied to the polymer-containing fluid and/or orifice, the repulsive electrostatic force of the charged polymer-containing fluid overcomes the surface tension and a charged jet of fluid is ejected from the tip of the Taylor cone and accelerated towards the target, which typically is biased between −2 to −10 kV. Optionally, a focusing ring with an applied bias (for example, 1-10 kV) can be used to direct the trajectory of the charged jet of polymer-containing fluid. As the charged jet of fluid travels towards the biased target, it undergoes a complicated whipping and bending motion. If the fluid is a polymer solution or suspension, the solvent typically evaporates during mid-flight, leaving behind a polymer fiber on the biased target. If the fluid is a polymer melt, the molten polymer cools and solidifies in mid-flight and is collected as a polymer fiber on the biased target. As the polymer fibers accumulate on the biased target, a non-woven, porous mesh is formed on the biased target.

The properties of the electrospun scaffolds can be tailored by varying the electrospinning conditions. For example, when the biased target is relatively close to the orifice, the resulting electrospun mesh tends to contain unevenly thick fibers, such that some areas of the fiber have a "bead-like" appearance. However, as the biased target is moved further away from the orifice, the fibers of the non-woven mesh tend to be more uniform in thickness. Moreover, the biased target can be moved relative to the orifice. In certain non-limiting embodiments, the biased target is moved back and forth in a regular, periodic fashion, such that fibers of the non-woven mesh are substantially parallel to each other (aligned). When this is the case, the resulting non-woven mesh may have a higher resistance to strain in the direction parallel to the fibers, compared to the direction perpendicular to the fibers.

The target can also be a rotating mandrel. In this case, the properties of the non-woven mesh may be changed by varying the speed of rotation. The properties of the electrospun scaffold may also be varied by changing the magnitude of the voltages applied to the electrospinning system. In one non-limiting embodiment, the electrospinning apparatus includes an orifice biased to 12 kV, a target biased to −7 kV, and a focusing ring biased to 3 kV. Moreover, a useful orifice diameter is 0.047" (I.D.) and a useful target distance is about 23 cm.

Other electrospinning conditions that can be varied include, for example and without limitation, the feed rate of the polymer solutions, the distance from the source to the target, the solution concentrations, and the polymer molecular weight. Sheets of aligned polymer fibers are prepared by using a rotating mandrel as a target. The mandrel is not necessarily circular in cross-section (and thus cylindrical), but typically is cylindrical. The mandrel may have any diameter and can be used to prepare sheets having a width that is up to the axial length of the mandrel and a length that is the circumference of the mandrel. Once formed, the aligned fiber sheet can be cut off of the mandrel to form a planar sheet. The thickness of the sheet will depend on the number of turns the polymer fibers make about the mandrel during electrospinning and to some extent the thickness of the fibers.

In order to facilitate continuous formation of multiple layers, as an alternative to electrospinning, the fibers and cells can be electrodeposited layer-by-layer. In this embodiment, the target has alternate grounds arranged such that fibers of each alternate layer are deposited at a different angle, e.g., 90° or 45° with respect to fibers of another layer. In this instance, fibers are deposited in a first orientation using a first ground. Cells are deposited by electrospraying and then fibers are deposited in a second orientation, not parallel to the first orientation using a second ground.

In the Examples below, a PEUU sheet of aligned fibers is formed about a mandrel that is 2 cm long (axial) and 20 cm in diameter. The conditions used to obtain an aligned fiber structure that yielded the best appearance, and therefore was determined best for the experimentation described below was 2000 RPM for a 5% PEUU solution in hexafluoroisopropanol (HFIP). It should be noted that for every different polymer composition, choice of solvent and target, the optimal electrospinning conditions may be obtained by varying target velocity and polymer solution composition to obtain a nonwoven structure with aligned fibers. This is well within the ability of one of ordinary skill in the art. Non-limiting examples of useful range of high-voltage to be applied to the polymer suspension is from 0.5 to 30 kV, from 5 to 25 kV, and from 10 to 15 kV. Useful range of concentrations for the polymeric components include, without limitation, from 1 wt % to 15 wt % including increments therebetween, for example from 4 wt % to 10 wt %, and from 6 wt % to 8 wt %. In the examples below, HFIP is used as a solvent.

A number of other methods exist by which sheets or layers of aligned fibers can be electrodeposited. For example, an electrodeposition device having two, split electrodes may be utilized as described in Li, D., et al. (Electrospinning Nanofibers as Uniaxially Aligned Arrays and Layer-by-Layer Stacked Films, *Adv. Mater.* 2004 16 361).

Cells may be integrated with the scaffold using a variety of methods. For example, the scaffold may be submersed in an appropriate medium (a solution capable of maintaining the viability of or supporting growth of the cells) for the cells, and then directly exposed to the cells. The cells are allowed to adhere to the scaffold and optionally proliferate on the surface and interstices of the scaffold. Multiple layers of the scaffold may be stacked, and the cells propagated under suitable culture conditions prior to further processing. From 2 to 200 layers may be stacked, though media may not adequately diffuse among the layers if too many layers are stacked. As such, from 2-20 layers are preferably stacked, including increments therebetween, including 2, 3, 4, 5, 6, 7, 8, 9, 10, 11, 12, 13, 14, 15, 16, 17, 18, 19 and 20 layers. Preferably, for preparation of cornea stromal material, the layers are orthogonally aligned, meaning the fiber orientation in the layers are perpendicular to (including approximately or substantially perpendicular to) the fiber orientation in adjacent layers.

In another embodiment, the cells of interest are dissolved into an appropriate solution (e.g., a growth medium or buffer) and then sprayed onto a biodegradable scaffold while the scaffold is being formed by electrospinning. While pressure spraying (that is, spraying cells from a nozzle under pressure) is contemplated herein, in certain non-limiting embodiments, the cells are electrosprayed onto the non-woven mesh during electrospinning. As described herein, electrospraying involves subjecting a cell-containing solution with an appropriate viscosity and concentration to an electric field sufficient to produce a spray of small charged droplets of solution that contain cells. United States Patent Publication No. 20080109070, incorporated herein by reference in its entirety for its technical disclosure, describes methods of electrospraying cells. These different conditions include spraying alone, spraying onto a target charged at −15 kV, spraying onto a target charged at −15 kV with PEUU electro spinning, electrospraying at 10 kV onto a target charged at −15 kV, and electrospraying at 10 kV onto a target charged at −15 kV with PEUU electrospinning. In contrast to pressurized spraying, electrospraying cells using the methods described herein did not significantly affect cell viability or proliferation. It is preferred that the distance between the polymer composition and mandrel is sufficient, and the relative orientation of the polymer and cell spraying nozzle is such that the cells do not contact polymer solution containing the solvent (e.g. HFIP).

In the context of the present disclosure, the cells to be deposited onto the scaffold are cells that are native to the tissue to be engineered, or precursors thereof (e.g., stem cells). As an example, for preparation of an engineered corneal stroma structure, it is most desirable to deposit cells that are corneal keratocytes, keratocytes that that produce corneal stroma ECM material (such as keratocytes derived from adipose stem cells, or stem cells that differentiate in culture to corneal keratocytes or keratocytes that that produce suitable corneal stroma ECM material). Corneal stroma ECM material is an ECM that comprises aligned collagen, keratan sulfate and keratocan.

One or more of therapeutic agents can be introduced into the scaffold by any useful method, such as, without limitation absorption, adsorption, deposition, admixture with a polymer composition used to manufacture the scaffold and linkage of the agent to a component of the scaffold. It should be noted that the active agents can be added to the template scaffold and/or to the product ECM scaffold formed within the template scaffold. In one non-limiting example, the therapeutic agent is introduced into a backbone of a polymer used in the template scaffold. By adding the therapeutic agent to the polymer itself, the rate of release of the therapeutic agent may be controlled by the rate of polymer degradation. During an electrospinning process, the therapeutic agent can be electrosprayed onto the polymer being spun. In yet another non-limiting example, the therapeutic agent is introduced into the scaffold after the product ECM scaffold is formed. For instance, the scaffold may be "loaded" with therapeutic agent(s) by using static methods. For instance, the scaffold can be immersed into a solution containing the therapeutic agent permitting the agent to absorb into and/or adsorb onto the scaffold. The scaffold may also be loaded by using dynamic methods. For instance, a solution containing the therapeutic agent can be perfused or electrodeposited into the scaffold.

Therapeutic agents within the template and product ECM scaffold can be used in any number of ways. In one non-limiting embodiment, a therapeutic agent is released from the scaffold. For example and without limitation, anti-inflammatory drugs are released from the scaffold to decrease an immune response. When the ECM product scaffold is implanted in a patient's cornea, it may be desirable to include an anti-inflammatory agent and/or an antibiotic. Non-limiting examples of suitable antibiotics include: ciprofloxacin, norfloxacin, afloxacin, levofloxacin, gentamicin, tobramycin, neomycin, erythromycin, trimethoprim sulphate, and polymyxin B. Steroidal anti-inflammatories are useful, but not preferred because they cause corneal thinning. Non-steroidal anti-inflammatories (NSAIDs) suitable for ocular use are preferred and include, without limitation: nepafenac (for example and without limitation, Nevenac 0.1%, nepafenac ophthalmic suspension, Alcon Laboratories, Inc.), ketorolac tromethamine (for example and without limitation, Acular LS 0.4%, ketorolac tromethamine ophthalmic suspension, Allergan, Inc.), acetaminophen and bromfenac (for example and without limitation, Xibrom 0.09%, bromfenac ophthalmic suspension, Ista Pharmaceuticals). In another non-limiting embodiment, a therapeutic agent is intended to substantially remain within the scaffold. For example and without limitation, chemoattractants are maintained within the scaffold to promote cellular migration and/or cellular infiltration into the scaffold.

In a non-limiting embodiment, at least one therapeutic agent is added to the product ECM scaffold before it is implanted in the patient. Generally, the therapeutic agents include any substance that can be coated on, embedded into, absorbed into, adsorbed to, or otherwise attached to or incorporated onto or into the biodegradable scaffold that would provide a therapeutic benefit to a patient. Non-limiting examples of such therapeutic agents include antimicrobial agents, growth factors, emollients, retinoids, and steroids. Each therapeutic agent may be used alone or in combination with other therapeutic agents.

In certain non-limiting embodiments, the therapeutic agent is a growth factor, such as a neurotrophic or angiogenic factor, which optionally may be prepared using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons. Commercial preparations of various growth factors, including neurotrophic and angiogenic factors, are available from R & D Systems, Minneapolis, Minn.; Biovision, Inc, Mountain View, Calif.; ProSpec-Tany TechnoGene Ltd., Rehovot, Israel; and Cell Sciences®, Canton, Mass.

In certain non-limiting embodiments, the therapeutic agent is an antimicrobial agent, such as, without limitation, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate.

In certain non-limiting embodiments, the therapeutic agent is an anti-inflammatory agent, such as, without limitation, an NSAID, such as salicylic acid, indomethacin, sodium indomethacin trihydrate, salicylamide, naproxen, colchicine, fenoprofen, sulindac, diflunisal, diclofenac, indoprofen, sodium salicylamide; an anti-inflammatory cytokine; an anti-inflammatory protein; a steroidal anti-inflammatory agent; or an anti-clotting agents, such as heparin.

In certain non-limiting embodiments, the therapeutic agent comprises cells that are added to the biodegradable scaffold before or at the time of implantation. The cells may be cells used to transform the template scaffold to the product ECM scaffold. Because the cells are to be implanted in the cornea of a patient, though the eye is immune-privileged, it may be preferred to use only autologous cells. The use of autologous functional keratocytes implies that the functional keratocytes or corneal stroma stem cells are obtained from the cornea of the implant patient (as corneal stem cells or keratocytes), and then the cells are propagated and seeded onto the template scaffold. As such, it may be that the only time this strategy is used is where the patient has such substantial scarring to the cornea that removal of a portion of the patient's stroma for ex vivo expansion of cells would be acceptable to the patient.

"Functional keratocytes" are cells that have the ability to deposit an organized transparent ECM scaffold, but which may or may not be keratocytes per se as they exist in the human body, or other animal, with precisely the same phenotypic markers as natively found in the human body. They may be differentiated cells that are not literally keratocytes, but cells exhibiting the ability to function as keratocytes in their ability to deposit organized, transparent ECM including collagen, keratan sulfate and keratocan. As indicated below, the cells differentiated from hCSSCs and ADSCs in KDM are considered to be functional keratocytes, whether or not they are strictly keratocytes as found in the human body. Nevertheless, "functional keratocytes" includes keratocytes as they naturally exist.

As mentioned above, virtually any cell, human or non-human can be used to seed the template scaffold, so long as it can be used to prepare a useful product ECM. For many tissues, the choice of cells is less critical than in the case of cornea repair or correction. Where the final scaffold product is decellularized, the cells used to seed the template scaffold do not have to be autologous. For instance allogeneic human corneal stem cells can be obtained as described below, for example from donors where the cornea is not suitable for direct transplantation. As also described below, xenogeneic corneal stem cells also may be used because they may actually form a product ECM scaffold that is more suitable for human implantation than a scaffold formed from human corneal keratocytes differentiated from human corneal stem cells ex vivo. This would be a matter of optimization using the methods described herein.

The product ECM scaffold can be sterilized, and typically decellularized by any of a number of standard methods without loss of its ability to induce endogenous tissue growth. The material may be decellularized by repeated freeze-thaw cycles and then washed to remove debris. In another example, the material can be sterilized by propylene oxide or ethylene oxide treatment, gamma irradiation treatment (0.05 to 4 mRad), gas plasma sterilization, peracetic acid sterilization, or electron beam treatment. The scaffold can be disinfected by immersion in 0.1% (v/v) peracetic acid (σ), 4% (v/v) ethanol, and 96% (v/v) sterile water for 2 h. The ECM material is then washed twice for 15 min with PBS (pH=7.4) and twice for 15 min with deionized water.

Product ECM preparations can be considered to be "decellularized", meaning the cells have been removed from the source tissue through processes described herein and known in the art.

In one non-limiting embodiment, the cells used to prepare the scaffold may be genetically modified cells that are capable of expressing a therapeutic substance, such as a growth factor, or even one or more specific ECM constituents. Cells can be modified by any useful recombinant method in the art. For example and without limitation, the therapeutic agent is a growth factor that is released by cells transfected with cDNA encoding for the growth factor. Therapeutics agents that can be released from cells include, without limitation, a neurotrophic factor, such as nerve growth factor, brain-derived neurotrophic factor, neurotrophin-3, neurotrophin-4, neurotrophin-5, and ciliary neurotrophic factor; a growth factor, such as basic fibroblast growth factor (bFGF), acidic fibroblast growth factor (aFGF), vascular endothelial growth factor (VEGF), hepatocyte growth factor (HGF), insulin-like growth factors (IGF), platelet derived growth factor (PDGF), transforming growth factor-beta (TGF-β), pleiotrophin protein (neurite growth-promoting factor 1), and midkine protein (neurite growth-promoting factor 2); an anti-inflammatory cytokine; and an anti-inflammatory protein. The cells may be autologous, allogeneic, etc.

In addition to preparing and providing the product ECM scaffolds as described above, methods of using such scaffolds are encompassed herein. Generally, the scaffold can be implanted by using any suitable medical procedure that facilitates use of the scaffold to provide a therapeutic benefit. As used herein, the terms "implanted" and "implantation" and like terms refer to an act of delivering a biodegradable elastomeric scaffold to a site within the patient and of affixing the scaffold to the site. The site of implantation in a patient typically is "at or near a site for wound healing or tissue generation or regeneration in the patient," meaning the scaffold-containing device is implanted in, on, onto, adjacent to or in proximity to a desired site of delivery to facilitate healing and/or tissue generation or regeneration to repair an injury or defect in the patient and/or to achieve a desired effect in the patient, such as wound drainage. The delivery method may also include minimally invasive methods such as by catheter based technology or by needle injection. The patient may be human or animal. The scaffold may be delivered by any surgical procedure, including minimally invasive techniques, such as laparoscopic surgery, as well as invasive techniques such as thoracic surgery and fasciotomy. In certain non-limiting embodiments, the elastomeric scaffolds are used as surgical fabrics. For example and without limitation, the scaffold can be implanted in a patient during laparoscopic procedures to repair or to reinforce fasciae that have been damaged or weakened. The elastomeric scaffolds can also be used to re-join organs that have been separated as a result of surgery, to treat hernias, and to promote the healing of surgical incisions. The scaffold may be implanted alone or implanted in conjunction with surgical fasteners, such as sutures, staples, adhesives, screws, pins, and the like. Additionally, biocompatible adhesives, such as, without limitation, fibrin-based glue) may be used to fasten the scaffolds as well.

In other non-limiting embodiments, the biodegradable elastomeric scaffolds may be used to promote healing of deep tissue wounds, such as puncture wounds, bullet wounds, or wounds that result from the surgical removal of a substantial amount of tissue, such as in debridement procedures or removal of tumors. In yet another non-limiting embodiment, the scaffold can be in the form of a powder or fine particles (for example, formed by shredding a non-woven mesh formed the methods described herein), and is packed directly into the wound to provide a matrix on which the patient's cells may grow. In these situations, it may be advantageous to derivatize the scaffold with therapeutic agents, such as antibiotics or growth factors, prior to insertion into the wound.

According to one non-limiting embodiment, the scaffold is a corneal stroma scaffold that is prepared as described above. In this embodiment, the product ECM scaffold is prepared and/or processed in a shape and size suitable for insertion into the cornea as a stroma replacement or supplement. Therefore the scaffold may replace scarred or damaged corneal stroma tissue, or may be implanted in a refractive surgical procedure to change the refractivity of the cornea to correct refractive imperfections in the eye.

This method comprises transplanting shaped discs of bioengineered stromal tissue or decellularized ECM material into healthy eyes in order to change the refractive power of the cornea and reduce the need for contact lenses or glasses. It involves placing the tissue at the surface (onlay) or in a stromal pocket (inlay) near the front of the stroma. The shape of the tissue results in altered corneal refraction correcting refractive errors in the eye that require glasses. In a corneal inlay method, the scaffold material is placed within the cornea under a LASIK-style flap. Then in position, the implant changes the curvature of the cornea such that the front of the eye acts in the manner of a multifocal contact lens. This method is used in connection with the Vue+ lens (Revision Optics, Lake Forest, Calif.). In another method, a laser creates a tiny pocket in the cornea into which the scaffold is placed. This method is used in connection with the Flexivue Microlens (Presbia Coöperatief, U.A., Amsterdam). In another embodiment, the scaffold is implanted as an onlay by placing the scaffold just under the epithelial layer on the front surface of the cornea. This method is used in connection with the corneal onlay provided by Adventus Technology of Irvine, Calif.

EXAMPLES

Example 1

Use of hCSSCs to Produce Corneal Stroma Biomaterial

An orderly three dimensional (3-D) collagen fibril nanoconstruct that mimics corneal stroma tissue was generated by employing a tissue engineering strategy. We demonstrated that aligned nanofibrous scaffold prepared from poly(ester urethane)urea (PEUU) provided the topographic cues to regulate morphogenesis of human corneal stromal stem cells (hCSSCs), and initiate and guide self-organization of hCSSC-secreted collagen fibrils into 3-D orderly construct. The yielded construct features the uniform fiber diameter and interfibrillar spacing, which are believed to be controlled by collagens and proteoglycans typifying human corneal stromal tissue. These striking results represent an important first step of a bottom-up strategy to bioengineer complex collagen-based nano-biological construct for tissue repair and regenerative medicine.

Materials

The biodegradable Poly(ester urethane) urea (PEUU) was synthesized as follows. First, 1,4-diisocyanatobutane and polycaprolactone-diol (PCL, $M_w$=2 kg/mol) were reacted in dimethyl sulfoxide (DSMO, Anhydrous Grade) for three hour at 75° C. with the aid of Tin 2-ethylhexanoate under the protection of $Ar_2$ purge. After cooling down to room temperature, the oligomer solution was drop-wise added to 1,4-diaminobutane under vigorous stirring. After 18 hour reaction at room temperature, the polymer solution was precipitated in distilled water. Then the precipitant was soaked in anhydrous 2-propanol for another 48 hours to remove DMSO and unreacted monomers. The yielded polymer was incubated in anhydrous ethanol for another 24 hours to remove water, and then further dried under vacuum at 40° C. for one week in order to remove water residual. The yielded product was a white elastomer.

Cell Culture

Donor human corneas not usable for transplantation were rinsed and incubated in 2.4 U/ml Dispase II (Roche Diagnostics, Pleasanton, Calif.) overnight at 4° C. Epithelial and endothelial cells were removed by dissection and debridement, and the stroma was minced into 2-mm cubes. Stroma was digested up to 3 hours at 37° C. in Dulbecco's modified Eagle's medium (DMEM) containing 1 mg/ml collagenase type L (Sigma-Aldrich) and 0.2 mg/ml testicular hyaluronidase (Sigma-Aldrich). Primary stromal cells were cultured at $1\times10^4$ per $cm^2$ in a humidified atmosphere containing 5% $CO_2$ in a medium (stem cell growth medium [SCGM]) modified from Jiang et al. (Pluripotency of mesenchymal stein cells derived from adult marrow. Nature 2002;418:41-49) containing DMEM/MCDB-201 (Sigma-Aldrich) with 2% fetal bovine serum (FBS) (HyClone, Logan, Utah), 10 ng/ml epidermal growth factor (Invitrogen Corporation, Carlsbad, Calif.), 10 ng/ml platelet-derived growth factor (PDGF-BB) (Sigma-Aldrich), 5 µg/ml insulin, 5 µg/ml transferrin, 5 ng/ml selenous acid (ITS) (Invitrogen), 1,000 units per ml leukemia inhibitory factor (LIF) (Chemicon International), ×1 linoleic acid-bovine serum albumin (LA-BSA), 0.1 mM ascorbic acid-2-phosphate, 10-8 M dexamethasone, 100 IU/ml penicillin, 100 µg/ml streptomycin, 50 µg/ml gentamicin, and 1.25 µg/ml amphotericin B (Sigma-Aldrich). When 80%-90% confluent, cells were trypsinized and subcultured. Passage 6 cells were used for cell culture.

Cell Sorting

At passage four, trypsinized cells were incubated at $1.0\times10^6$ cells per ml in DMEM with 2% FBS and 5 µg/ml Hoechst 33342 dye (Molecular Probes, Inc.) for 90 minutes at 37° C. To inhibit ABCG2-mediated efflux of Hoechst dye, cells were preincubated for 20 minutes with 50 µg/ml verapamil (an inhibitor of multidrug resistance proteins) (Sigma-Aldrich) before Hoechst 33342 incubation. After staining, the cells were washed twice in Hanks' balanced salt solution (HBSS) with 2% FBS and then stored in cold HBSS with 2% FBS on ice. Immediately before sorting, 2 µg/ml propidium iodide (Sigma-Aldrich) was added to identify nonviable cells for flow cytometric analysis. Cells were analyzed on a MoFlo (DakoCytomation, Fort Collins, Colo.) high-speed cell sorter, using 350-nm excitation. Cells showing reduced fluorescence of both blue (670 nm) and red (450 nm), a "side population," were collected. Dead cells stained with propidium iodide were omitted from the population.

SP Cell Culture, Cloning, and Differentiation

After sorting, SP cells were cultured in SCGM. At 80%-90% confluence, these cells were cloned by limiting dilution and subcultured at a density of $1\times10^4$ cells per $cm^2$. Cloned cells were used in all subsequent experiments. To determine differentiation potential, cloned passage-18 SP cells were incubated 2 weeks in Advanced D-MEM (Invitrogen Corporation) supplemented with fibroblast growth factor 2 (FGF2) and 10 ng/ml (keratocyte differentiation medium [KDM]).

Antibodies used included anti-keratocan peptide antibody (Guan, J.; Fujimoto, K. L.; Sacks, M. S.; Wagner, W. R. *Biomaterials* 2005, 26, 3961-3971), J19 monoclonal to keratan sulfate (Sigma-Aldrich), anti-collagen I (Sigma-Aldrich), anti-collagen V (Chemicon, Temecula, Calif.), anticollagen VI (Chemicon, Temecula, Calif.) for immunostaining. For fluorescent staining, Alexa Fluor-488 anti-mouse IgG, Alexa Fluor-546 anti-rabbit IgG, and nuclear dye DAPI were obtained from Molecular Probes (Eugene, Oreg.).

Scaffold Preparation

The oriented nanofibrous scaffolds were prepared by electrospinning technique. Briefly, PEUU was dissolved in hexafluoroisopropanol (HFIP) under mechanical stiffing at room temperature. The obtained polymer solution was fed by syringe pump (Harvard Apparatus) into a steel capillary (I.D.=0.047 inch) suspended on an aluminum wheel collector with 2-cm in width and 20-cm in thickness. A combination of two high-voltage generators (Gamma high Voltage Research) was employed with a high positive voltage (+10 kV) to charge the steel capillary containing polymer solution, and a high negative voltage (−5 kV) to charge the aluminum wheel collector with 20 cm in diameter. The distance between the tip of the steel capillary and the top of the aluminum wheel collector is 15 cm. The volume flow rate was set up as 1 ml/hr. The PEUU solution was electrospun with 5.0 wt-% concentration and rotational speed is 2000 rpm. The yielded fibrous scaffold is approximate 200 micron thick.

The cast film was prepared as a control to assess the influence of artificial surface features on cell morphology and the result collagen self-organization. The 5.0 wt-% PEUU/HFIP solution was poured in Teflon™ casting dish, where the solvent evaporated to yield semitransparent, mechanically robust films with prescribed thickness of 0.2~0.3 mm. All of the scaffolds were dried in vacuum oven at room temperature for one week in order to eliminate the solvent, e.g. HFIP, completely.

Cell Cultures

The scaffold was punched into round discs with 25-mm in diameter in order to fit in 24-well culture plate. The discs were sterilized by UV exposure (254 nm) in cell culture hood for 20 minute each side. The hCSSCs were statically seeded on the scaffolds at a density of $8.0\times10^4$ cells/$cm^2$, which were incubated in stem cell growth medium (SCGM) containing DMEM/MCDB-201 with 2% fetal bovine serum (FBS), 10 ng/ml DMEM/MCDB-201 with 2% fetal bovine serum (FBS), 10 ng/ml epidermal growth factor, 10 ng/ml platelet-derived growth factor (PDGF-BB), 5 µg/ml insulin, 5 µg/ml transferrin, 5 ng/ml selenous acid (ITS), 1,000 units per ml leukemia inhibitory factor (LIF), ×1 linoleic acid-bovine serum albumin (LA-BSA), 0.1 mM ascorbic acid-2-phosphate, 10-8 M dexamethasone, 100 IU/ml penicillin, 100 µg/ml streptomycin, 50 µg/ml gentamicin, and 1.25 µg/ml amphotericin B.

After three day incubation in SCGM, hCSSC was transferred into ketarocyte differentiation medium (KDM, (KDM; advanced-MEM (Invitrogen) with 10 ng/mL basic fibroblast growth factor (bFGF, Sigma-Aldrich), 0.1 mM L-ascorbic acid-2-phosphate (A2P, Sigma-Aldrich), L-glutamine (1× GlutaMax™-1; Invitrogen), 50 µg/ml Gentamicin (Invitrogen), 100 µg/ml penicillin (Mediatech, Inc.), which was changed twice one week for up to 6 weeks.

Two-Photon Fluorescent Microscopy

Differentiated hCSSC morphologies were observed with Two-photon Fluorescent microscope. Scaffolds were randomly chosen from 24-well plate on day 14, 28, and 42.

Scaffolds were washed with PBS and were stained with CellTracker™ Green CMFDA (5-chloromethylfluorescein diacetate) (Invitrogen) for 10 minutes. Samples were observed under two-photon fluorescent microscope.

Electron Microscopy

The morphologies of the differentiated hCSSCs and their secreted extracellular matrix on the scaffold were investigated by Scanning Electron Microscope (SEM). The specimens were fixed in cold 2.5% glutaraldehyde (25% glutaraldehyde EM grade, Taab Chemical) in 0.1 M PBS (sodium chloride, potassium chloride, sodium phosphate dibasic, potassium phosphate monobasic, Fisher), pH=7.3. The specimens were rinsed in PBS, post-fixed in 1% Osmium Tetroxide (Osmium Tetroxide crystals, Electron Microscopy Sciences) with 0.1% potassium ferricyanide (Potassium Ferricyanide, Fisher), dehydrated through a graded series of ethanol (30%~90%-Reagent Alcohol, Fisher, and 100%-Ethanol 200 Proof, Pharmco), and hexamethyldisilazane (HMDS). The yielded sample was investigated at 5 kV by Jeol JSM-6330F Scanning Electron Microscope (SEM) equipped with a digital camera.

The internal microstructures of the yielded ECM were investigated employing Transmission Electron Microscope (TEM). The sample was cut parallel and perpendicular to the alignment direction of PEUU fibrous scaffolds, respectively, in order to assess the influence of scaffold surface features on the ECM organization. The specimens were fixed in cold 2.5% glutaraldehyde (25% glutaraldehyde EM grade, Taab Chemical) in 0.1M PBS (sodium chloride, potassium chloride, sodium phosphate dibasic, potassium phosphate monobasic, Fisher), pH=7.3. The specimens were rinsed in 1×PBS, post-fixed in 1% Osmium Tetroxide (Osmium Tetroxide crystals, Electron Microscopy Sciences) with 0.1% potassium ferricyanide (Potassium Ferricyanide, Fisher), dehydrated through a graded series of ethanol (30%-90%-Reagent Alcohol, Fisher, and 100%-Ethanol 200 Proof, Pharmco) and embedded in Epon (Dodecenyl Succinic Anhydride, Nadic Methyl Anhydride, Scipoxy 812 Resin and Dimethylaminomethyl, Energy Beam Sciences). Semi-thin (300 nm) sections were cut on a Reichart Ultracut, stained with 0.5% Toluidine Blue (Toluidine Blue O and Sodium Borate, Fisher) and examined under the light microscope. Ultrathin sections (65 nm) were stained with 2% uranyl acetate (Uranyl Acetate dihydrate, Electron Microscopy Sciences, and methanol, fisher) and 1% phosphotungstic acid (Sigma-Aldrich), pH 3.2. The sections were examined and photographed at 80 kV on Jeol 1011 transmission electron microscope equipped with a digital camera.

Gene Expression

RNA of the differentiated hCSSCs seeded on the PEUU scaffolds was isolated using the RNeasy mini kit (Qiagen, Valencia, Calif.). RNA was treated with DNAse I (Ambion) and was concentrated by alcohol precipitation. RNA (200 ng) was transcribed to cDNA in a 50 µL reaction containing 1×PCR II buffer (Roche Applied Science, Indianapolis, Ind.), 5 mM $MgCl_2$, 200 µM dNTP mixture (Roche), 2.5 µM random hexamers (Invitrogen), 0.4 U RNase inhibitor, and 125 U SuperScript II reverse transcriptase (Invitrogen). Quantitative PCR of cDNA was performed using assays containing fluorescent hybridization probes (TaqMan; Applied Biosystems, Foster City, Calif.) or with direct dye binding (SYBR Green; Applied Biosystems) according to the manufacturer's instructions. Reactions were carried out on triplicate samples for 40 cycles of 15 seconds at 95° C. and 1 minute at 60° C. after initial incubation at 95° C. for 10 minutes. Reaction volume was 20 µL. For TaqMan assays, reactions contained 1× Universal PCR Master Mix (Applied Biosystems), 1× gene mix, and 3.0 µL cDNA. For SYBR dye-based assays, the reactions contained 1×PCR buffer (Applied Biosystems), 3 mM $Mg^{2+}$, 200 µM dATP, dCTP, dGTP, and 400 µM dUTP, 0.025 U/mL AmpliTaq Gold polymerase, 1.6 µL cDNA and forward and reverse primers at optimized concentrations. Amplification of 18S rRNA was carried out for each cDNA as a qualitative external control. A dissociation curve for each SYBR-based reaction was generated on a real-time thermocycler (Gene-Amp ABI Prism 7700 Sequence Detection System; Applied Biosystems) to confirm the absence of nonspecific amplification. Amplification of 18S rRNA was performed for each cDNA (in triplicate) for normalization of RNA content. Relative mRNA abundance was calculated as the Ct for amplification of a gene-specific cDNA minus the average Ct for 18S expressed as a power of 2 ($2^{-\Delta Ct}$). Three individual gene-specific values thus calculated were averaged to obtain mean±SD. We choose ABCG2 as generic markers of corneal stromal stem cells, and keratocan, aldehyde dehydrogenase 3A1 (ALDH), prostaglandin D2 synthase (PTGDS), Keratan sulphate 6-O-sulphotransferase (CHST6) and Pyruvate dehydrogenase kinase, isozyme 4 (PDK4) as generic markers of keratocytes.

Immunostainning

The PEUU e-spun fibrous scaffolds seeded with hCSSCs were fixed in 4.0% paraformaldehyde in PBS at room temperature for 20 minutes, rinsed in PBS, and stored at 4° C. in PBS until further processing. Except the one for keratocan, the fixed samples were incubated in 10 wt-% heat-inactivated goat serum (HIGS) at room temperature for one hour to block nonspecific binding, rinsed in PBS, and incubated in 1-wt % bovine serum albumine (BSA)-PBS with mouse-monocloned primary antibodies overnight at 4° C. in a sealed moist box. For immunostainning keratocan, the sample was firstly digested and blocked in 1-wt % bovine serum albumine (BSA)-PBS with keratanase (0.5 unit/ml) for two hours at room temperature, rinsed in PBS, then stained by goat-monocloned anti-human keratocan (a kind gift from Dr. Chia-Yang Liu) and incubated overnight at 4° C.

After three washes with PBS, secondary antibody Alexa Fluor 488-conjugated goat anti-mouse or Alexa Fluor 543-conjugated donkey anti-goat (1:2,500) (Invitrogen-Molecular Probes, Eugene, Oreg., http://probes.invitrogen.com) together with 4',6-diamidino-2-phenylindole (DAPI) (0.5 lg/ml) (Roche Molecular Biochemicals, Indianapolis, Ind., http://www.roche.com) was added to the samples, and incubated for 2 hours at room temperature. Omission of the primary antibody served as a negative control. The stained wholemounts were placed in aqueous mounting medium (Thermo Fisher Scientific, Pittsburgh, Pa.) and examined using an Olympus FluoView FV1000 confocal microscope (Olympus, Tokyo).

Results

Figure 2:
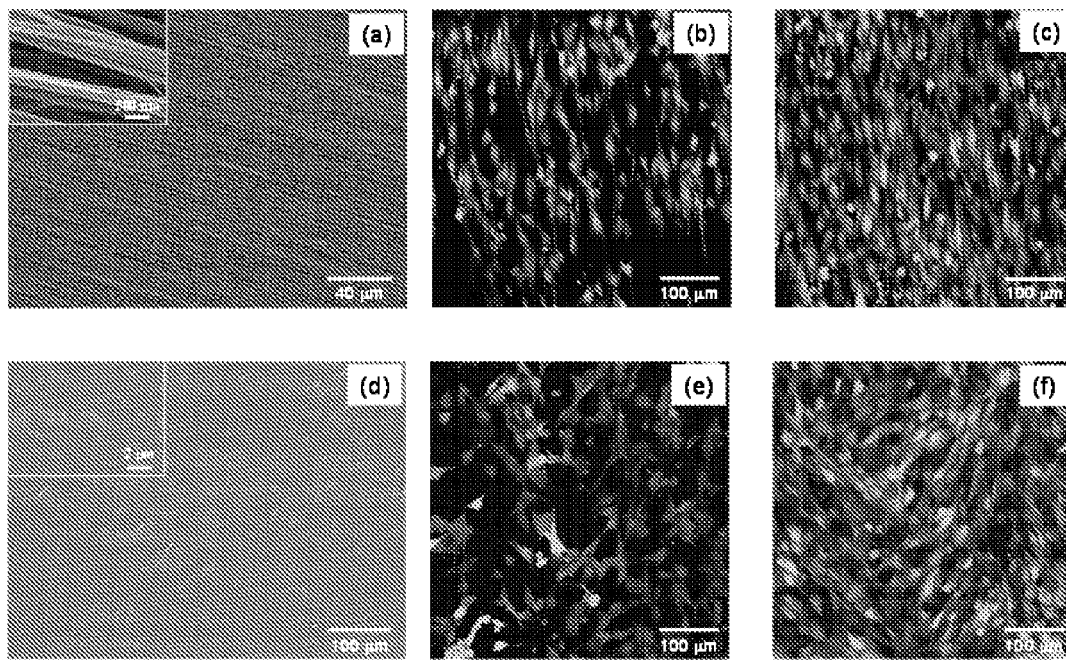
FIG. 2. Morphologies of hCSSCs seeded on two kinds of PEUU scaffolds. The surface morphologies of the two scaffolds were characterized by scanning electron microscope (SEM): (a) aligned nanofibrous PEUU sheet, whose fibers are 165±55 nm in diameter; (d) PEUU cast film. Cellular viability and morphology was evaluated employing Calcein AM, and imaged by confocal laser-scanning microscope (CLSM). (b) and (c) are the fluorescent micrographs of hCSSCs seeded on aligned nanofibrous PEUU sheet for 1-day and 3-day cell seeding, respectively. (e) and (f) are those seeded on PEUU cast film for 1-day and 3-day, respectively.

FIGS. 2(*a*) and (*d*) showed that surface topography of PEUU electro-spun sheet and cast film, respectively. The electrospun PEUU scaffold featured highly oriented fibrils with nano-scale diameter (165±55 nm). In contrast, The PEUU cast film is comparatively flat and smooth. Although there are some local fluctuations induced by thermal perturbation during solvent evaporation, no particular orientation can be noted. The cellular viability and morphology after cell seeding was evaluated employing Calcein AM staining. As shown in FIG. 2(*b*), the fluorescent viable hCSSCs were highly elongated and uniaxially aligned at the oriented fibrous PEUU scaffold. After three-day culture in stem cell growth medium (SCGM) with 2% bovine fetal serum, hCSSCs divided and proliferated to confluence. FIG. 2(c) shows that at latter time points proliferating cells maintain alignment. As expected, hCSSCs were not elongated on flat surface of PEUU cast film, and most of them showed the dendritic features (FIG. 2(e). Similarly, cell morphology had little change with cell confluence after three-day culture in SCGM, as shown in FIG. 2(f).

Figure 3:
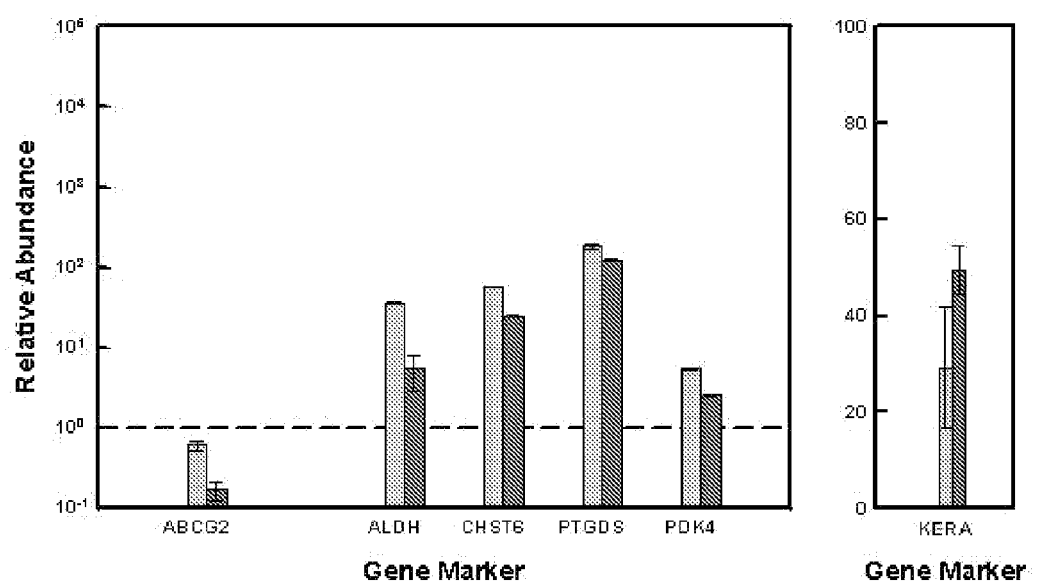
FIG. 3. Changes in gene expression of hCSSCs seeded on scaffolds: (▓) cast film and (▬) aligned nano-fibrous sheet. mRNA abundance was compared with hCSSCs cultured in SCGM (-----). Ratios of abundance of each transcript between hCSSCs seeded on different scaffolds cultured in KDM and in SCGM are expressed on a log scale. Since KERA has no expression in hCSSCs cultured in SCGM, it is expressed in linear plot.

After three-day culture in SCGM, the scaffolds seeded with hCSSCs were transferred into serum-free keratocyte differentiation medium (kDM). After six weeks incubation, analysis of the two types of cultures was carried out. Firstly, we examined the influence of structured surface on the gene expression of hCSSCs cultured in KDM. FIG. 3 showed the changes in gene expression by hCSSCs seeded on aligned nano-fibrous scaffold and cast film in KDM culture. In consistent with our previous observation (Du, Y., et al. *Invest Ophthalmol Vis Sci* 2007, 48, 5038-5045), hCSSCs cultured in KDM down-regulated the expression of ABCG2, a typical marker present in many adult stem cells, and substantially upregulated several generic markers of keratocytes, such as keratocan, aldehyde dehydrogenase 3A1 (ALDH), prostaglandin D2 synthase (PTGDS) and keratan sulphate 6-0-sulphotransferase (CHST6). Specially, hCSSCs do not exhibit keratocan, a typical gene marker expressed in corneal stromal keratocyte. These observations revealed that hCSSCs were effectively differentiated into keratocytes in KDM. The adult stem cell phenotype of differentiated hCSSCs down-regulated much faster on aligned nano-fibrous scaffold than on cast film. Interestingly, keratocyte phenotypes of differentiated hCSSCs on cast film have a little bit stronger expression than those on aligned nanofibrous scaffolds, however except keratocan.

Figure 4:
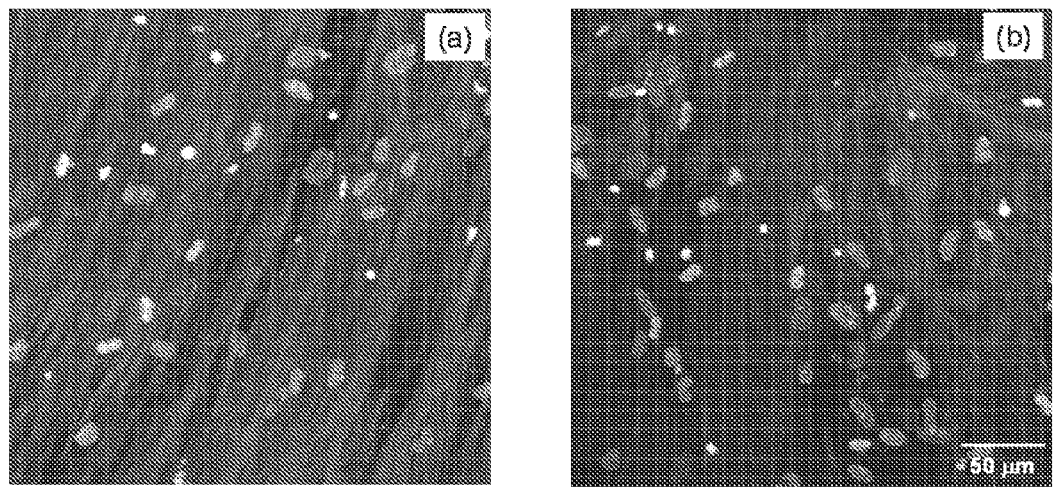
FIG. 4. Two-photon images of hCSSCs-secreted extracelluar matrix (ECM) varying with scaffolds: (a) aligned nanofibrous PEUU scaffold, and (b) cast PEUU film. The second harmonic generation signal for collagens when excited at λ=840 nm is red. Nuclei are stained green.

Highly co-aligned molecules of Type-I collagen lead to strong birefringence. In addition such aligned collagen features a second-order nonlinear susceptibility because of its structural high non-centrosymmetry, resulting in a strong second harmonic generation (SHG). Accordingly, the hCSSCs-secreted extracellular matrix (ECM) was examined by two-photon microscopy. As shown in FIG. 4, although not stained, the second harmonic generation (SHG) signal (in red) is very strong on both scaffolds when excited at $\lambda_{ex}$=840 nm. The SHG-visualized ECMs secreted by hCSSCs are highly cohesive tissue-like masses fibrous form. Specifically, the ECM on the aligned nano-fibrous scaffold was organized into fibril bundles that globally aligned in the whole image from the top view. In contrast, the fibril bundles on cast film are macroscopically random although regional alignment was observed.

Figure 5:
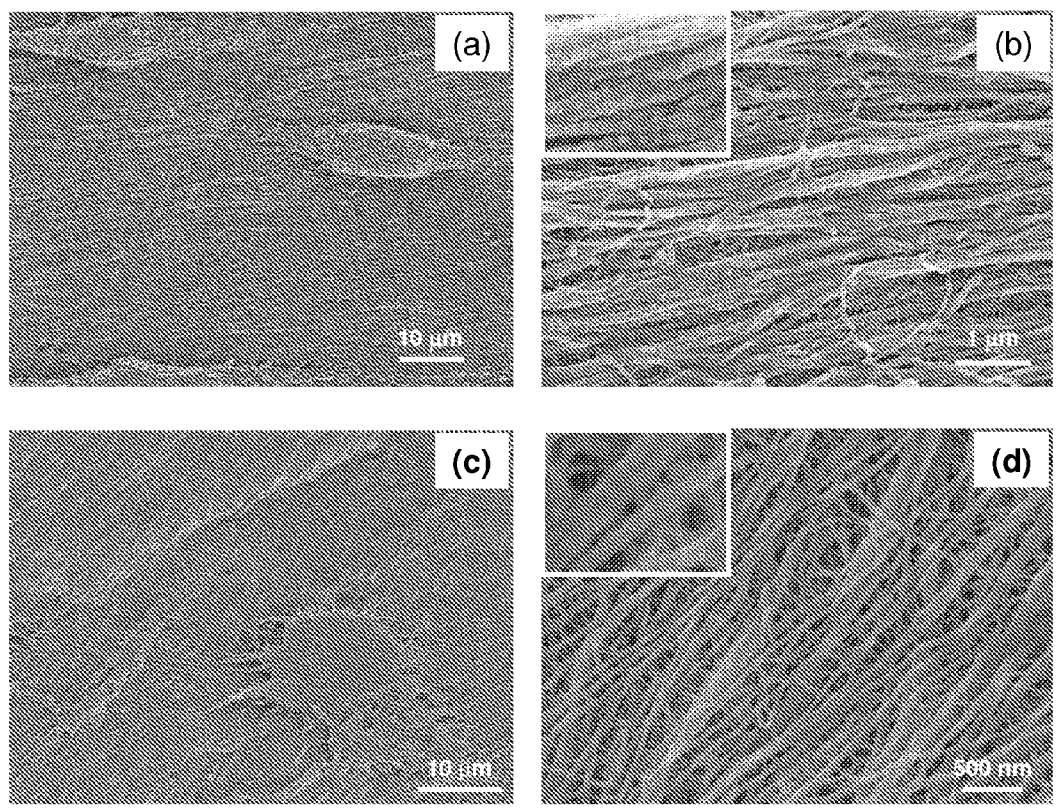
FIG. 5. SEM micrographs of hCSSCs and hCSSCs-secreted ECM on the varying scaffolds. The morphologies of hCSSCs and hCSSCs-secreted ECM were detailed from micron-scale to nano-scale with increasing magnification: (a,b) for aligned nano-fibrous PEUU sheet, and (c,d) for cast PEUU film with increasing magnification. The banded structures along the fibrils are disclosed in inserted parts of (b) and (d).

With scanning electron microscopy, detailed surface morphologies of hCSSCs and their deposited ECMs on the scaffolds from micron-scale to nano-scale were observed. On the aligned nano-fibrous PEUU scaffold, the seeded hCSSCs were elongated, and uniformly oriented in a preferred direction, as shown in FIG. 5(a). There are many dense fine fibers between cells on the scaffold with alignment with high fidelity to hCSSC alignment. FIG. 4(b) demonstrates the detailed microstructures of the hCSSC-secreted fibril-like ECM. The longitudinal axes of the fibrils were closely parallel to each other. Between the fibers, there are numerous fiber-like side chains along the fibrils, which crosslink them together into an integrated collagen construct on the scaffold. As shown in the insert of FIG. 5 (b), a characteristic periodic banded structure was consistently observed similar to the D-band feature found in type-I collagen fibrils.

In FIG. 5(c) a typical cell on the cast film substrate is seen with a dendritic cellular morphology common to the film, but not the aligned fibrillar substrate. The secreted ECM on the cast film was also less densely packed. As shown in FIG. 5(d), there is no preferred alignment in a macroscopic view. The distinct transverse banding pattern, the character of Type-I collagen fiber, can also be seen along each fibril as shown in the insert of FIG. 5(d). Individual fibrils secreted from hCSSCs on cast film did not appear to vary greatly from those on aligned nano-fibrous sheets. Since SEM visualization only allowed assessment of the top layer of hCSSCs-secreted ECM organization, transmission electron microscopy was utilized to evaluate whether ECM distribution in the z-direction was consistent with physiological structures and varied between substrate types.

Figures 1, 6:
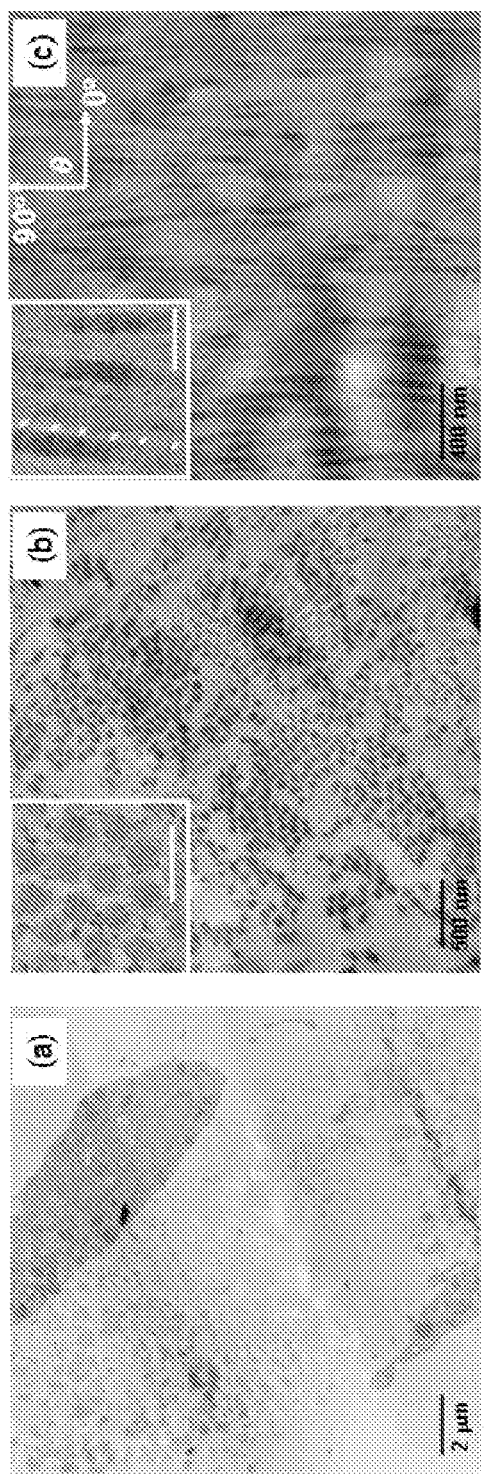
FIG. 6. Transmission electron micrographs of hCSSCs seeded on aligned nano-fibrous PEUU sheets (a-c) and cast PEUU films (g-h) for six weeks. TEM micrographs ((a) and (b)) revealed fibers from cells on the aligned scaffold exhibited high fidelity to a preferred orientation and long-range order. The fibers were normal to the viewing plane when the section crossed the cell long axis (a and b), whereas when the section was along the cell long axis, fibers were nearly parallel to each other. Digital analysis of the fiber diameter, fiber spacing and fiber orientation are seen in (d), (e) and (f), respectively. Fibers generated on the cast film randomly distributed in the construct (g and h). The scale bar in the insert is 100 µm.
Figures 2, 6:
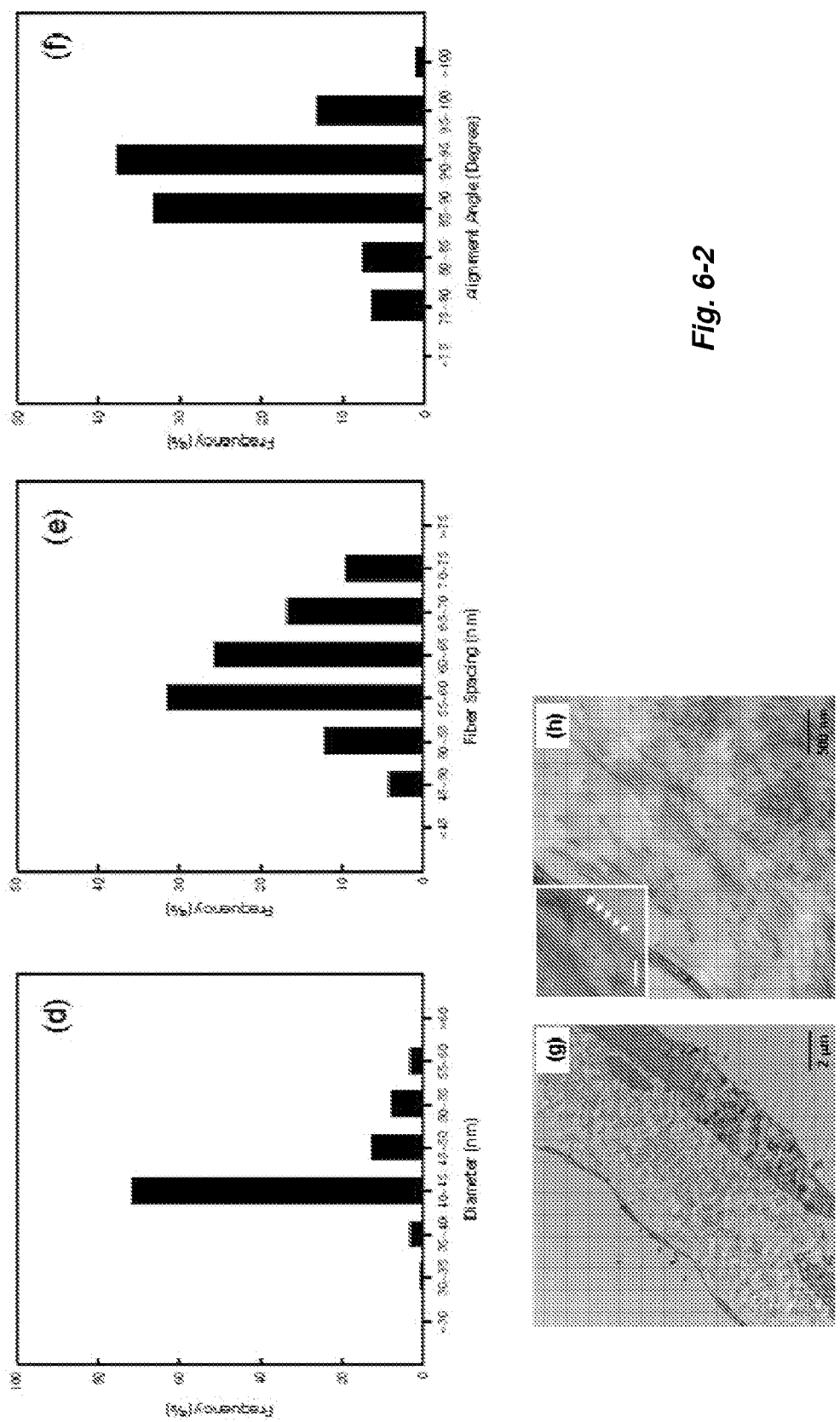

Transmission electron micrographs of the hCSSCs-secreted ECM in cross-section are shown in FIG. 6. Due to the defined structural anisotropy, hCSSC-secreted ECM on aligned nano-fibrous scaffolds was microtomed in orthogonally: along and across the fiber long axis. For samples cut across the fiber long axis, the hCSSC-secreted ECM was sandwiched by single cell layers and was ~7-8 μm thick, as shown in FIG. 6(a). No cells were found in this gap. When viewed at higher magnification (FIG. 6(b)), all of the fibrils were found to be normal to the imaging plane. Within the ECM dense fiber clusters were present, with uniform fiber spacing, often as part of a "pseudo-hexagonal" lattice that is characteristic of native corneal stroma, (seen in the insert of FIG. 6(b)). Fiber diameter (40.2±2.7 nm) and spacing (60.9±6.5 nm) within the clusters were analyzed by digital image processing with the distributions summarized in FIG. 6(d, e). For samples cut along the fiber long axis, all fibers were found to be parallel to the viewing plane and each other and to be packed into clusters as shown in FIG. 6(c). Digital analysis summarized in FIG. 6(f) revealed that the preferred angle (θ) was 89.8°±5.2°. As shown in the insert of FIG. 6(c), uniform periodic banding could clearly be seen along each fiber with a periodicity of 67 nm, which is very close to the characteristic D-spacing of native Type-I collagen. For hCSSCs cultured on cast film a sandwiched ECM was also observed, as shown in FIG. 6(g). However, in this case the fibers in the 5~6 μm thick ECM did not exhibit any preferred orientation. Under higher magnification (FIG. 6(h)), it can be seen that fiber size was not uniform; however the characteristic axial D-periodicity was observed along the secreted fibers.

Figure 7:
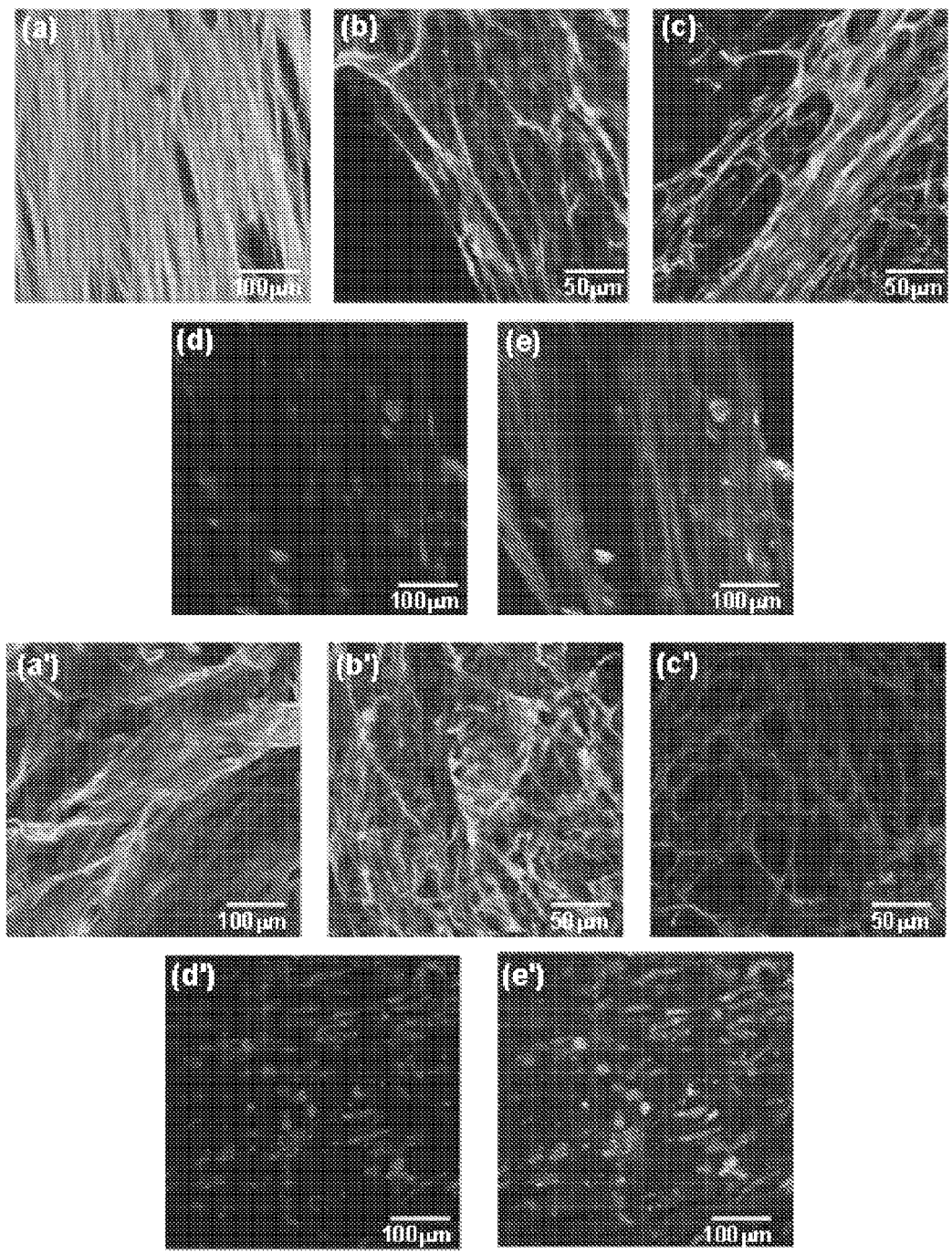
FIG. 7. Immunofluorescence micrographs of hCSSC-secreted ECM on (a-e) aligned nano-fibrous PEUU sheet and (a'-e') cast PEUU film after six weeks culture: (a, a') collagen I, (b, b') collagen V, (c, c') collagen VI, (d, d') keratan sulfate and (e, e') keratocan. Nuclei were stained with DAPI and appear blue.

Also examined was the expression of collagens and proteoglycans typifying the unique ECM of human corneal stromal tissue by whole mount immunohistochemical staining. In FIG. 7(a, a') it is seen that type-I collagen was abundant in both secreted ECMs. Confirming electron microscopy analysis, the fibrous ECM deposited on the aligned nano-fibrous sheet exhibited high alignment of type-I collagen. In addition, collagen V, collagen VI, keratan sulfate and keratocan were also detected as shown in FIG. 7(b-e). All of these representative collagens and proteoglycans can also be found in hCSSC-secreted ECM on the cast film, as shown in FIG. 7(a'-e'). However, on this film the fibrils demonstrated no preferred orientation. Structurally, the ECM on aligned nano-fibrous sheet better approximated the flattened lamellae of corneal stromal tissue, e.g. one single layer construct with highly orderly uniform Type-I collagen fibrils. These results were in accordance with the observations from two-photon microscopy.

Nano-structured collagen fiber is the fundamental building block of connective tissue and extracellular matrix (ECM). It is critical to design and manipulate structured collagen-based ECM for the success in tissue repair and regeneration medicine. In this study, we tentatively bioengineer 3-D orderly nano-structured collagen-fibril construct employing tissue engineering strategy. Human cornea stroma is an avascular and acellular tissue, and an organization of corneal stroma collagen fibrils with mono-disperse fiber diameter and uniform local interfibrillar spacing. Hierarchically, it consists of ~200 collagen-fibril lamellae, each about 1.5~2.5 micrometer in thickness. The collagen fibers of each lamella are parallel with one another, but perpendicular to those of adjacent lamellae produced by keratocytes. Thus organizational and structural characteristics mean that corneal stroma tissue is an ideal candidate for us to evaluate our strategy.

Cells, biomaterials-based scaffold, and biochemical and physio-chemical factors are the main factors for the success of tissue engineering. In native corneal stroma tissue, keratocytes play the fundamental function to sustain stroma tissue by secreting a spectrum of unique matrix proteoglycans. Unfortunately, they are not practical in tissue engineering because they will irreversibly lose their phenotypes and differentiate into fibroblast during their population expansion in serum-containing medium. The fibroblast has much less expression of keratocan and keratan sulfate, both of which are key molecules in the connective tissue matrix of the cornea of the eye, and are believed to play functional roles in collagen organization and the resulting corneal transparency. Morphologically, pure fibroblast pellet culture was lack of abundant and organized collagen fibrils. In contrast, hCSSCs pellet culture showed the abundant extracellular matrix containing collagen fibrils. Specially, some aligned collagen fibrils can be observed at the peripherial region. However, most of them are in the form of amorphous spheroids. These observations demonstrated that hCSSCs cannot self-organize into 3-D orderly collagen-fibril construct by themselves without the guidance of an appropriate cellular environment.

Simply embedding cells in scaffolds usually result in poorly organized ECM (Langer, R., et al. *Science* 1993, 260, 920-926). Similarly, cell-secreted ECMs were in a form of an overall random orientation when cells were seeded on the substrate without features (Guillemette, M. D., et al. *Integrative Biology* 2009, 1, 196-204). Although there are several methods to make cells orient in one preferred direction, micro-patterned surface is the simplest one by providing the physical cue to cells. Gerecht et al. (*Biomaterials* 2007, 28, 4068-4077) revealed that nano-structured PDMS surface coated by fibronectin can induce the reorganization of human embryonic stem cells' (hESCs') cytoskeleton components to modulate their morphology and proliferation. Guillemette et al. (*Integrative Biology* 2009, 1, 196-204) found the multiple cell layers on the micro-patterned SEBS surface. Although the first cell layer aligned in the direction of the gratings, the second one varied with cells. The second corneal fibroblast layer shifted angle of 53±8 degree relative to the first layer, and the second smooth muscle cell layer features 39±4 degree shift. In contrast, the second layer of dermal fibroblast had no orientation.

In this study, we fabricated aligned nano-fibrous scaffolds using poly(caprolactone) (PCL)-based poly(ester urethane) urea (PEUU) employing electrospinning technique. PEUU shows high elasticity, biocompatibility without toxic degradation products, and excellent processability. It is an ideal scaffold material used for soft tissue engineering. The yielded scaffold feature an aligned nano-structured surface, which effectively induced hCSSCs to elongate and align following the PEUU fiber orientation as shown in FIG. 2(*b*, *c*). As a comparison, flat PEUU cast film surface is incapable to guide cells' alignment, on which cell morphology is dendritic.

The cell morphology and alignment directly affect the organization of cell-secreted ECM. SEM micrographs showed that on the aligned nano-fibrous PEUU sheet, hCSSCs-secreted collagen fibers were guided to grow along long axis of the elongated hCSSCs. As a comparison, the dendritic hCSSCs on the flat counterpart produced the ECM in an amorphous manner. TEM further revealed the internal microstructures of these resulting ECM construct. On the aligned nano-fibrous PEUU scaffold, the secreted collagens self-organized in one preferred direction in the whole construct, which was sandwiched by two cell mono-layers at the top and bottom. The fact that the surface observation is in accordance with the internal one means that collagen fibers grow up in self-similar manner: the existent collagens guide the new one to grow up. Different from the constructs by corneal fibroblasts seeded on micro-patterned SEBS substrate (Guillemette, M. D., et al. *Integrative Biology* 2009, 1, 196-204), the differentiated hCSSCs didn't make multi cell-layer with an angle shift during the six-week culture. It may be assigned to our serum-free culture medium, resulting in much less cell division. The controllable alignment of cells and cell-secret collagen fibrils is very significant of us to design and manipulate more complicated 3D-orderly collagen fibril construct employing bottom-up strategy.

Another important observation is that collagen fibers in the construct feature the uniform size and interfibrillar spacing. It is genetically similar with the corneal stroma, although it is just one layer observation. As a comparison, the collagen-fibril constructs made from fibroblast lack of highly orderly features, though they show the apparent alignment on micro-patterned SEBS substrate (Guillemette, M. D., et al. *Integrative Biology* 2009, 1, 196-204) and Transwell™ PC membrane (Guo, X. Q., et al. *Invest. Ophthalmol. Vis. Sci.* 2007, 48, 4050-4060). Here, the phenotype of cells is a determinative factor. As shown in FIG. 7, the collagen-fibril constructs secreted from hCSSC showed the strong positive expression of Type-V collagen, Type-IV collagen, keratocan, and keratin sulfate. They determine collagen fibril size and interfibrillar spacing. Type-V collagen is believed to hybrid with Type-I collagen into the collagen fibers in human corneal stroma. The ratio of Type-I collagen to Type-V collagen determine the diameter of hybrid collagen fibrils. The normal ratio in human corneal stroma is 4:1, resulting in 31±0.8 nm in diameter. The observed larger fiber diameter (40.2±2.7 nm) could be due to the larger ratio of Type-I collagen to Type-V one. Type-VI collagen is another major collagen in human cornea besides its Type-I and Type-V counterparts. Keratocan is one member of the small leucine-rich proteoglycan family, and the major keratan sulfate proteoglycans in corneal stroma. It is capable of binding collagen fibers, which results in its highly charged glycosaminoglycan (GAG) chains to extend out. More importantly, its bi-functional characteristic renders it to crosslink the adjacent collagen fibers by protein moieties (This important phenomenon was also observed in our SEM micrographs shown in FIG. 5). Thus makes it essential to regulate collagen fibril diameter, and particularly interfibrillar spacing. The absence of keratocan and other keratan sulfates usually leads to the disorganized fibril spacing. In our case, the interfibrillar spacing within the collagen cluster is pretty uniform (60.9±6.5 nm), although it is irregular out of the collagen-fibril cluster. These typifying proteins can be found their corresponding generic markers in gene expression profiles shown in FIG. 2. For instance, CHST6 codes for an enzyme necessary for the production of keratan sulfate. Its mutations lead to macular corneal dystrophy. KERA codes for the enzyme for the production of keratocan. Its mutations can cause cornea plana. These proteins, whose contents and structures determine the collagen diameter and interfibrillar spacing, were generically species-dependent. Varying with specie, the collagen diameter can change from 24 nm (e.g. Fin whale) to 43 nm (e.g. Camel), and the interfibrillar spacing can change from 39 nm (e.g. Herring) to 67 nm (e.g. Camel).[6] Thus implies that collagen fibril diamter and interfibrillar spacing can be tailored varying with the source of corneal stroma stem cells.

Besides cells and scaffolds, biochemical and physiochemical factors also play a critical role in tissue engineering. Optimizing culture medium is considered as an important way to effectively guide cells to secrete and self-organize ECM in our preferred direction. In this case, serum-free culture medium effectively avoided losing the phenotypes of keratocytes. L-ascorbic acid-2-phosphate (A-2-P) is an important factor to enhance the synthesis and secretion of collagens by ketatocytes. Besides, It has been found that TGF-$\beta_n$ (Transforming growth factor beta) superfamily in cornea, including TGF-$\beta_1$, TGF-$\beta_2$, and TGF-$\beta_3$, also play an important role in modulating keratocyte proliferation, apoptosis, transcription and DNA condensation. Corneal TGF-$\beta_n$ expression is significant for maintaining corneal integrity and corneal wound healing. For example, TGF$\beta_1$ plays a vital role in scar formation in adult corneas. TGF$\beta_2$ and TGF$\beta_3$ are the important factors in corneal development and scarless wound healing during embryogenesis. Compared with the native corneal stroma tissue, our yielded construct is not totally mature and perfect. TGF-$\beta_n$ incorporation can be a potential effective way to improve 3D orderly collagen-fibril construct by hCSSCs, and accelerate the construct mature. The related research has been conducting on the way.

The hCSSCs successfully secreted and self-organized the 3D orderly nano-structured construct comprising collagen fibrils on aligned nano-fibrous sheet. The cells (residing at the top and bottom of ECM) can also be easily decellularized for us to finally obtain the cell-free collagen construct. Conceivably, the structured collagen-based construct can feature many great advantages, including supreme biocompatibility, structural anisotropy, structured surface with aligned collagen fibrils, well-matched modulus, etc. Employing bottom-up strategy, it is feasible for us to fabricate the complex structural organization extracellular matrix (ECM) for tissue repair and regenerative medicine, e.g. bioequivalent of human corneal stroma.

In summary, we successfully prepared the orderly collagen nano-construct employing tissue engineering strategy. We demonstrated that the scaffolds prepared from biodegradable PEUU provided an amenable microenvironment where human corneal stromal stem cells (hCSSCs) could secrete a type-I collagen-based ECM. Scaffold topography played the critical role in initiating and guiding the organized expression of a human corneal stroma-like matrix by hCSSCs. Only the aligned nano-fibrous scaffold resulted in the type-I collagen-based ECM characterized by one lamellae with oriented fibers as well as small and uniform fiber diameters and spacing. As a comparison, collagen fibrils randomly distribute on cast film with flat smooth surface.

More importantly, the detected expressions of collagen type-V, collagen type-VI, keratocan and keratan sulfate, which typify human corneal stromal tissue, indicated that the resulting ECM mimicked human stroma-like tissue. These protein expression profiles also can be found their corresponding generic markers employing RT-PCR technique. Genetically, fiber diameter and interfibrillar spacing can be tuned varying with corneal stroma stem cells source. These striking results evidenced the feasibility that 3D orderly collagen-fibril nano-construct can be generated by mimicking corneal stroma tissue employing tissue engineering strategy. These observations represent an important first step of a bottom-up strategy to bioengineer complex collagen-based nano-biological construct for tissue repair and regenerative medicine.

Example 2

Figure 8:
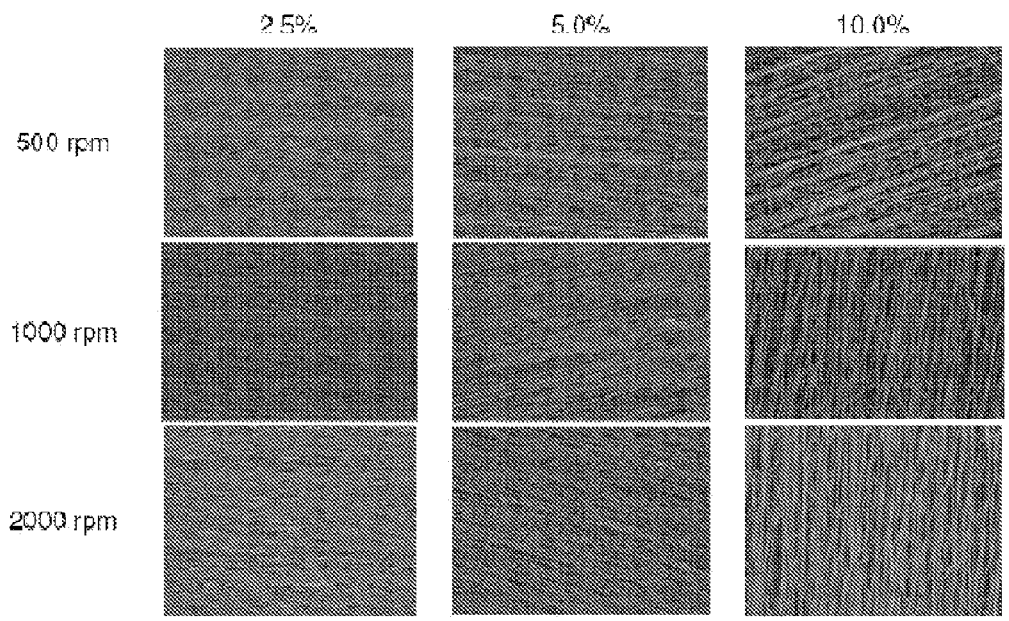
FIGS. 8 and 9 are SEM micrographs of aligned nano-fibril sheets prepared according to the conditions indicated at 1000× and 30,000×, respectively.
Figure 9:
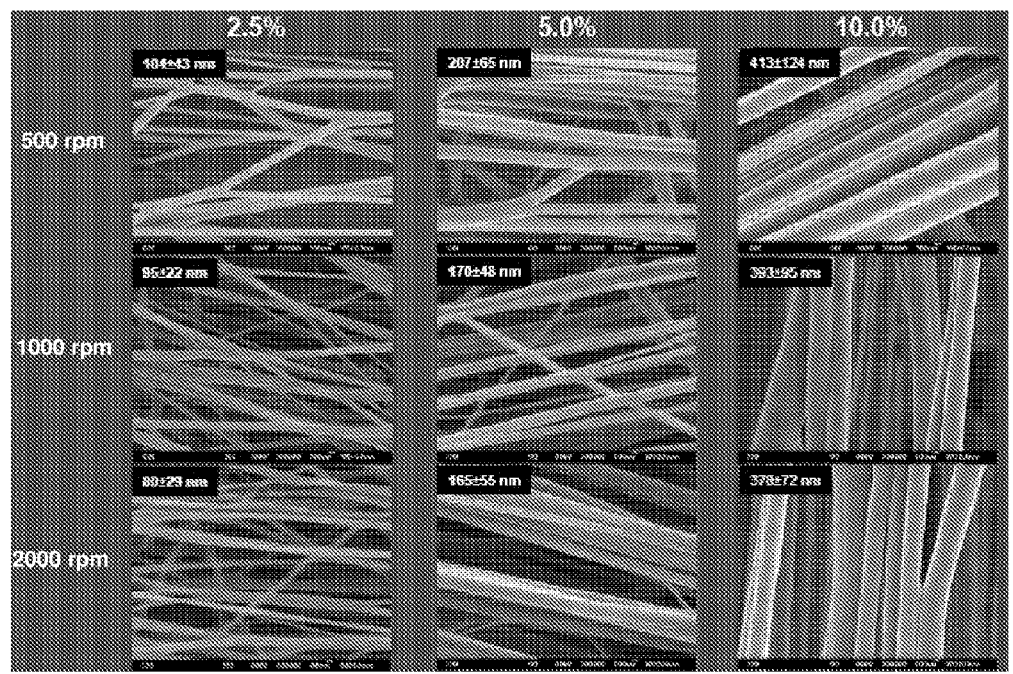

Follow-up studies were performed based on the results illustrated in Example 1. First, the electrospinning parameters were modified in order to determine optimal rotational speeds in relation to the polymer concentration in HFIP. Polymer preparation and electrospinning was performed essentially as described in Example 1. As shown in FIGS. 8 and 9, fiber thickness and spacing was affected by electrospinning conditions, with all speeds and polymer concentrations yielding aligned fibers, but with a 5.0% PEUU in HFIP yielding optimal results.

Figure 10A:
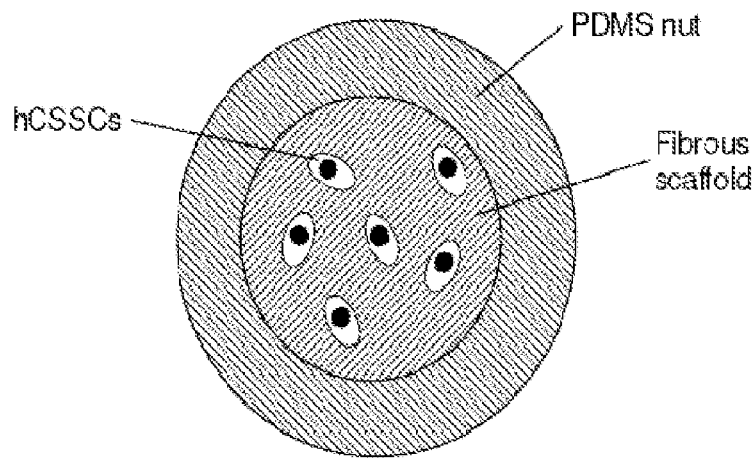
FIGS. 10A and 10B show, respectively a top and an elevated view of a cell culture chamber described in Example 2.
Figure 10B:
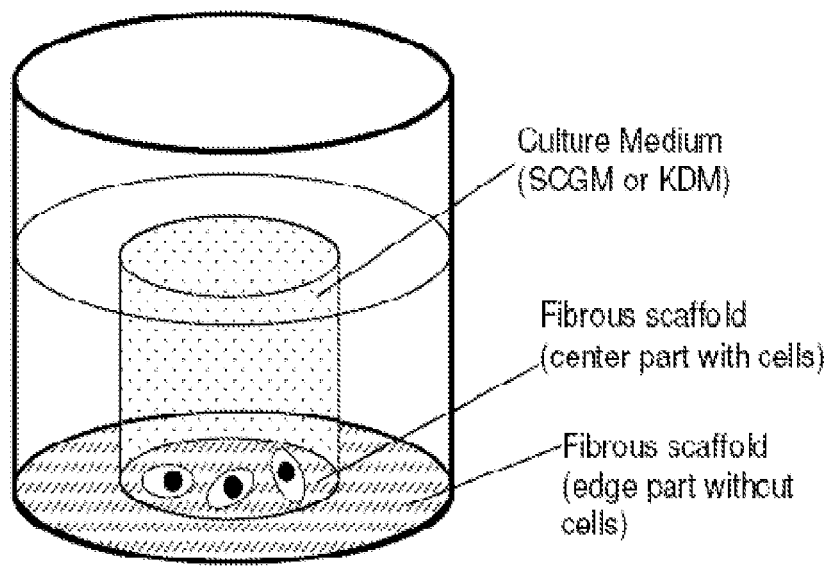

FIGS. 10A and 10B depict a cell culture device used in the experiments described. Culture conditions were essentially as described in Example 1.

Figure 11:
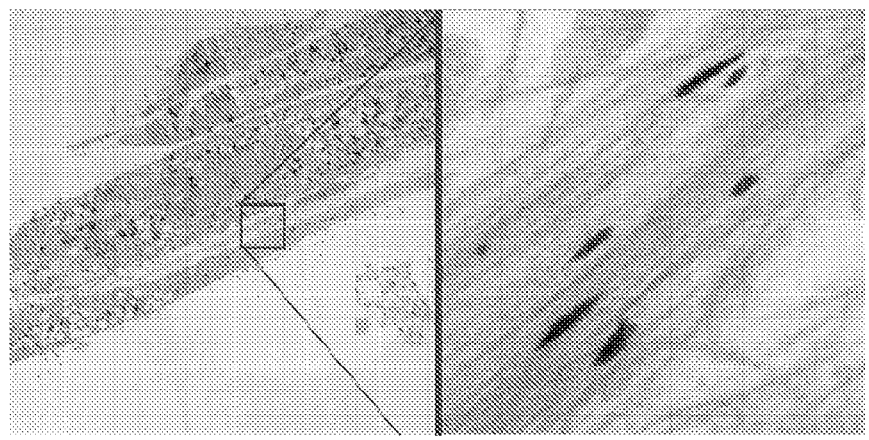
FIGS. 11 and 12 are TEM micrographs (axial cross section, FIG. 11 and cross section across the axis, FIG. 12) of cells grown according to Example 2.
Figure 12:
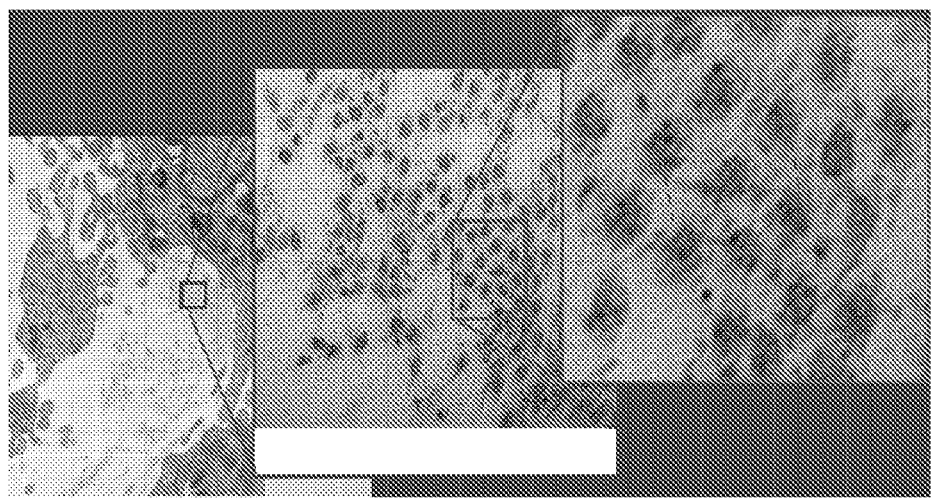

The scaffold material prepared from the 5% PEUU in HFIP at 2000 rpm was seeded with $8 \times 10^4$ cells/cm$^2$ hCSSCs prepared as described in Example 1 and cultured in stem cell medium for 3 days. KDM was added and the cells were examined 3 and 6 weeks later. At three weeks after the addition of the KDM, the cells were confluent as determined by SEM. Cells were microtomed along their long axis and were seen by TEM to be elongated and oriented (FIG. 11) and fiber structures characteristic of corneal stroma were seen when the cells were microtomed across their long axis (FIG. 12).

Figure 13:
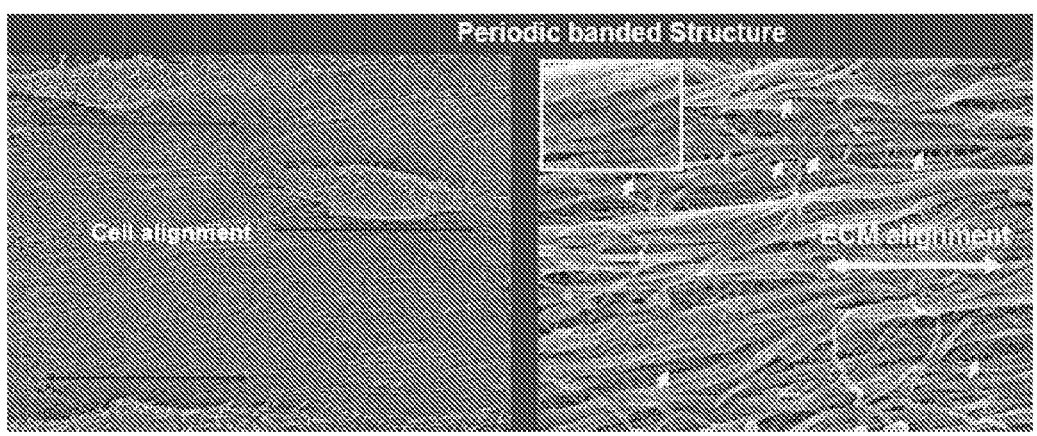
FIGS. 13 and 14 are SEM and TEM micrographs respectively of cells 6 weeks after differentiation. as described in Example 2.
Figure 14A:
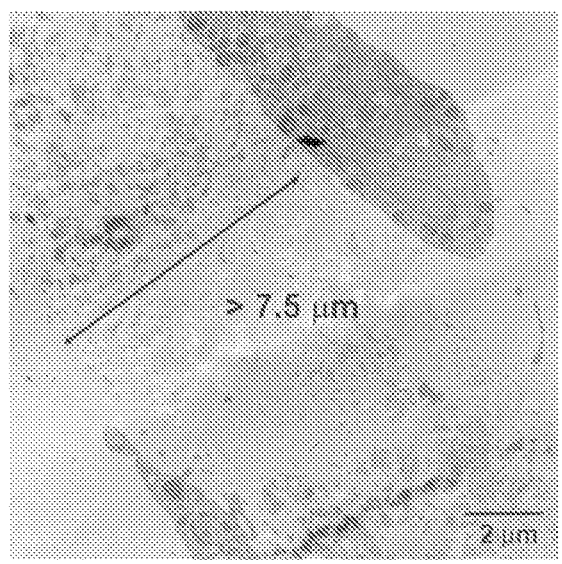
Figure 14B:
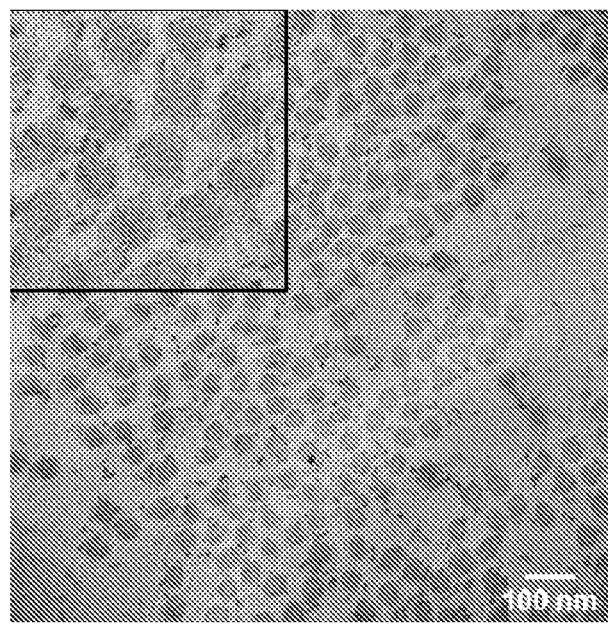
Figure 14C:
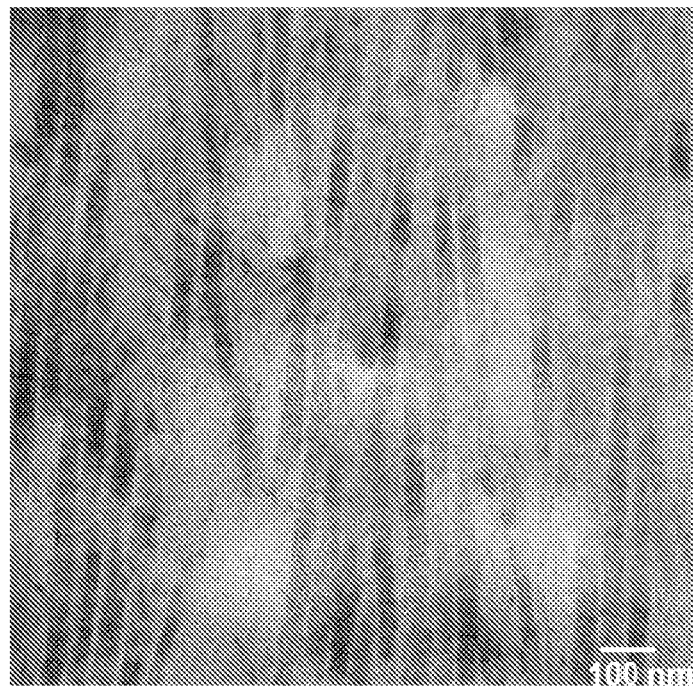
Figure 14D:
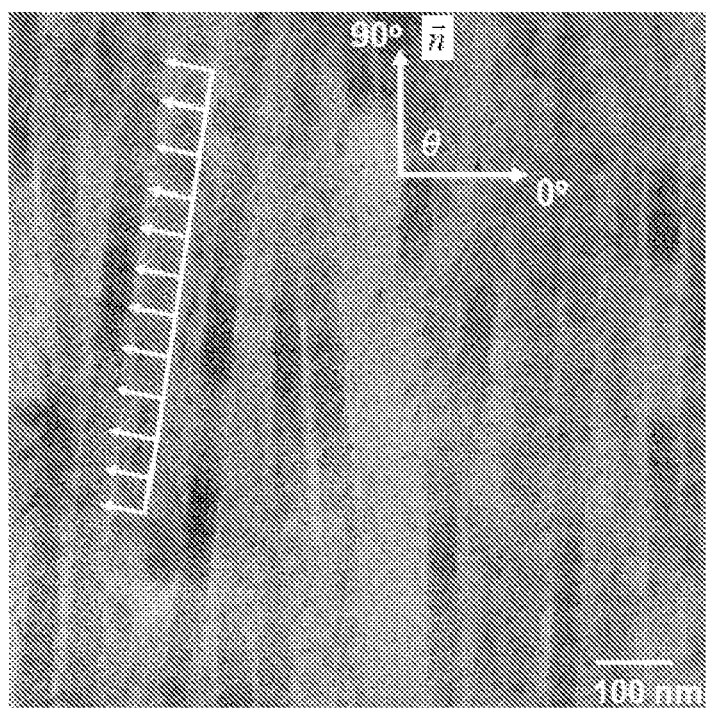
Figure 14E:
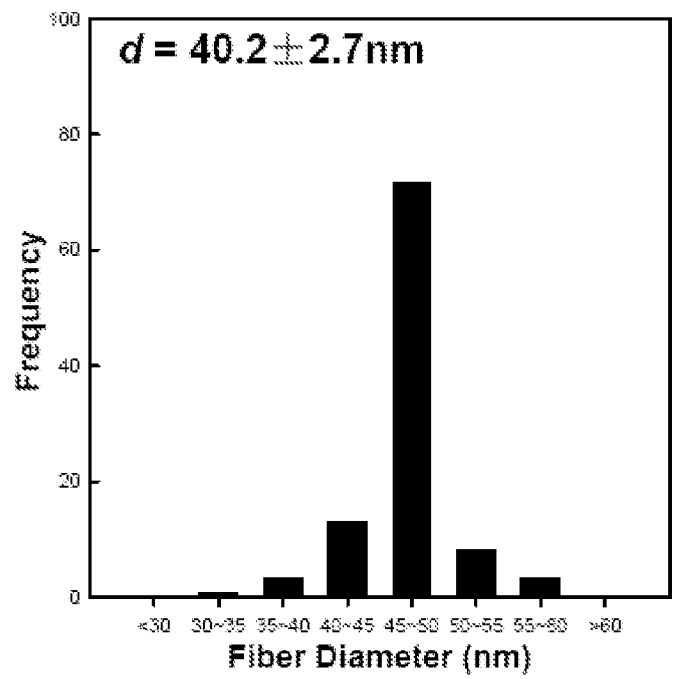
Figure 14F:
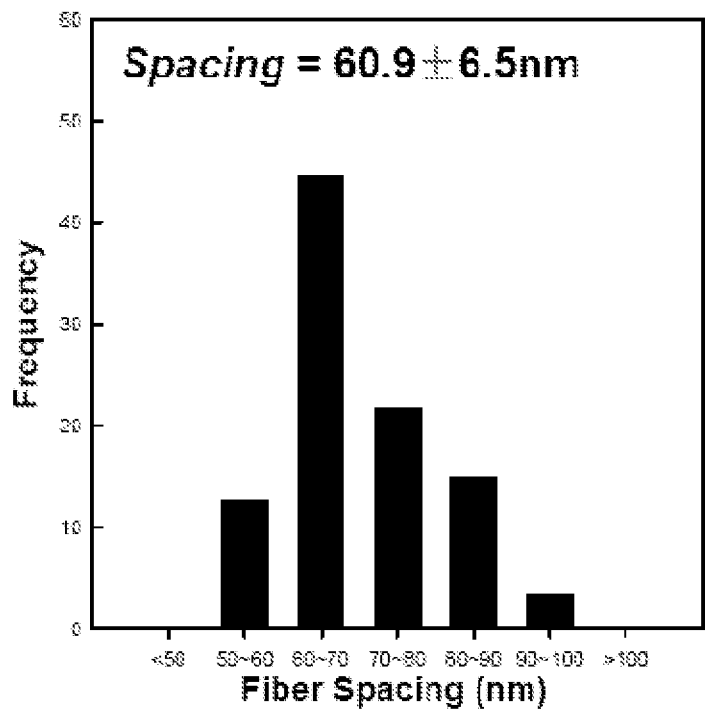
Figure 14G:
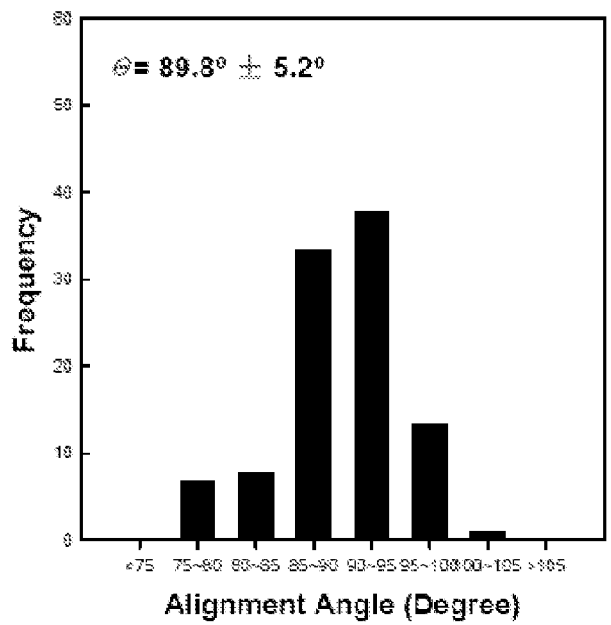

At six weeks after differentiation, the cells were examined by two-photon fluorescent microscopy showing highly-aligned cell structures. As shown in FIG. 13, SEM micrographs show extensive cell and ECM alignment. TEM shows uniform fiber size and characteristic pseudo-hexagonal lattice structures of corneal stroma (FIGS. 14A and 14B) with fiber banding (FIGS. 14C and 14D). FIGS. 14E and 14F provide graphs showing fiber diameter and spacing that is very close to that found in human corneal stroma. FIG. 14G provides a graph showing fiber orientation.

As a control, a cast film was prepared using the same PEUU composition, and no cell or fiber alignment was seen (data not shown). Immunohistochemical analysis was performed on the case film cells, and collagen, keratan sulfate and keratocan were present, but no aligned structure was produced (data not shown). In a related experiment, 0.0%, 5.0%, 10.0% and 20.0% type 1 collagen was added to the electrospun (performed as above) and cast substrates. Collagen in the template scaffolding was observed to have a detrimental effect on cell alignment and aligned scaffold formation over 12 weeks even though the initial templates appeared to have good quality aligned fiber structure (data not shown).

In summary:
  The aligned nano-fibrous scaffold prepared from biodegradable PEUU provided an amenable microenvironment where hCSSCs could secrete and organize a collagen type-I-based ECM into the lamellae with oriented fibers.

- The small and uniform fiber diameter and spacing were remarkably similar to that found in the human corneal stroma.
- The detected expression of collagen type-V, collagen type-VI, keratocan and keratan sulfate indicated that the resulting ECM mimicked human stroma-like tissue.
- The incorporation of Collagen Type-I in scaffold has a negative effect on the formation of oriented collagen type-I based fibrous ECM.
- The formed collagen type-I based fibrous ECM degenerated at the long-term culture (i.e. >12 week), probably due to the differentiated hCSSCs apoptosis(?).
- These data represent an important first step of a bottom-up strategy to bioengineer the human corneal stroma, and possibly a complete bioequivalent human cornea.

Example 3

Adipose-Derived Stem Cells Differentiate to Keratocytes In Vitro

Adipose-derived stem cells (ADSC) are an abundant population of adult stem cells with the potential to differentiate into several specialized tissue types, including neural and neural crest-derived cells. This study sought to determine if ADSC express keratocyte-specific phenotypic markers when cultured under conditions inducing differentiation of corneal stromal stem cells to keratocytes.

Methods

Cells and Materials: Human corneal stromal stem cells (CSSC) and corneal fibroblasts (CF) were isolated and cultured as previously described (Du Y, et al. Secretion and organization of a cornea-like tissue in vitro by stem cells from human corneal stroma. Invest Ophthalmol Vis Sci 2007; 48:5038-45 and Du Y, et al. Multipotent stem cells in human corneal stroma. Stem Cells 2005; 23:1266-75). Briefly, donor human corneas not usable for transplantation were incubated in 1.2 U/ml Dispase II (Roche Diagnostics, Pleasanton, Calif.) overnight at 4° C. Epithelial and endothelial cells were removed by dissection and debridement, and the stroma was minced into 2-mm cubes. Stromas were digested up to 3 h at 37° C. in Dulbecco's modified Eagle's medium (DMEM) containing 1 mg/ml collagenase type L (Sigma-Aldrich, St. Louis, Mo.). The resulting primary keratocytes were cultured in a humidified atmosphere containing 5% $CO_2$ in DMEM/F-12 (Sigma-Aldrich) with antibiotics for one week before harvesting for RNA. Stem cells from the stromal digest were expanded by culture at a density of $5 \times 10^3$ cells/$cm^2$ in a stem cell growth medium (SCGM) consisting of low glucose DMEM:MCDB201 60:40 containing 2% fetal bovine serum (FBS), 10 ng/ml epidermal growth factor (EGF), 10 ng/ml platelet derived growth factor BB (PDGF), 5 ug/ml insulin, 5 ug/ml transferrin, 5 ng/ml selenium, 200 U/ml LIF, and antibiotics/antimycotics. Fibroblastic differentiation was induced by 3 or more passages in DMEM/F-12 with 10% FBS.

Human subcutaneous adipose tissue was obtained from patients undergoing elective lipoaspiration surgery with informed consent under a protocol approved by the Institutional Review Board (IRB) of the University of Pittsburgh, consistent with the principles of the Declaration of Helsinki Adipose-derived stem cells were isolated by collagenase digestions and differential centrifugation as previously described (Aksu A E, et al. Role of gender and anatomical region on induction of osteogenic differentiation of human adipose-derived stem cells. Ann Plast Surg 2008; 60:306-22). Primary adipose-derived cell mixtures were cultured at $5 \times 10^4$ cells/$cm^2$ in SCGM. When the cells reached 80% confluency they were passaged 1:4 using trypsin. For flow cytometric analysis trypsinized ADSC were incubated at $1 \times 10^6$ cells/ml in DMEM with 5 µg/ml Hoechst 33342 dye for side population cell sorting (Du Y, et al. Multipotent stem cells in human corneal stroma. Stem Cells 2005; 23:1266-75) [23] and collected for further culture. Adipocyte differentiation medium contained DMEM with 17 µM D-pantothenic acid (Sigma-Aldrich), 0.5 µM dexamethasone (Sigma-Aldrich), 0.2 nM triiodothyronine (Sigma-Aldrich), and 1 µM ciglitazone (Enzo Life Sciences, Plymouth Meeting, Pa.). Chondrocyte differentiation was induced in DMEM/MCDB201, 2% FBS, 0.1 mM ascorbic acid-2-phosphate, 10-7 M dexamethasone, 10 ng/ml recombinant transforming growth factor beta 1 (TGFβ1; Sigma-Aldrich) and 100 µg/ml sodium pyruvate. Basal keratocyte differentiation medium (KDM) contained Advanced DMEM (Invitrogen, Rockville, Md.) supplemented with 10 ng/ml fibroblast growth factor 2 (FGF2) and 0.1 mM ascorbic acid-2-phosphate (A2P). Heparin-stripped, platelet-poor horse serum (HSHS) (Funderburgh J L, et al. Proteoglycan Expression during Transforming Growth Factor beta-induced Keratocyte-Myofibroblast Transdifferentiation. J Biol Chem 2001; 276:44173-8) was added as noted. Bovine corneal extract in DMEM/F-12 as an alternative to KDM was also used to compare keratocyte gene expression after induction (Musselmann K, et al. Isolation of a putative keratocyte activating factor from the corneal stroma. Exp Eye Res 2003; 77:273-9). Antibodies used included anti-keratocan peptide antibody (KeraC) (Funderburgh J L, et al. Keratocyte phenotype mediates proteoglycan structure: a role for fibroblasts in corneal fibrosis. J Biol Chem 2003; 278:45629-37) and J19 or J36 monoclonal antibodies to keratan sulfate (Du Y, et al. Multipotent stem cells in human corneal stroma. Stem Cells 2005; 23:1266-75). Secondary antibodies for western blotting, peroxidase-labeled antimouse and anti-rabbit IgG, were from Santa Cruz Biotechnology (Santa Cruz, Calif.). For fluorescence staining, Alexa Fluor 488 anti-mouse IgG and anti-rabbit IgG and nuclear dye TO-PRO-3 were obtained from Invitrogen.

Side Population Cell Sorting: ADSC were isolated as a side population on a high-speed cell sorter (MoFlo; Dako-Cytomation, Fort Collins, Colo.) using 350 nm excitation and 450 nm emission in a method similar to that previously described for corneal stromal stem cells (Du Y, Funderburgh M L, Mann M M, SundarRaj N, Funderburgh J L. Multipotent stem cells in human corneal stroma. Stem Cells 2005; 23:1266-75). Verapamil was added to validate side population isolation. After sorting, side population cells were cloned by limiting dilution, maintained in stem cell growth medium (SCGM) and passaged 1:3 by trypsinization when subconfluent.

Pellet and Fibrin Gel Culture: For pellet culture, $2 \times 10^5$ passage-4 ADSC were collected in a conical bottom 15-ml tube and centrifuged at 400×g for 5 min to form a pellet. The pellets were cultured in SCGM for 3 days, then transferred into various differentiation media which were changed every 3 days for up to 3 weeks. For fibrin gel culture, 33 µl suspension of $12 \times 10^6$ cells/ml passage-4 ADSC were seeded into a fibrin gel consisting of 134 µl of 5 mg/ml human fibrinogen (Sigma-Aldrich) and 33 µl of 100 U/ml bovine thrombin (Sigma-Aldrich). The gel formed in a cell culture incubator (37° C., 5% $CO_2$) for 1 h, and then SCGM containing 1 mg/ml ϵ-amino-N-caproic acid (Sigma-Aldrich) was added for 3 days. The medium was replaced with KDM containing ϵ-amino-N-caproic acid at day 3 and changed at 3-day intervals. Human corneal fibroblasts (CF)

(Du Y, et al. Stem cell therapy restores transparency to defective murine corneas. *Stem Cells* 2009; 27:1635-42) were used as control for pellet culture and fibrin gel culture. The CF were cultured under the same conditions as ADSC. Media were collected for western blot to detect the expression of keratocan and keratan sulfate after ion exchange isolation of proteoglycans (described below). Cells from the same cultures were lysed to make RNA for RT-PCR or quantitative PCR or were fixed for immunostaining Quantitative RT-PCR (qPCR): Cell pellets and cells in fibrin gels were stored in a stabilizing reagent (RNAlater; Invitrogen, Austin, Tex.) for 1 day. RNA was then isolated using the RNeasy mini kit (Qiagen, Valencia, Calif.), treated with DNase I (Invitrogen) and concentrated by alcohol precipitation. cDNA was transcribed from the RNA using SuperScript II reverse transcriptase (Invitrogen), following recommendations of the manufacturer. qPCR of cDNA was performed using assays containing fluorescent hybridization probes (TaqMan; Applied Biosystems, Foster City, Calif.) or with direct dye binding (SYBR Green; Applied Biosystems) as previously described (Du Y, et al. Secretion and organization of a cornea-like tissue in vitro by stem cells from human corneal stroma. *Invest Ophthalmol Vis Sci* 2007; 48:5038-45). Primers for SYBR assays were designed using online software (Primer 3) with the sequences shown in Table 2. Amplification of 18S rRNA was performed for each cDNA (in triplicate) for normalization of RNA content. A negative control lacking cDNA was also included in each assay. Relative mRNA abundance was calculated as the Ct for amplification of a gene-specific cDNA minus the average Ct for 18S expressed as a power of 2 ($2^{-\Delta\Delta Ct}$). Three individual gene-specific values thus calculated were averaged to obtain mean±SD.

TABLE 2

RT-PCR PRIMERS.

| Gene Name | GeneBank Accession No. | Primer sequence (5'→3') |
|---|---|---|
| Leptin | NM_000230 | Forward (SEQ ID NO: 1): TCCTGGATTCCTTTCCTTCA |
| | | Reverse (SEQ ID NO: 2): CAATCGAGGAGGGCAGAATA |
| Keratocan | NM_007035 | Forward (SEQ ID NO: 3): ATCTGCAGCACCTTCACCTT |
| | | Reverse (SEQ ID NO: 4): CATTGGAATTGGTGGTTTGA |
| ALDH3A1 | NM_001135168 | Forward (SEQ ID NO: 5): CATTGGCACCTGGAACTACC |
| | | Reverse (SEQ ID NO: 6): GGCTTGAGGACCACTGAGTT |
| 18S Ribosomal RNA | NR_003286 | Forward (SEQ ID NO: 7): CCCTGTAATTGGAATGAGTCCAC |
| | | Reverse (SEQ ID NO: 8): GCTGGAATTACCGCGGCT |

Western Blotting: Proteoglycans were recovered from culture media by ion exchange chromatography on microcolumns (SPEC-NH2; Agilent Technologies, Wilmington, Del.), as described previously (Du Y, et al. Multipotent stem cells in human corneal stroma. Stem Cells 2005; 23:1266-75). Proteoglycans were digested with a mixture of keratanase II and endo-β-galactosidase. Digested and undigested samples were run on a 4%-20% SDS-PAGE gel, transferred to polyvinylidene difluoride (PVDF) membrane and subjected to immunoblotting with KeraC antibody against keratocan (Funderburgh J L, et al. Proteoglycan Expression during Transforming Growth Factor beta-induced Keratocyte-Myofibroblast Transdifferentiation. *J Biol Chem* 2001; 276:44173-8) and antibody J36 against keratan sulfate (Du Y, et al. Secretion and organization of a cornea-like tissue in vitro by stem cells from human corneal stroma. Invest Ophthalmol Vis Sci 2007; 48:5038-45).

Histology: Monolayer cells were rinsed briefly in phosphatebuffered saline (PBS), fixed for 12-15 min in 3% paraformaldehyde in PBS at room temperature, and rinsed in PBS. Oil red 0 (Sigma-Aldrich) was prepared at 0.5% in isopropanol, diluted to 0.3% in water and filtered before use. Cells were stained with oil red 0 for 15 min and rinsed with 60% isopropanol followed by hematoxylin stain for nuclei. Bright-field micrography was performed with a 40× oil objective. Pellets and fibrin gels were rinsed briefly in PBS, fixed for 15 min in 3% PFA in PBS at room temperature, rinsed in PBS, embedded in optimal cutting temperature embedding compound (Tissue-Tek OCT; Electron Microscopy Sciences, Hatfield, Pa.), frozen, and stored at −20° C. until they were cut as 8-μm sections on a cryostat. Sections were hydrated in PBS before staining. Nonspecific binding was blocked with 10% heat-inactivated goat serum. Sections were incubated for 1 h at room temperature with primary antibodies. After two rinses in PBS, secondary antibodies and nuclear counterstain (TO-PRO-3; Invitrogen) were added for 1 h at room temperature. The samples were photographed using a confocal microscope with a 20× oil objective (Bio-Rad Laboratories, Hercules, Calif.).

Results

Figure 15:
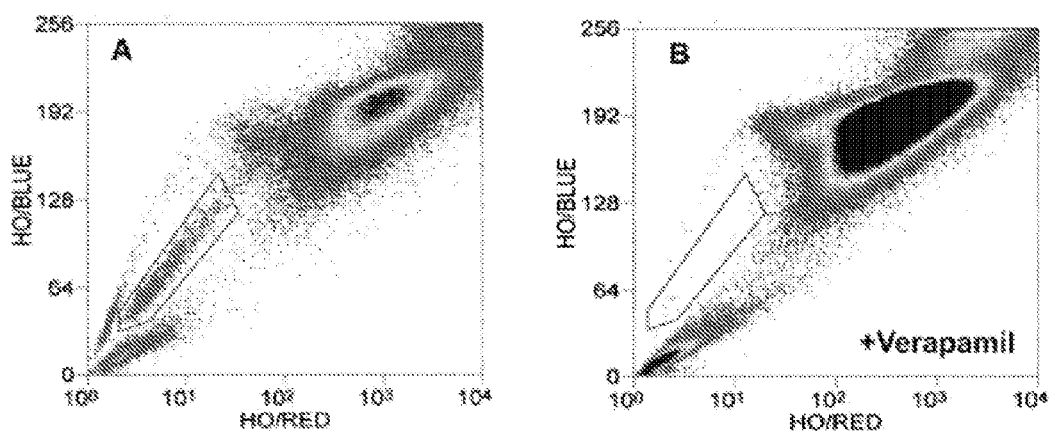
FIG. 15. Flow cytometric identification of side population from cultured human adipose-derived stem cells (ADSC). A: Passage-two ADSC stained with Hoechst 33342 were analyzed using 350-nm excitation with blue (635 nm) and red (488 nm) emission. Cells showing reduction of both blue and red fluorescence (side population cells) were analyzed as defined by the box outlined on the left. B: An analysis similar to (A) but with a preincubation in 50 µM verapamil before incubation with Hoechst 33342.

Side Population Cells in ADSC: Human ADSC isolated by collagenase and differential centrifugation were labeled with Hoechst 33342 dye and analyzed using flow cytometry to identify side population cells (FIG. 15). This technique originally described by Goodell et al. (Isolation and functional properties of murine hematopoietic stem cells that are replicating in vivo. *J Exp Med* 1996; 183:1797-806) identifies cells that efflux the Hoechst 33342 dye as a result of the expression of ATP-binding cassette (ABC) transporter proteins. Side population cells are present in small numbers in many tissues and have been found to exhibit adult stem cell-like properties (Zhou S, et al. The ABC transporter Bcrp1/ABCG2 is expressed in a wide variety of stem cells and is a molecular determinant of the side-population phenotype. *Nat Med* 2001; 7:1028-34 and Challen G A, et al. A side order of stem cells: the SP phenotype. *Stem Cells* 2006; 24:3-12). FIG. 15A demonstrates that a population (defined by the box) amounting to less than 1% of the total cells shows reduced Hoechst 33342 dye staining and a color shift toward blue in the cultured ADSC. When we preincubated with verapamil, an inhibitor of ABC transporter function, the population was eliminated (FIG. 15B). The presence of this characteristic side population suggests the presence of multipotent adult stem cells in the ADSC.

Figure 16:
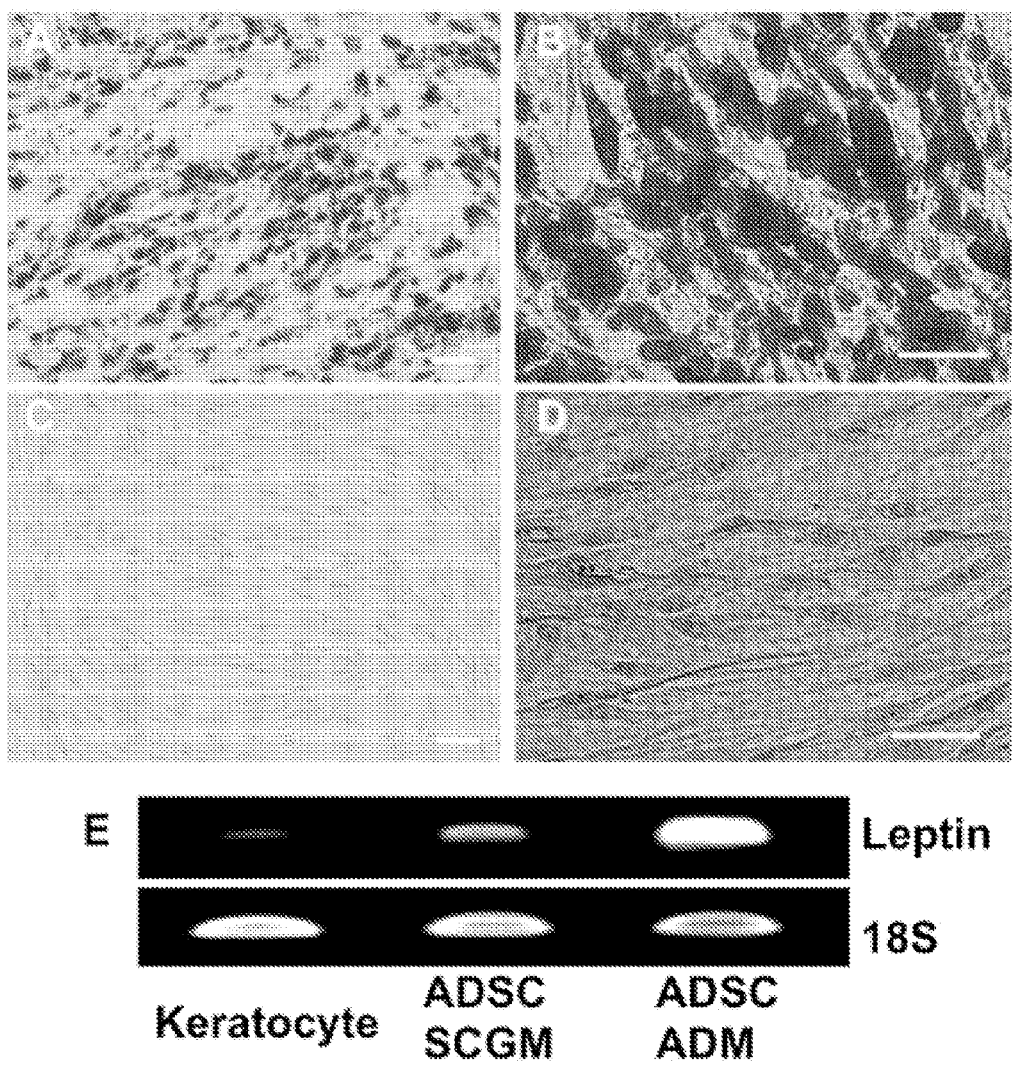
FIG. 16. Induction of adipocytes from ADSC. ADSC were induced to differentiate into adipocytes in ADM for two weeks as described in Methods. A, B: ADSC were fixed and stained with Oil Red O. C, D: ADSC without induction were stained with Oil Red O as control. E: mRNA for leptin was detected by RT-PCR. Leptin expression (Upper) and 18S (Lower). Lane 1, uncultured keratocytes; lane 2, ADSC; lane 3, ADSC in adipocyte induction medium. Scale bars: 100 µm (A, C); 50 µm (B, D).

Differentiation Potential of ADSC: To demonstrate multipotent differentiation potential, ADSC were expanded and grown in under conditions that induce differentiation to mature adipocytes in adult stem cells. FIG. 16A,B shows staining with oil red O, which stains the characteristic neutral triglycerides and lipids in adipocytes. Well defined lipid droplets were present within differentiated cells. FIG. 16C,D shows the lack of oil red O staining in ADSC cultured in SCGM. Expression of the leptin gene encoding an adipokine secreted by mature adipocytes was increased in ADSC after culture in ADM (FIG. 16C). Leptin was minimally expressed by keratocytes, but was upregulated in multipotent stromal corneal stem cells as well as in ADSC.

Figure 17:
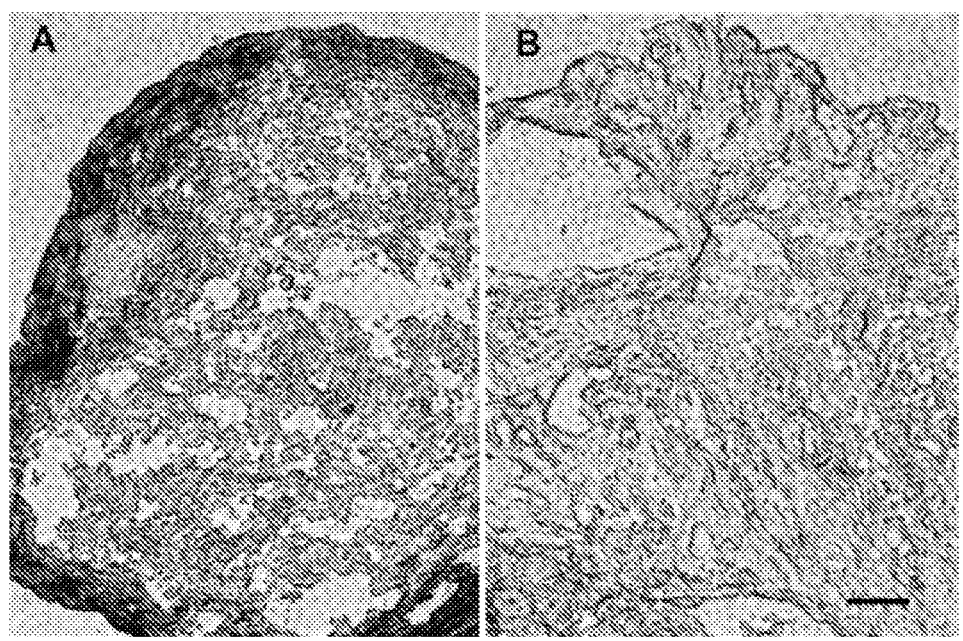
FIG. 17. Induction of cartilage matrix expression by ADSC. ADSC (A) and CF (B) were cultured as pellets (2×105) in chondrocyte differentiation medium for three weeks. The pellets were fixed, imbedded in OCT, cut into 8 µm thick sections and stained with toluidine blue to detect proteoglycan staining typical of cartilage. Scale bar indicates 50 µm.
Figure 18:
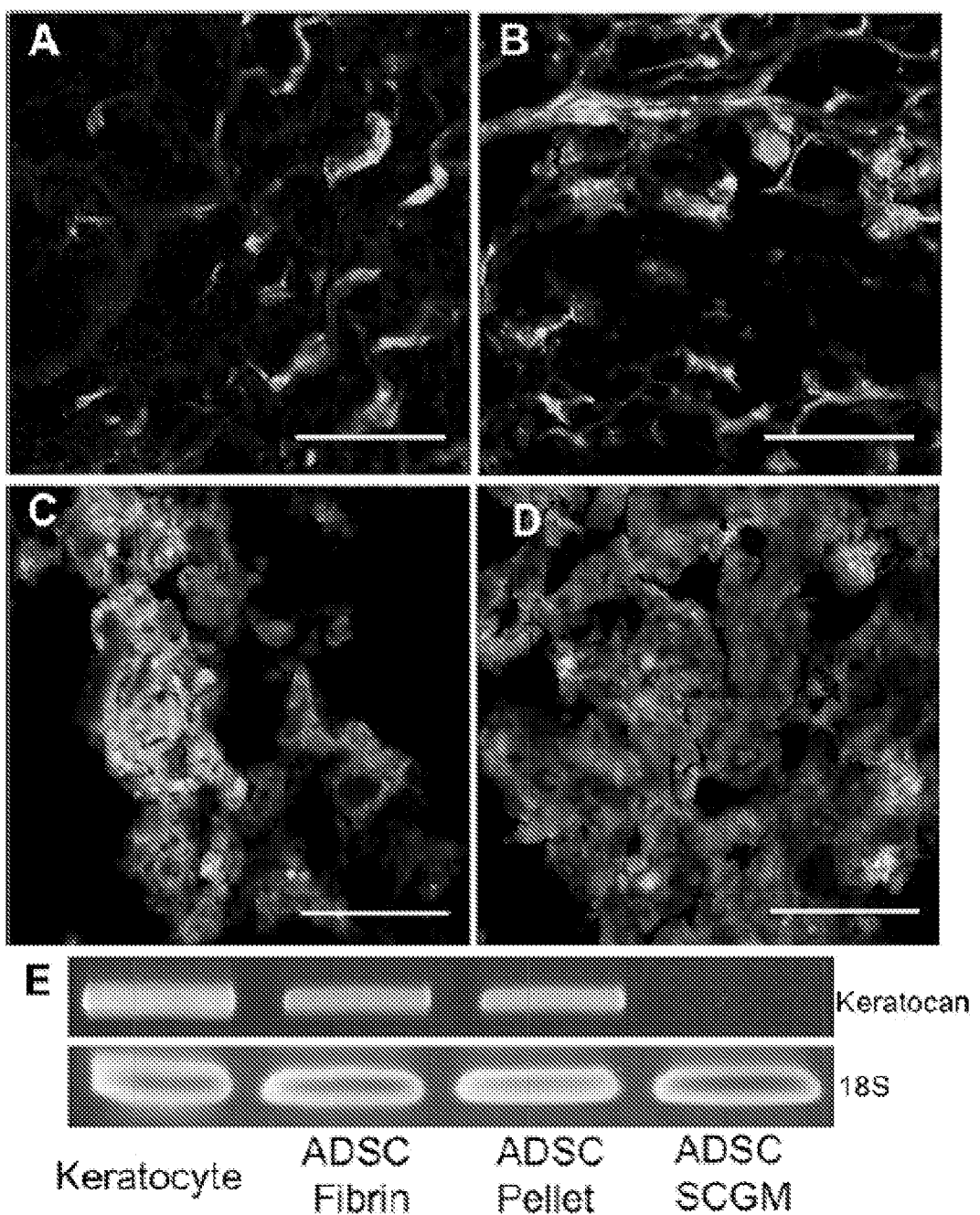
FIG. 18. Induction of keratocyte markers in ADSC. A, B: ADSC were cultured in fibrin gels for 3 weeks in keratocyte differentiation medium. C, D: ADSC were cultured as pellet for 3 weeks in keratocyte differentiation medium. Immunofluorescent staining shows the presence of keratan sulfate with antibody J19 (green; A, C) or keratocan with antibody KeraC, (green; B, D). Red shows nuclear staining by propidium iodide. E: RT-PCR shows keratocan expression in (left to right) uncultured keratocytes (positive control), ADSC in fibrin gel, ADSC as pellet culture, ADSC in SCGM. Scale bars=20 µm.
Figure 19:
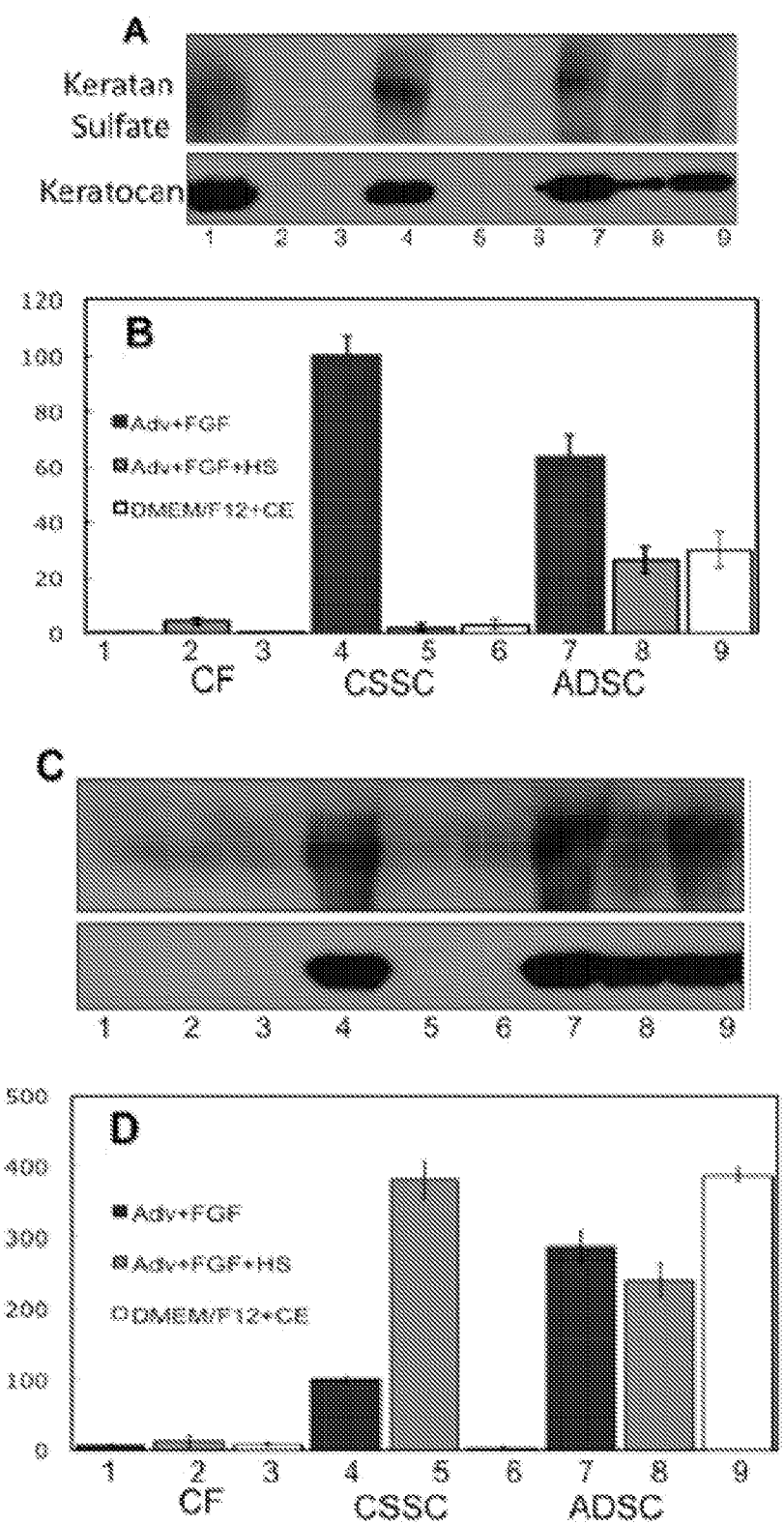
FIG. 19. Keratan sulfate, keratocan protein, and mRNA expression by CSSC, ADSC, and CF in different media. A, B: Fibrin gel cultures after 3 weeks. C, D: Pellet cultures after 3 weeks. A and C are western blots showing keratan sulfate and keratocan. B and D show qPCR data of keratocan mRNA. Samples 1-3: CF, 4-6: CSSC cells; 7-9, ADSC cells. Samples 1, 4, 7: keratocyte differentiation medium; Samples 2, 5, 8: keratocyte differentiation medium+1% HSHS. Samples 3, 6, 9: DMEM/F-12 medium with bovine corneal extract (1:10). Expression of mRNA is shown normalized to monolayer of CSSC in keratocyte differentiation medium=100.

ADSC were also cultured under conditions reported to induce chondrogenic differentiation. After 3 weeks in chondrocyte differentiation medium, as shown in FIG. 17A, ADSC secreted cartilage matrix as indicated by positive toluidine blue staining for proteoglycans characteristic of cartilage. In contrast, CF grown in pellet culture did not display chondrogenic differentiation as evidenced by absence of toluidine blue staining (FIG. 17B). Expression of keratocyte markers: Given the clear multipotent nature of ADSC, we investigated the ability of these cells to assume a keratocyte phenotype using methods previously successful in differentiating human corneal stromal stem cells into keratocytes (Du Y, et al. Secretion and organization of a cornea-like tissue in vitro by stem cells from human corneal stroma. *Invest Ophthalmol Vis Sci* 2007; 48:5038-45). ADSC were seeded in fibrin gels (FIG. 18A,B) and cultured as pellets (FIG. 18C,D) and transferred into KDM for 3 weeks. Immunostaining of ADSC cultures the showed presence of the stroma-specific ECM molecules keratocan and keratan sulfate in both the fibrin gels and pellets (FIG. 18). ADSC in fibrin gels were more sparsely distributed (FIG. 18A,B) than in the pellet cultures (FIG. 18C,D). Expression of keratocan in ADSC incubated in KDM was confirmed with RT-PCR using human keratocan primers (FIG. 18E). ADSC maintained in SCGM alone did not express keratocan mRNA. In addition, we observed (not shown) that ADSC in KDM formed extensive cell-cell contacts similar to those connecting keratocytes. Cultures using both fibrin gel and pellet methods induced ADSC differentiation into keratocyte-like cells. After we established the differentiation potential of ADSC into cells synthesizing keratocyte-specific proteins, we examined the effects of varying culture conditions on both keratocan and keratan sulfate expression levels. Using a combination of three different culture media and fibrin gel or pellet culture, we found that ADSC in pellet cultures (FIG. 19C,D) had more consistent expression of both keratocan and keratan sulfate at the protein and mRNA level than ADSC in fibrin gels (FIG. 19A,B). This was similar to human CSSC, which have elevated keratocan expression in pellet cultures compared to fibrin gel culture (FIG. 19A,B) (Du Y, et al. Secretion and organization of a cornea-like tissue in vitro by stem cells from human corneal stroma. *Invest Ophthalmol Vis Sci* 2007; 48:5038-45). In fact, the level of keratocan mRNA in ADSC in pellet culture was similar to that of stem cells from corneal stroma (CSSC; FIG. 19D). Bovine corneal extract appeared to enhance differentiation of the ADSC but had little effect on CSSC (FIG. 19, samples 6 and 9).

Figure 20:
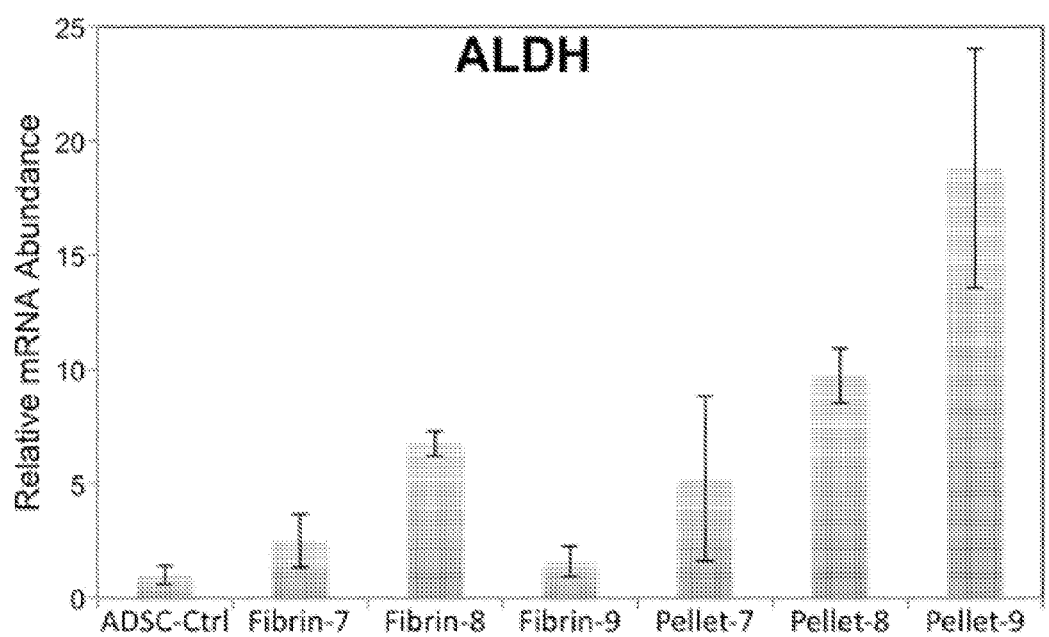
FIG. 20. ALDH is upregulated in ADSC cultured under conditions that induce keratocyte differentiation. Expression of ALDH3A1 was compared in ADSC cells cultured as described in FIG. 19 using qPCR as described in Methods. Expression levels were normalized to that of ADSC in SCGM (ADSC-Ctrl) in samples in Fibrin or Pellets under conditions 7, 8, 9 as described in FIG. 19.

The gene ALDH3A1 codes for the widely distributed protein aldehyde dehydrogenase (ALDH). In differentiated cells of the cornea, however, ALDH is exceptionally abundant, especially in keratocytes, where it makes up as much as 40% of soluble protein (Jester J V, et al. The cellular basis of corneal transparency: evidence for 'corneal crystallins'. *J Cell Sci* 1999; 112:613-22). Previously we observed ALDH to be markedly upregulated as CSSC differentiate to keratocytes (Du Y, et al. Secretion and organization of a cornea-like tissue in vitro by stem cells from human corneal stroma. *Invest Ophthalmol Vis Sci* 2007; 48:5038-45) thus, we would expect ALDH upregulation if ADSC are adopting keratocyte phenotype. In FIG. 20 we documented strong upregulation of this corneal marker mRNA, particularly in the pellet cultures of ADSC.

Figure 21:
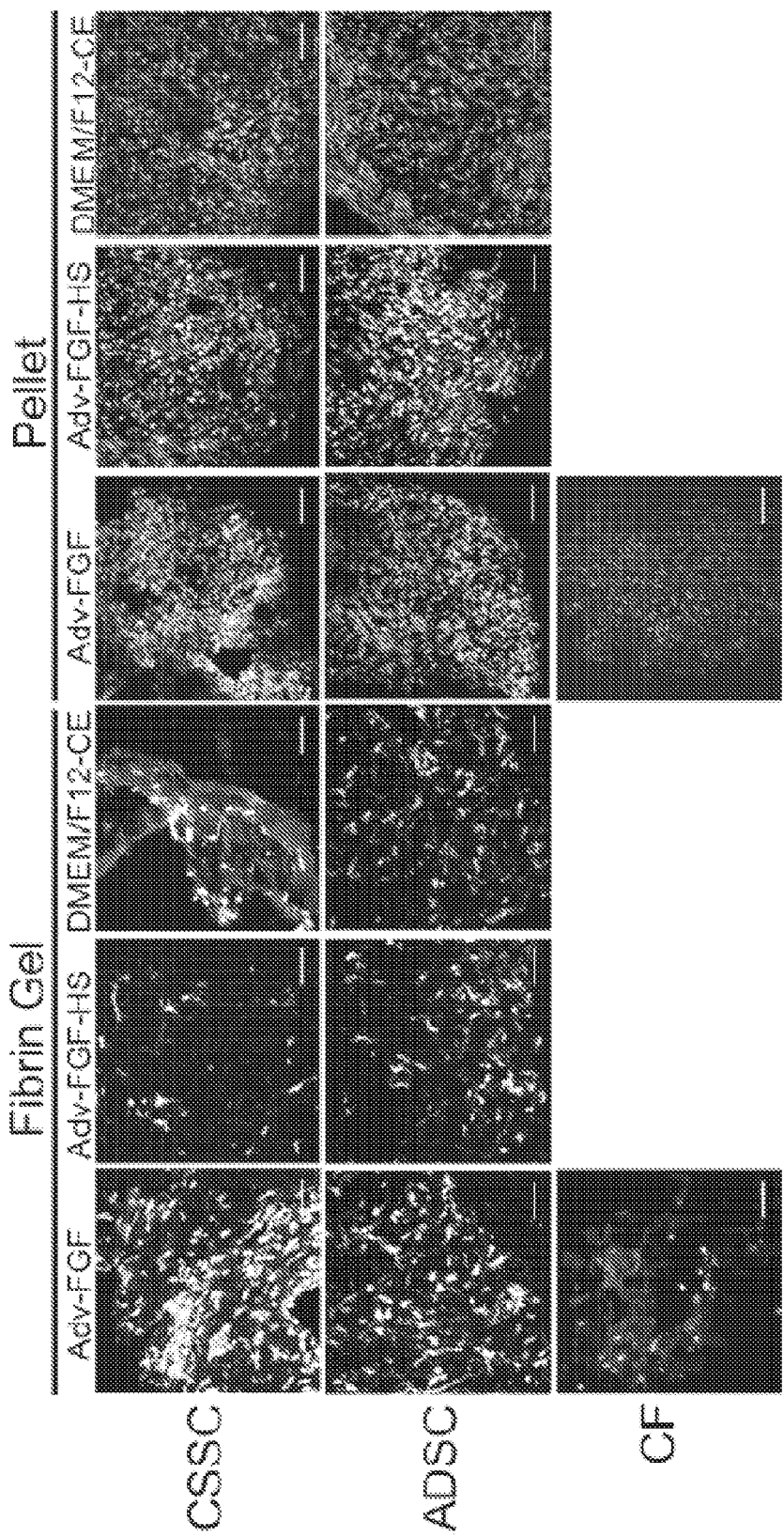
FIG. 21. Keratan sulfate staining in CSSC, ADSC, and CF cultured in fibrin gels or as pellets in different media. Frozen sections of pellet and fibrin gel cultures were stained with antibody J19 against keratan sulfate (green) and nuclei (red) after 3 weeks of culture in different media. Abbreviations: CSSC: corneal stromal stem cells, ADSC: Adipose-derived stem cell, Adv: Advanced DMEM, FGF: fibroblast growth factor 2, HS: heparin stripped horse serum, CE: bovine corneal extract. Scale bars=50 µm.
Figure 22:
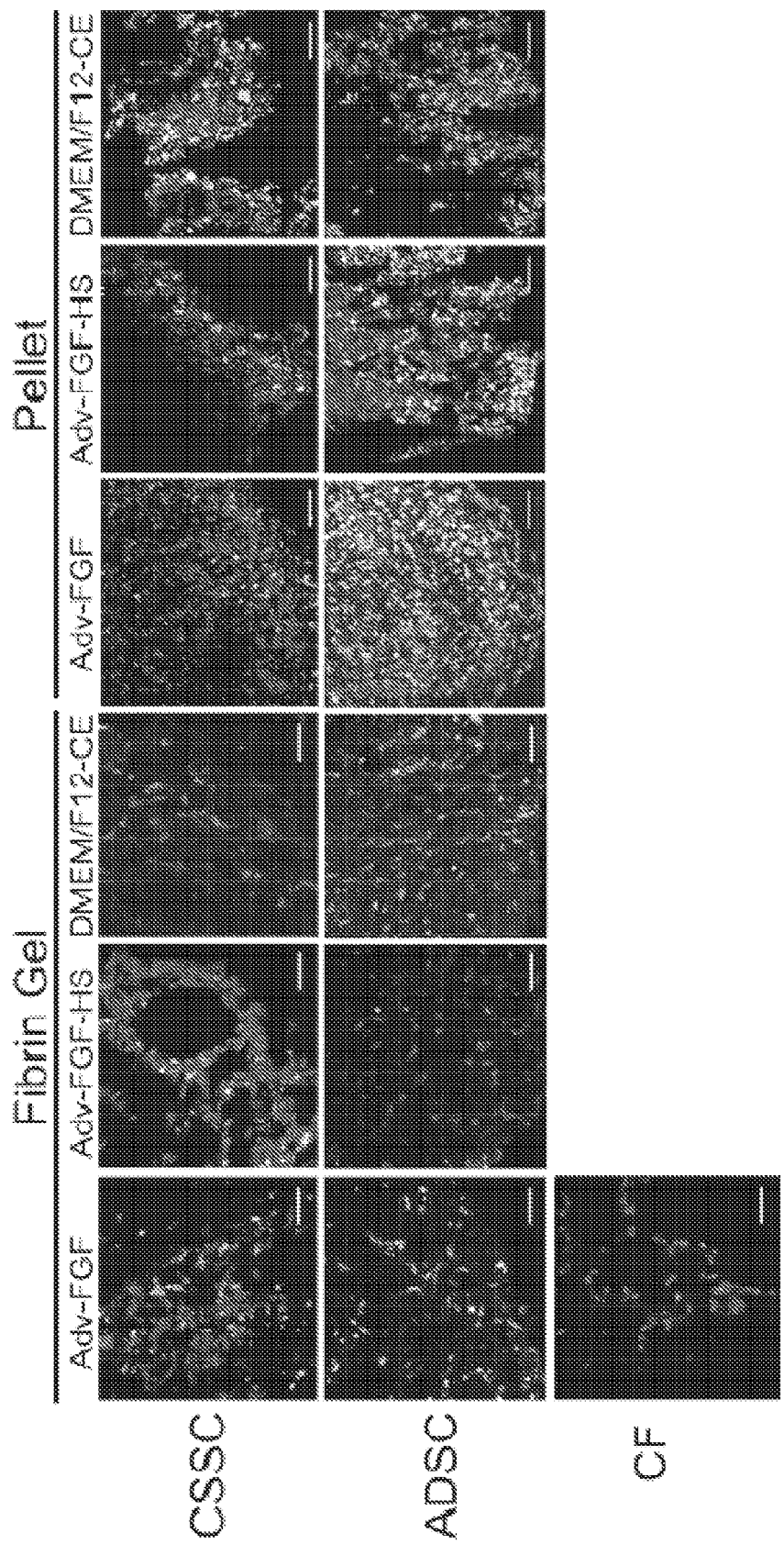
FIG. 22. Keratocan staining in CSSC, ADSC, and CFs cultured in different media. Frozen sections of pellet and fibrin gel cultures were stained with antibody KeraC for keratocan (green) and cell nuclei (red) after 3 weeks of culture in several different media. Abbreviations: CSSC: corneal stromal stem cells, ADSC: Adipose-derived stem cell, Adv: Advanced DMEM, FGF: fibroblast growth factor 2, HS: heparin stripped horse serum, CE: bovine corneal extract. Scale bar=50 µm.

Immunostaining of keratan sulfate (FIG. 21) and keratocan (FIG. 22) demonstrated that the mRNA increases documented in FIG. 19 correlate with accumulation of these keratocyte-specific markers in the ECM of the cultures. Consistent with mRNA levels, accumulation of these matrix molecules was more evident in pellet cultures, and CSSC and ADSC generated similar amounts. This result was in contrast to CF which did not consistently synthesize keratocan or keratan sulfate when grown in either fibrin gels or pellets.

In this study we have shown that ADSC isolated from lipoasiprate have the potential to differentiate in vitro into cells that synthesize and secrete keratocyte-specific proteins as confirmed by both immunohistochemical and molecular evidence. Throughout our study we used ADSC grown and expanded at clonal density. These cells were cultured in various differentiation conditions while maintaining their ability to differentiate into adipocyte (FIG. 16) and chondrocyte (FIG. 17) lineages similar to results reported previously (Zuk P A, et al. Human adipose tissue is a source of multipotent stem cells. Mol Biol Cell 2002; 13:4279-95). In addition, we show that ADSC grown in three-dimensional fibrin gel and pellet culture systems supplemented with appropriate differentiation medium can be induced to differentiate into a keratocyte lineage (FIG. 18, FIG. 19, and FIG. 20). This differentiation is evidenced by the high levels of cornea-specific keratocan mRNA and protein expression and the increased presence of keratan sulfate in the culture medium. Expression of aldehyde dehydrogenase 3 family, member A1 (ALDH3A1), keratocan, and keratan sulfate by ADSC was observed in several different media and in both culture formats.

Our previous work showed that keratan sulfate is $10^3$ to $10^6$ fold more enriched in cornea than any other tissue (Funderburgh J L, et al. Distribution of proteoglycans antigenically related to corneal keratan sulfate proteoglycan. *J Biol Chem* 1987; 262:11634-40) and that synthesis of keratan sulfate by keratocytes is highly regulated in vitro and in vivo (Long C J, et al. Fibroblast growth factor-2 promotes keratan sulfate proteoglycan expression by keratocytes in vitro. *J Biol Chem* 2000; 275:13918-23; Funderburgh J L, et al. Synthesis of corneal keratan sulfate proteoglycans by bovine keratocytes in vitro. *J Biol Chem* 1996; 271:31431-6; and Beales M P, et al. Proteoglycan synthesis by bovine keratocytes and corneal fibroblasts: maintenance of the keratocyte phenotype in culture. *Invest Ophthalmol Vis Sci* 1999; 40:1658-63). Keratan sulfate biosynthesis in vitro, therefore, represents the most stringent marker of the keratocyte phenotype yet described. The observation that ADSC can be induced to produce keratan sulfate is novel and presents the best evidence to date that these cells can adopt the keratocytes phenotype. Keratocan is highly enriched in keratocytes, as is ALDH3A1. Neither of these proteins represents a unique corneal marker but like keratan sulfate, both, are highly expressed in keratocytes and upregulated as CSSC differentiate to keratocytes (Du Y, et al. Secretion and organization of a cornea-like tissue in vitro by stem cells from human corneal stroma. *Invest Ophthalmol Vis Sci* 2007; 48:5038-45). Upregulation of keratocan and ALDH3A1 mRNA simultaneously with synthesis of keratan sulfate by ASSC strengthens the argument that these cells are indeed differentiating to keratocytes.

High cell density, as occurs in pellet cultures, rather than dendritic cell morphology, appeared to positively influence keratocyte differentiation potential. The pellet cultures produced a denser, more abundant ECM with higher keratocan and keratan sulfate. This is similar to what we observed in human CSSC, which differentiate and express higher levels of keratocan and keratan sulfate in pellet cultures (Du Y, et al. *Invest Ophthalmol Vis Sci* 2007; 48:5038-45 and Funderburgh M L, et al. Keratocyte phenotype is enhanced in the absence of attachment to the substratum. *Mol Vis* 2008; 14:308-17). Compared to fibrin gels, ADSC expressed higher keratocan and keratan sulfate in pellet cultures (FIG. 19). Although pellet cultures clearly influenced keratocan expression, the addition of extra supplementary factors such as horse serum and bovine extract did not appear to significantly enhance levels of keratocan protein. Thus, keratocyte differentiation of ADSC appears to be more dependent on the three-dimensional culture environment and less dependent on exogenous molecular supplementation. Growth of differentiated keratocytes based on the architecture of the culture conditions, rather than a complicated menu of biologically active molecules, may be advantageous to the future isolation and production of clinically useful cells while lowering the risk of contaminants from additions.

ADSC are an abundant and readily accessible source of multipotent adult stem cells with the desirable potential for autologous cell therapy, thereby presenting the potential for personal tissue engineering of the corneal stroma. A recent study by Arnalich-Montiel et al. (Adipose-derived stem cells are a source for cell therapy of the corneal stroma. *Stem Cells* 2008; 26:570-9) demonstrated that human lipoaspirate-derived cells could be transplanted into the corneal stroma of rabbits. Under these conditions, the ADSC did not elicit a significant immune response, remained viable, and could be immunostained for ALDH and keratocan. The current study builds on these findings, using the more stringent keratocyte phenotypic marker keratan sulfate and defining in vitro conditions under which the keratocyte phenotype is expressed by these cells. Understanding these conditions will allow development of use of ADSC in stromal bioengineering applications.

The immunomodulatory effects of ADSC are another important aspect of their potential use in cell based therapy. These effects have been attributed to a lack of HLA-DR expression and active suppression of the proliferative T-cell response (McIntosh K, et al. The immunogenicity of human adipose-derived cells: temporal changes in vitro. *Stem Cells* 2006; 24:1246-53). ADSC have been shown to enhance dermal wound healing by the secretion of a variety of soluble growth factors accelerating wound repair and regeneration (Kim W S, et al. Wound healing effect of adipose-derived stem cells: a critical role of secretory factors on human dermal fibroblasts. *J Dermatol Sci* 2007; 48:15-24). In addition, ADSC were shown to increase wound healing through differentiation into cell types capable of replacing and regenerating damaged tissue (Altman A M, et al. IFATS collection: Human adipose-derived stem cells seeded on a silk fibroin-chitosan scaffold enhance wound repair in a murine soft tissue injury model. *Stem Cells* 2009; 27:250-8). The biologic effect these soluble factors have in corneal wounds remains to be determined, but could include production of the correct ECM and maintenance of a keratocyte phenotype. Particularly relevant to the environmental exposures of the cornea, ADSC have been shown to provide protective antioxidant effects against chemically- and UVB-induced reactive oxygen species (Kim W S, et al. Evidence supporting antioxidant action of adipose-derived stem cells: protection of human dermal fibroblasts from oxidative stress. *J Dermatol Sci* 2008; 49:133-42 and Kim W S, et al. Antiwrinkle effect of adipose-derived stem cell: activation of dermal fibroblast by secretory factors. *J Dermatol Sci* 2009; 53:96-102).

Example 4

Adipose-Derived Stem Cells Cultured on Tissue Engineered 3-D Orderly Collagen Nanoconstruct Differentiate to Keratocytes In Vitro Adipose-derived stem cells (ADSC) are an abundant population of adult stem cells readily isolated from human adipose tissue. ADSC have multilineage potential and they are able to differentiate into fat, bone, cartilage, and muscle under lineage-specific culture condition. This study sought to determine if ADSC could be guided by aligned nanofibrous substance to biosynthesize the bioequivalent of human cornea stromal tissue employing corneal tissue engineering strategy. We investigated if ADSC expressed keratocyte-specific phenotypic markers when cultured under condition inducing differentiation of corneal stromal stem cells to keratocytes.

Materials and Methods

Scaffold Preparation

Biodegradable Poly(ester urethane)urea (PEUU) was prepared. First, 1,4-diisocyanatobutane and polycaprolactonediol (PCL, $M_w$=2 kg/mol) were reacted in dimethyl sulfoxide (DSMO, Anhydrous Grade) for three hour at 75° C. with the aid of Tin 2-ethylhexanoate under the protection of $Ar_2$ purge. After cooling down to room temperature, the oligomer solution was drop-wise added by 1,4-diaminobutane under vigorous stiffing. After 18 hour reaction at room temperature, the polymer solution was precipitated in distilled water. Then the precipitant was soaked in anhydrous 2-propanol for another 48 hours to remove DMSO and unbound monomers. The yielded polymer was incubated in anhydrous ethanol for another 24 hours to remove water, and then further dried under vacuum at 40° C. for one week in order to remove water residual. The yielded product is a white elastomer.

The oriented nanofibrous scaffolds were prepared by electrospinning Briefly, PEUU was dissolved in hexafluoroisopropanol (HFIP) under mechanical stiffing at room temperature. The obtained polymer solution was fed by syringe pump (Harvard Apparatus) into a steel capillary (I.D.=0.047 inch) suspended on an aluminum wheel collector with 2-cm in width and 20-cm in thickness. A combination of two high-voltage generators (Gamma high Voltage Research) was employed with a high positive voltage (+10 kV) to charge the steel capillary containing polymer solution, and a high negative voltage (−5 kV) to charge the aluminum wheel collector with 20 cm in diameter. The distance between the tip of the steel capillary and the top of the aluminum wheel collector is 15 cm. The volume flow rate was set up as 1 ml/hr. The PEUU solution was electrospun with 5.0 wt % concentration and rotational speed is 2000 rpm. The yielded fibrous scaffold is approximate 200 micron thick.

Cell Cultures

The scaffold was punched into round discs with 25-mm in diameter to fit in 24-well culture plate. The discs were sterilized by UV exposure (254 nm) in cell culture hood for 20 minute each side. Discs were fixed in each well with plastic nuts and primary adipose-derived stem cells (ADSCs) were seeded on the scaffolds at a density of $1.6 \times 10^5$ cells/well, which were incubated in stem cell growth medium (SCGM) containing DMEM/MCDB-201 with 2% fetal bovine serum (FBS), 10 ng/ml DMEM/MCDB-201 with 2% fetal bovine serum (FBS), 10 ng/ml epidermal growth factor, 10 ng/ml platelet-derived growth factor (PDGF-BB), 5 µg/ml insulin, 5 µg/ml transferrin, 5 ng/ml selenous acid (ITS), 1,000 units per ml leukemia inhibitory factor (LIF), ×1 linoleic acid-bovine serum albumin (LA-BSA), 0.1 mM ascorbic acid-2-phosphate, 10-8 M dexamethasone, 100 IU/ml penicillin, 100 µg/ml streptomycin, 50 µg/ml gentamicin, and 1.25 µg/ml amphotericin B. Total of 48 scaffolds were prepared.

72 hours after incubation with SCGM, cells were exposed to keratocyte differentiation medium (KDM, (KDM; advanced-MEM (Invitrogen) with 10 ng/mL basic fibroblast growth factor (bFGF, Sigma-Aldrich), 0.1 mM L-ascorbic acid-2-phosphate (A2P, Sigma-Aldrich), L-glutamine (1× GlutaMax™-1; Invitrogen), 50 µg/ml Gentamicin (Invitrogen), 100 µg/ml penicillin (Mediatech, Inc.). KDM was changed twice a week for up to 6 weeks. On day 14, 28, and 42, scaffolds were selected randomly from 24-well plate and were subjected to two-photon fluorescent microscopy, scanning electron microscopy (SEM), transmission electron microscopy (TEM), western blotting, RT-PCR, and immunostaining.

Two-Photon Fluorescent Microscopy

Differentiated ADSC morphologies were observed with Two-photon Fluorescent microscope. Scaffolds were randomly chosen from 24-well plate on day 14, 28, and 42. Scaffolds were washed with PBS and were stained with CellTracker™ Green CMFDA (5-chloromethylfluorescein diacetate) (Invitrogen) for 10 minutes. Samples were observed under two-photon fluorescent microscope.

Electron Microscopy

The morphologies of the differentiated ADSCs and their secreted extracellular matrix on the scaffold were investigated by Scanning Electron Microscope (SEM). The specimens were fixed in cold 2.5% glutaraldehyde (25% glutaraldehyde EM grade, Taab Chemical) in 0.1 M PBS (sodium chloride, potassium chloride, sodium phosphate dibasic, potassium phosphate monobasic, Fisher), pH=7.3. The specimens were rinsed in PBS, post-fixed in 1% Osmium Tetroxide (Osmium Tetroxide crystals, Electron Microscopy Sciences) with 0.1% potassium ferricyanide (Potassium Ferricyanide, Fisher), dehydrated through a graded series of ethanol (30%~90%-Reagent Alcohol, Fisher, and 100%-Ethanol 200 Proof, Pharmco), and hexamethyldisilazane (HMDS). The yielded sample was investigated at 5 kV by Jeol JSM-6330F Scanning Electron Microscope (SEM) equipped with a digital camera.

The internal microstructures of the yielded ECM were investigated employing Transmission Electron Microscope (TEM). The sample was cut parallel and perpendicular to the alignment direction of PEUU fibrous scaffolds, respectively, in order to assess the influence of scaffold surface features on the ECM organization. The specimens were fixed in cold 2.5% glutaraldehyde (25% glutaraldehyde EM grade, Taab Chemical) in 0.1M PBS (sodium chloride, potassium chloride, sodium phosphate dibasic, potassium phosphate monobasic, Fisher), pH=7.3. The specimens were rinsed in 1×PBS, post-fixed in 1% Osmium Tetroxide (Osmium Tetroxide crystals, Electron Microscopy Sciences) with 0.1% potassium ferricyanide (Potassium Ferricyanide, Fisher), dehydrated through a graded series of ethanol (30%-90%-Reagent Alcohol, Fisher, and 100%-Ethanol 200 Proof, Pharmco) and embedded in Epon (Dodecenyl Succinic Anhydride, Nadic Methyl Anhydride, Scipoxy 812 Resin and Dimethylaminomethyl, Energy Beam Sciences). Semi-thin (300 nm) sections were cut on a Reichart Ultracut, stained with 0.5% Toluidine Blue (Toluidine Blue O and Sodium Borate, Fisher) and examined under the light microscope. Ultrathin sections (65 nm) were stained with 2% uranyl acetate (Uranyl Acetate dihydrate, Electron Microscopy Sciences, and methanol, fisher) and 1% phosphotungstic acid (Sigma-Aldrich), pH 3.2. The sections were examined and photographed at 80 kV on Jeol 1011 transmission electron microscope equipped with a digital camera.

Gene Expression

RNA of the differentiated ADSCs seeded on the PEUU scaffolds was isolated using the RNeasy mini kit (Qiagen, Valencia, Calif.). RNA was treated with DNAse I (Ambion) and was concentrated by alcohol precipitation. RNA (200 ng) was transcribed to cDNA in a 50 µL reaction containing 1×PCR II buffer (Roche Applied Science, Indianapolis, Ind.), 5 mM $MgCl_2$, 200 µM dNTP mixture (Roche), 2.5 µM random hexamers (Invitrogen), 0.4 U RNase inhibitor, and 125 U SuperScript II reverse transcriptase (Invitrogen). Quantitative PCR of cDNA was performed using assays containing fluorescent hybridization probes (TaqMan; Applied Biosystems, Foster City, Calif.) or with direct dye binding (SYBR Green; Applied Biosystems) according to the manufacturer's instructions. Reactions were carried out on triplicate samples for 40 cycles of 15 seconds at 95° C. and 1 minute at 60° C. after initial incubation at 95° C. for 10 minutes. Reaction volume was 20 µL. For TaqMan assays, reactions contained 1× Universal PCR Master Mix (Applied Biosystems), 1× gene mix, and 3.0 µL cDNA. For SYBR dye-based assays, the reactions contained 1×PCR buffer (Applied Biosystems), 3 mM $Mg^{2+}$, 200 µM dATP, dCTP, dGTP, and 400 µM dUTP, 0.025 U/mL AmpliTaq Gold polymerase, 1.6 µL cDNA and forward and reverse primers at optimized concentrations. Amplification of 18S rRNA and GAPDH were carried out for each cDNA as a qualitative external control. A dissociation curve for each SYBR-based reaction was generated on a real-time thermocycler (Gene-Amp ABI Prism 7700 Sequence Detection System; Applied Biosystems) to confirm the absence of nonspecific amplification. Amplification of 18S rRNA was performed for each cDNA (in triplicate) for normalization of RNA content. Relative mRNA abundance was calculated as the Ct for amplification of a gene-specific cDNA minus the average Ct for 18S expressed as a power of 2 ($2^{-\Delta C_t}$). Three individual gene-specific values thus calculated were averaged to obtain mean±SD. Eight target genes including, ABCG2, aldehyde dehydrogenase 3A1 (ALDH), AQP1, prostaglandin D2 synthase (PTGDS), Keratan sulfate 6-0-sulphotransferase (CHST6), keratocan, 18S, and GAPDH were chosen for PCR analysis.

Immunostaining of ADSC and Scaffold

Five PEUU e-spun fibrous scaffolds and ADSCs were randomly chosen from 24-well plate and fixed in 4.0% paraformaldehyde in PBS at room temperature for 20 minutes. Samples were rinsed in PBS and stored at 4° C. in PBS for further treatment. Each fixed samples was incubated in 10 wt-% heat-inactivated goat serum (HIGS) at room temperature for one hour to block nonspecific binding, rinsed in PBS, and incubated in 1-wt % bovine serum albumin (BSA)-PBS with mouse-monoclonal primary Collagen I, Collagen V, and Collagen VI antibodies overnight at 4° C. in a sealed moist box. For detecting keratocan and keratan sulfate, the samples were firstly digested and blocked in 1-wt % bovine serum albumin (BSA)-PBS with keratanase (0.5 unit/1W) for two hours at room temperature, rinsed in PBS, then stained by goat-monoclonal anti-human keratocan (a kind gift from Dr. Chia-Yang Liu) or goat anti-human keratan sulfate, respectively, and incubated overnight at 4° C. After three washes with PBS, secondary antibody Alexa Fluor 488-conjugated goat anti-mouse or Alexa Fluor 555-conjugated goat anti-rabbit (1:2,500) (Invitrogen-Molecular Probes, Eugene, Oreg., http://probes.invitrogen.com)

together with 4',6-diamidino-2-phenylindole (DAPI) (0.5 µg/ml) (Roche Molecular Biochemicals, Indianapolis, Ind.) were added to the samples, and incubated for 2 hours at room temperature. Omission of the primary antibody served as a negative control. The stained wholemounts were placed in aqueous mounting medium (Thermo Fisher Scientific, Pittsburgh, Pa.) and examined using an Olympus FluoView FV1000 confocal microscope (Olympus, Tokyo).

Immunoblot Analysis

KDM culture media were collected for 6 weeks. Proteoglycans were recovered from culture media by ion exchange chromatography on microcolumns (SPEC-NH$_2$, Ansys Diagnositcs, Lake Forest, Calif.). Two sets of samples were run on 4%-20% SDS-PAGE gels, transferred to polyvinylidene difluoride (PVDF) membranes and each membrane was subjected to immunoblotting with J19 antibody against keratan sulfate or with KeraC antibody against keratocan.

Results

Figure 23A:
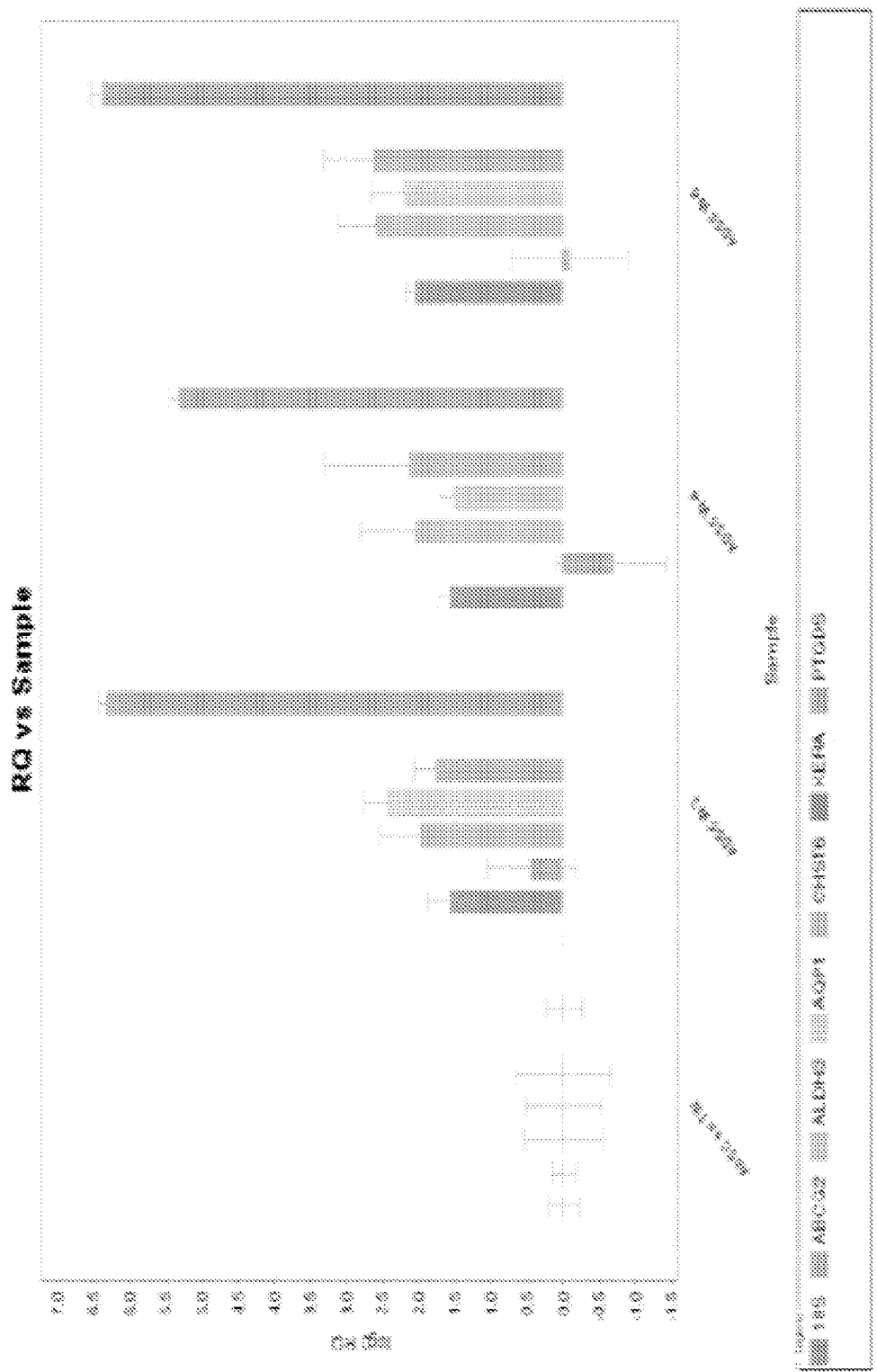
FIGS. 23A and 23B. Changes in gene expression of ADSCs (week 2, 4, 6) seeded on scaffolds. ADSCs on trans-well used as the control since they were incubated with stem cell growth medium (SCGM). 18S and GAPDH were used as qualitative external controls.
Figure 23B:
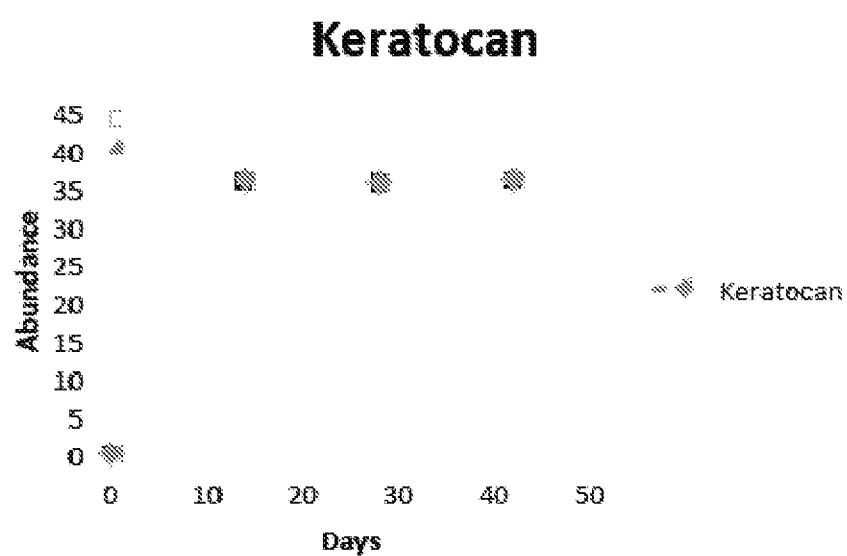

As shown above, ADSCs were differentiated into keratocytes when they were seeded in fibrin gels. The expression of keratocan in ADSCs exposed to KDM was confirmed with RT-PCR using human keratocan primers (FIG. 23A). As also shown (FIG. 23B), we confirmed that hCSSCs cultured on the nano-fibrous scaffolds upregulated several generic markers of keratocytes, including keratocan, aldehyde dehydrogenase 3A1 (ALDH), prostaglandin D2 synthase (PTGDS) and keratan sulphate 6-0-sulphotransferase (CHST6). In this example, we seeded ADSCs on the same nano-fibrous scaffolds and incubated them with KDM for 6 weeks. After 6 weeks, gene expressions of ADSCs cultured in KDM were analyzed with RT-PCR. ADSC cultured in KDM down-regulated the expression of ABCG2 and AQP-1, typical gene markers expressed by many adult stem cells and substantially up-regulated expression of generic markers for keratocytes, including keratocan, ALDH, PTGDS, and CHST6. GAPDH and 18S were used as controls. Since ADSCs typically do not express keratocan, RT-PCR results suggested that ADSCs on the scaffolds were differentiated into keratocytes in KDM 6 weeks after incubation.

Figure 24:
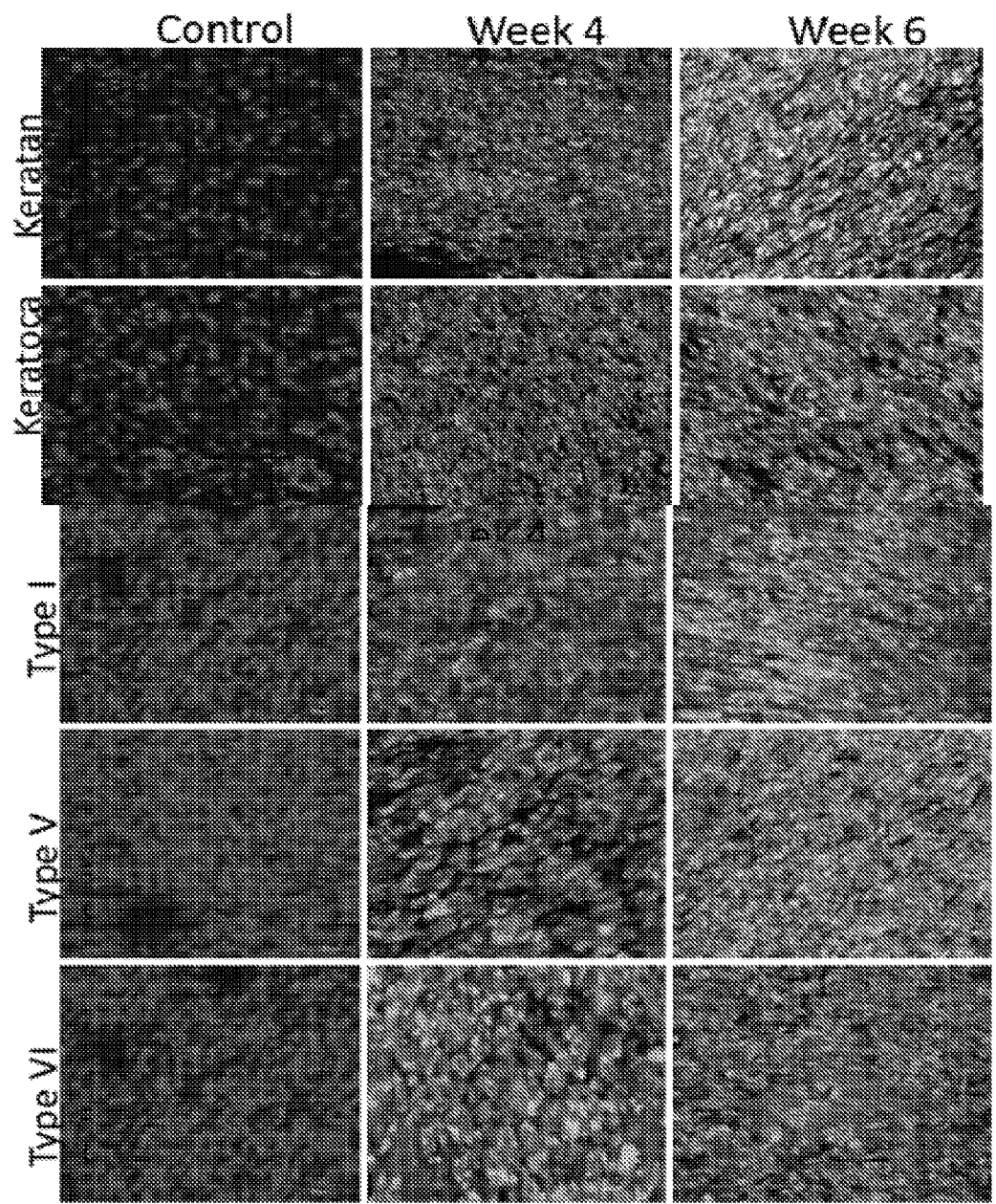
FIG. 24. Immunofluorescence microscopy images of ADSCs-secreted ECM on aligned nano-fibrous PEUU sheet.

In order to confirm gene expressions of ADSCs on scaffolds, the retention of collagens and proteoglycans typifying unique ECM of human corneal stromal tissue were examined by using whole-mount immunostaining. Contrary to previous result, Type I, V, and VI collagens were mostly intracellular and rarely formed ECM. FIG. 24 shows that Type I collagen was mostly intracellular in the week 4 sample. There was no representative alignment of cells on the scaffolds, but rather cells were spread out all over the scaffold without organization. In week 6 sample, the number of cells increased dramatically and cells became aligned in a particular orientation. Some positive stains for Type I collagen were detected; however, it was not highly orderly uniform Type-I collagen fibrils as shown in the hCSSC study. Similar trends were observed in Type V and VI immunostaining In the week 4 samples, cells were spread out and both Type V and VI collagens were mostly cell-associated. Some positive stains for Type VI collagen on ECM were detected with week 6 sample; however, it was not highly ordered Type VI collagen fibers. Additionally, the fibrils had no preferred orientation. Type V collagen was mostly detected within the cells and rarely on ECM. Keratan sulfate and keratocan were also cell-associated and were mostly detected within the cells in both time points. In general, the number of cells in all samples increased significantly over 6 weeks and cells were well-aligned. Interestingly, there were two or three layers of cells on top of the nano-fibrous scaffolds and each layer was formed with cells oriented into one direction. Immunostaining results were not completely consistent with RT-PCR data. Most of staining were observed within the cells and rarely seen on ECM. Although we detected some positive staining for Type I, V, VI collagens on ECM, they were randomly spread out between cells and were fragmented. In order to confirm our results, we decided to investigate ECM further with 2 photon microscopy.

Figure 25:
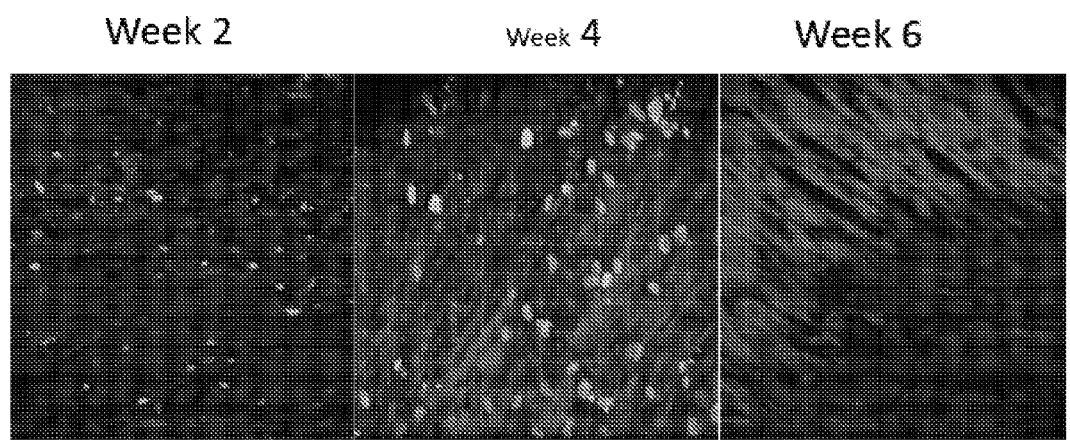
FIG. 25. Two-photon images of ADSCs secreted ECM on aligned nano-fibrous PEUU scaffold. The red was the second harmonic generation signal for collagens when excited at wavelength, λ=840 nm, but without staining. The green in week 2 and 4 was the nuclei stained with Sytox Green. The green in week 6 was the whole cell stained with CellTracker Green.

The highly co-aligned molecules of Type-I collagen render the collagen fibers strongly birefringent. More importantly, they feature a tremendous second-order nonlinear susceptibility because of its structural high non-centrosymmetry, resulting in a strong second harmonic generation (SHG). Accordingly, the ADSC-secreted extracellular matrix (ECM) was examined by two-photon microscopy. As shown in FIG. 25, although no staining, the SHG signal (in red) is very strong on both scaffolds when excited at wavelength, $\lambda=840$ nm. The SHG-visualized ECMs secreted by week 2 ADSCs were shown as fragmented fibers and some of them were intermingled together. Most of fiber-like structures were aligned in one orientation; however, there was no preferred orientation for cell alignment. In the week 4 sample, the amount of SHG-visualized ECMs secreted by ADSCs increased and they formed tissue-like mass in the form of fibers, although they were short in length. Although fibrils were aligned in one direction, cells were randomly spread out. In week 6, the number of cells increased dramatically, and they were aligned very well in one orientation. However, ECM secreted by cells was rather unorganized and spread out on the scaffold only where no cells aligned. For week 2 and 4 samples, we used Sytox Green dye to stain only the nuclei of the cells. The nuclei were ellipsoidal and did not show a preferred alignment direction on both scaffolds. However, the nuclei in the cells were not strictly related to the cell orientation. Therefore, next we used electron microscopy to investigate the relation between cell orientation and ECM alignment.

Figure 26:
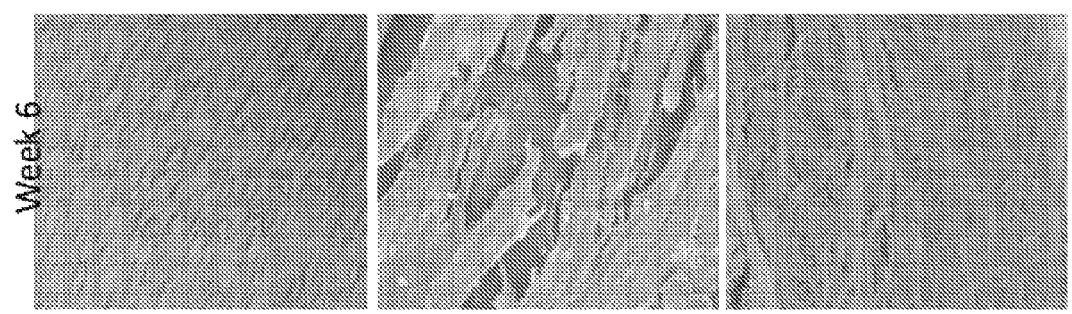
FIG. 26. SEM micrographs of ADSCs and ADSCs-secreted ECM on the scaffolds. The morphologies of ADSCs and ADSCs-secreted ECM were detailed from micron-scale to nano-scale with increasing magnification as shown above.

Using scanning electron microscopy, we observed detailed surface morphologies of ADSCs and their deposited ECMs on the scaffolds from micron-scale to nano-scale with increasing magnification. On the aligned nano-fibrous PEUU scaffolds, the seeded ADSCs were elongated, and uniformly oriented into one preferred direction after 2 weeks of incubation with KDM. There were many dense fibers between the cells on the scaffolds. The majority of fibers were aligned in particular orientation, but some were branched out in many directions, intermingled with each other and formed web-like structure. FIG. 26 revealed the detailed microstructures of the ADSCs-secreted fibril-like ECM. The fiber diameter was almost uniform, although the length of each fiber could hardly be accurately estimated. The longitudinal axes of the fibrils were closely parallel to each other. Between the fibers, there were numerous fiber-like side chains along the fibrils, which crosslinked them. The number of cells on the scaffolds was increased significantly over 6 weeks. Since SEM image represented only the top layer of ADSCs-secreted ECM organization, it was hard to make a conclusion about collagen organization of ECM without looking at layers underneath the top layer. Therefore, we needed to look at the internal microstructure with a transmission electron microscope.

Figure 27:
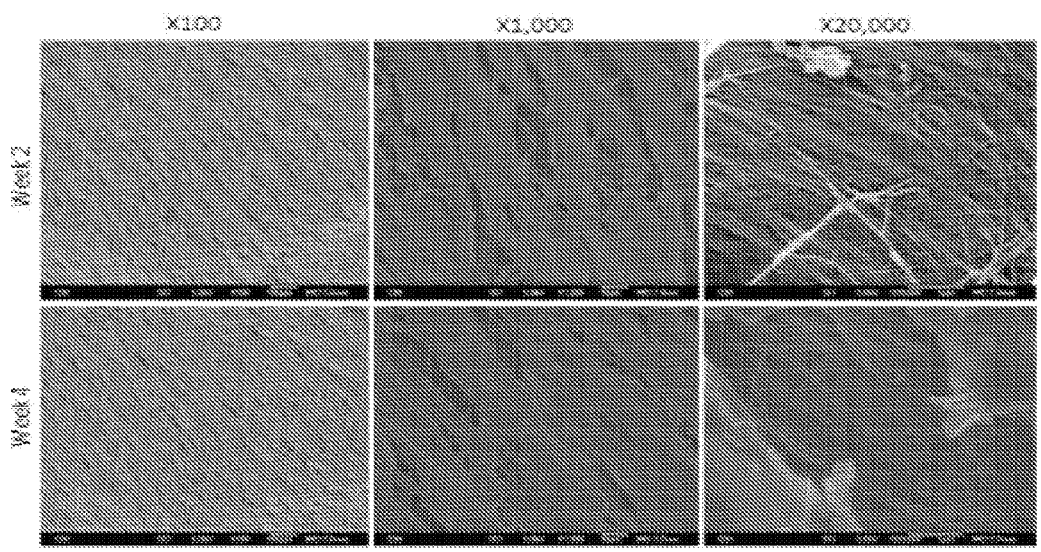
FIG. 27. Transmission electron micrographs of hCSSCs PEUU scaffolds seeded on aligned nano-fibrous PEUU sheet. When samples were microtomed along the fiber long axes, few fibrils were parallel to each other; however, mostly were fragmented.

Transmission electron micrographs of the ADSCs-secreted ECM in cross-section are shown in FIG. 27. Due to its structural anisotropy, the ADSCs-secreted ECM on aligned nano-fibrous scaffold was microtomed in two orthogonal fashions: along and cross the fiber long axis. For the sample microtomed cross the fiber along axes, the ADSCs-secreted ECM was sandwiched by the single cell layers (data not shown). For the sample microtomed along the fiber long axes, all of fibers are parallel to the view plane as shown in FIG. 27. In week 2 sample, cells looked healthy and some fibrils that were aligned with cells in the same direction were shown between cells. However, fibrils were rather short and looked like fragmented. When the sample was looked with higher magnification, few obvious fibrils were shown with unique characteristic D-spacing of the native Type-I collagen. In week 4 and 6 samples, number of cells and amount of fibrils increased, however, there was no particular pattern of fibrils between cells. They were rather spread out all over the place and formed clusters in random places. In week 6 sample, D-spacing banding pattern appeared again in few fibrils which were aligned with cells; however, they were very short. Rest of fibrils were fragmented, clustered together, and looked like small dots. Based on the scale, the thickness of the cell layers on the scaffold was about 20-22 µm.

Figure 28:
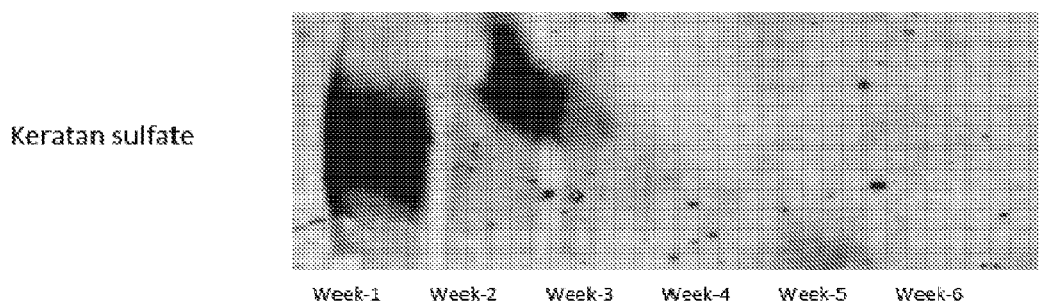
FIG. 28. Western blot of collected media for 6 weeks. The membrane was subjected to immunoblotting with J19 antibody against keratan sulfate.

So far, only morphology or gene expression of ADSCs on the scaffolds has been examined. Lastly, we wanted to investigate gene expression of the KDM media, in case any proteins were secreted from the cells into media during 6 weeks. Western blotting of KDM collected media were done with J19 antibody against keratan sulfate and with KeraC antibody against keratocan. Keratan sulfate expression was only detected from KDM media of first two weeks (FIG. 28). No keratocan expression was detected (data not shown).

Discussion

In this study, we have shown that ADSC, when they cultured on bioengineered 3-D orderly nano-structured collagen-fibril construct, have the potential to differentiate in vitro into cells that synthesize and secrete keratocyte-specific proteins as confirmed by both immunohistochemical and molecular evidence. In order to fabricate aligned nano-fibrous scaffolds, we prepared scaffolding by electrospinning poly(caprolactone) (PCL)-based poly(ester urethane) urea (PEUU). According to the previous studies, PEUU shows high elasticity and biocompatibility without toxic degradation products, and therefore, is ideal scaffolding material for soft tissue engineering. ADSCs were seeded on the scaffold and were induced to elongate and align following the PEUU fiber orientation as they cultured with KDM for 6 weeks.

Given the clear multipotent nature of ADSC, we investigated the ability of these cells to display keratocyte phenotypes when they were induced with KDM using methods previously successful in differentiating human corneal stromal stem cells (hCSSC) into keratocytes. Previous studies in the lab showed that keratan sulfate were much more enriched in cornea that any other tissue (Du, Y., et al. "Secretion and Organization of a Cornea-like Tissue in Vitro by Stem Cells from Human Corneal Stroma." Invest Ophthal Vis Sci 48 (2007): 5038-045). Therefore, keratan sulfate biosynthesis in vitro, represents the most important marker of the keratocyte phenotype. In addition to keratan sulfate, keratocan and ALDH3A1 mRNA are both highly expressed in keratocytes and upregulated as hCSSCs differentiate to keratocytes. Therefore, upregulation of keratocan and ALDH3A1 with synthesis of keratan sulfate will provide strong evidence that ADSCs were differentiated into keratocytes.

We successfully showed that ADSC cultured in KDM down-regulated the expression of ABCG2 and AQP-1, typical gene markers expressed by many adult stem cells and substantially up-regulated expression of generic markers for keratocytes, including keratocan, ALDH, PTGDS, and CHST6. However, in further studies to examine the retention of collagens and proteoglycans typifying unique ECM of human corneal stromal tissue by using the whole mount immunostaining, we observed that staining for keratan sulfate and keratocan indicated that these proteins mostly remained cell-associated. Although we observed positive staining of Type I and VI collagens on the scaffold, they were unorganized and were aligned with neither nano-fibrils of the scaffold or the cells. SEM and TEM results also demonstrated that fibers between cells were short, unorganized, fragmented and were not fully structured to form ECM. In some samples, we demonstrated that D-spacing banding pattern appeared in few fibrils which were aligned with cells; however, they were very short and random to form ECM construct. Two-photon microscopy images showed that cells were well aligned with scaffold fibrils, although ECM secreted by cells were unorganized and appeared to be fragmented fibers. Two-photon microscopy was used to detect highly co-aligned molecules of Type I collagens. Collagens, which demonstrate structural high non-centrosymmetry, will be resulted in a strong second harmonic generation. Lastly, we showed that there were no gene expressions of keratan sulfate or keratocan in KDM culture media we collected for 6 weeks. Expression of keratan sulfate was detected during first two weeks; however, gene expression decreased dramatically in 6 weeks.

Based on these results, we concluded that ADSCs cultured on PEUU nano-fibrous scaffold differentiated into keratocyte to some degree. We confirmed by RT-PCR that expression of genetic markers for keratocytes were upregulated. We also confirmed positive staining for Type I and VI collagens with immunostaining and presence of collagens on ECM with 2-photon microscopy. Furthermore, SEM and TEM data showed that ADSCs cultured with KDM generate some short, random, and fragmented fibers aligned or intermingled between cells and therefore, failed to form ECM construct. Although we showed increased gene expressions of generic markers of keratocyte, the true test of keratocyte function is elaboration of the highly organized, transparent ECM of the corneal stroma. Therefore, in order for ADSCs to be used in corneal cell therapy and tissue engineering, we need to further investigate methods to induce these cells to generate ECM construct when they are differentiated into keratocyte. One possible method will be changing chemical components of KDM by adding another growth factor, such as transforming growth factor beta.

In conclusion, our results provide novel evidence of potential of ADSC to adopt a keratocyte phenotype in vitro. Although more detailed molecular characterization of the tissue elaborated by the ADSC will be necessary for clinical application, demonstration of non-ocular adult stem cells' ability to become corneal-like keratocytes in vitro with application of bioengineered nano-fibrous scaffolds opens an important potential for bioengineering of corneal tissue using autologous cells.

Having described this invention, it will be understood to those of ordinary skill in the art that the same can be performed within a wide and equivalent range of conditions, formulations and other parameters without affecting the scope of the invention or any embodiment thereof.

We claim:

1. A method of preparing an aligned extracellular matrix (ECM) scaffold comprising culturing functional keratocytes on a template scaffold comprising one or more layers comprising aligned fibers of a biocompatible, biodegradable polymeric composition for a length of time sufficient for the cells to produce a product ECM scaffold having oriented fibers, wherein the biocompatible, biodegradable polymeric composition comprises:
- a polyurethane, a polyester, a polyether, a polyacrylamide, and/or a polycarbonate;
- a polyurethane, a polyester, a polyether, a polyacrylamide, and/or a polycarbonate-containing block copolymer, or
- a copolymer formed from one or more acrylic monomers, acrylamide monomers, succinimide monomers, glycolide monomers, caprolactone monomers, dioxanone monomers, lactide monomers, and/or carbonate monomers, and
- wherein the template scaffold degrades so that the product ECM scaffold does not contain the biocompatible, biodegradable polymeric composition of the template scaffold.

2. The method of claim 1, in which the biocompatible, biodegradable polymeric composition comprises a poly(ester urethane) urea elastomer.

3. The method of claim 1, in which the biocompatible, biodegradable polymeric composition comprises a polymer composition having a Lower Critical Solution Temperature of 35° C. or less.

4. The method of claim 3, in which the biocompatible, biodegradable polymeric composition comprises poly(N isopropyl acrylamide).

5. The method of claim 1, in which the template scaffold comprises a plurality of the one or more layers and wherein, the aligned fibers of a first layer of the plurality of the one or more layers are arranged at a different angle with respect to the aligned fibers of a second layer of the plurality of the one or more layers that is adjacent to the first layer.

6. The method of claim 5, in which the aligned fibers of a first layer of the plurality of layers are arranged at a 20° to 90° angle with respect to the aligned fibers of a second layer of the plurality of the one or more layers that is adjacent to the first layer.

7. The method of claim 1, further comprising preparing the template scaffold by electrospinning the biocompatible, biodegradable polymeric composition to prepare the aligned fibers of the one or more layers.

8. The method of claim 1, further comprising preparing the template scaffold by seeding one or more of the one or more layers with functional keratocytes or functional keratocyte precursors that are differentiated on the template scaffold to produce the functional keratocytes.

9. The method of claim 8, in which the one or more layers comprises a plurality of layers and further comprising stacking the one or more layers so that at least one layer is arranged so that its fibers are oriented at a different angle with respect to fibers of an adjacent layer.

10. The method of claim 8, in which the functional keratocytes or functional keratocyte precursors are seeded by electrospraying.

11. The method of claim 8, in which the functional keratocytes or functional keratocyte precursors are seeded by depositing cells onto the one or more layers in culture.

12. The method of claim 8, in which the functional keratocyte precursors are corneal stroma stem cells.

13. The method of claim 8, in which the functional keratocyte precursors are adipose-derived stem cells.

14. The method of claim 1, further comprising decellularizing the product ECM scaffold.

15. The method of claim 1, wherein the biocompatible, biodegradable polymeric composition comprises a polyurethane, a polyester, or a polymer composition having a Lower Critical Solution Temperature of 35° C. or less.

* * * * *